United States Patent
Dong et al.

(10) Patent No.: US 11,319,300 B2
(45) Date of Patent: May 3, 2022

(54) POLYFLUORO-SUBSTITUTED AROMATIC HETEROCYCLIC DERIVATIVE, PHARMACEUTICAL COMPOSITION CONTAINING SAME, AND APPLICATIONS THEREOF

(71) Applicant: ZHEJIANG UNIVERSITY, Hangzhou (CN)

(72) Inventors: Xiaowu Dong, Hangzhou (CN); Bo Yang, Hangzhou (CN); Yongzhou Hu, Hangzhou (CN); Qiaojun He, Hangzhou (CN); Qinjie Weng, Hangzhou (CN); Wenhu Zhan, New York, NY (US); Tao Liu, Hangzhou (CN)

(73) Assignee: GUANGZHOU LIXIN PHARMACEUTICAL CO., LTD., Guangzhou (CN)

( * ) Notice: Subject to any disclaimer, the term of this patent is extended or adjusted under 35 U.S.C. 154(b) by 165 days.

(21) Appl. No.: 16/480,599

(22) PCT Filed: Jan. 19, 2018

(86) PCT No.: PCT/CN2018/073325
§ 371 (c)(1),
(2) Date: Jul. 25, 2019

(87) PCT Pub. No.: WO2018/137555
PCT Pub. Date: Aug. 2, 2018

(65) Prior Publication Data
US 2020/0165229 A1    May 28, 2020

(30) Foreign Application Priority Data

Jan. 24, 2017 (CN) .......................... 201710053576.8

(51) Int. Cl.
*A61P 35/00*     (2006.01)
*A61P 35/04*     (2006.01)
*C07D 401/12*    (2006.01)
*C07D 403/12*    (2006.01)

(52) U.S. Cl.
CPC ............ *C07D 403/12* (2013.01); *A61P 35/04* (2018.01); *C07D 401/12* (2013.01); *C07B 2200/07* (2013.01)

(58) Field of Classification Search
CPC ...... C07B 2200/07; A61P 35/00; A61P 35/04; C07D 401/12; C07D 403/12
See application file for complete search history.

(56) References Cited

U.S. PATENT DOCUMENTS 10,233,180 B2 *  3/2019  Dong ................... C07D 409/14
2015/0166509 A1  6/2015  Chen et al.

FOREIGN PATENT DOCUMENTS

CN    104926788    9/2015
CN    101921268    8/2016

OTHER PUBLICATIONS

RN11811536-73-8, registry database compound, 2015.*

* cited by examiner

*Primary Examiner* — Sun Jae Yoo
(74) *Attorney, Agent, or Firm* — Jiwen Chen; Jacobson Holman PLLC

(57) ABSTRACT

A polyfluoro-substituted aromatic heterocyclic derivative having the structure as represented by formula I or formula I', wherein at least one of $R_1$ and $R_2$ is a fluorine atom, and at least two substituents of Rc, Rd, Re, and Rf are fluorine atoms; and an optical isomer of the derivative, or a pharmaceutically acceptable salt or solvate of the same, or a pharmaceutically acceptable salt or solvate of the optical isomer of the same. A composition containing the polyfluoro-substituted aromatic heterocyclic derivative and an application of the composition in preparing an anti-tumour medicament. The compound provides significant inhibitory effects with respect to Akt1 and demonstrates strong proliferation inhibitory activity with respect to tumour cell lines such as an ovarian cancer cell line, a colon cancer cell line, and a prostate cancer cell line. Therefore, the compound may be used as an Akt inhibitor in the medicament for treating a cell proliferation-related solid tumour or blood cancer in the human or animal body.

4 Claims, No Drawings

POLYFLUORO-SUBSTITUTED AROMATIC HETEROCYCLIC DERIVATIVE, PHARMACEUTICAL COMPOSITION CONTAINING SAME, AND APPLICATIONS THEREOF

This is a U.S. national stage application of PCT Application No. PCT/CN2018/073325 under 35 U.S.C. 371, filed Jan. 19, 2018 in Chinese, claiming priority of Chinese Application No. 201710053576.8, filed Jan. 24, 2017, all of which are hereby incorporated by reference.

TECHNICAL FIELD

The present invention relates to the technical field of medicine, in particular to a polyfluoro-substituted aromatic heterocyclic derivative as an Akt inhibitor, a pharmaceutical composition containing the same, and its application in against tumour.

BACKGROUND

Malignant tumours are one of the major diseases that threaten human life and health. With the increasing seriousness of environmental pollution, life pressures and aging population, etc., the malignant tumours have become a leading cause of death for Chinese residents. Cancer prevention and treatment research has become the focus of global attention. The main treatments for cancer include surgery, radiation therapy, drug chemotherapy and so on, wherein drug chemotherapy is the most important among them. Traditional antineoplastic drugs are mostly cytotoxic drugs that act on mitosis, synthesis and repair of DNA, and have widespread shortcomings such as poor efficacy to solid tumour, large poisonous side effects and easy to produce multidrug resistance, which make its clinical treatment subject to greater restrictions. In recent years, the development of targeted antineoplastic drugs has progressed rapidly, new antineoplastic drugs have emerged, the Tinib tyrosine kinase inhibitors represented by the Bcr-Abl inhibitor imatinib, the EGFR inhibitor gefitinib and the Chinese independent innovation drug Ectinib, have been widely used in the clinical treatment of cancer and have the characteristics of significant effects and less toxic side effects. In view of the excellent performances of these new antineoplastic drugs, the research of small molecule targeted antineoplastic drugs has become an important topic in the global pharmaceutical industry and it is still a hot spot to find novel antineoplastic drugs with different mechanism of action in the research and development of new drugs at home and abroad.

In recent years, PI3K/Akt/mTOR signal pathway has provided great opportunities for cancer therapy, the development of antineoplastic drugs around this pathway has become a hot field in global research and Akt as a key node protein in this signal pathway has always been a concern. Akt, also known as protein kinase B, is a serine/threonine kinase that is a member of the AGC protein kinase family. Human Akts mainly include three subtypes: Akt1, Akt2, and Akt3. Although these three subtypes are assigned to different chromosomes, there are high (more than 80%) sequence homologies among them. The three subtypes of Akt structurally comprise an amino terminal PH domain, a central kinase domain, and a carboxy terminal regulatory domain. The PH domain, i.e. the inositol phosphate ester binding region, regulates the binding of Akt to phosphatidyl-3,4,5-triphosphate (PIP3); the kinase catalytic region contains a threonine phosphorylation key site, i.e. T308 site, that activates Akt, and the carboxyl terminal contains a serine phosphorylation site, i.e. the S473 site. In the cytoplasm, Akt is mainly present in a non-activated form of 'PH-in', when PI3K kinase is activated by growth factors, PI3K phosphorylates hydroxyl groups at the 3-position of phosphatidyl-4,5-diphosphate (PIP2) to form phosphatidyl-3,4,5-triphosphate (PIP3), and the latter can bind to the PH domain of Akt to recruit it to the cell membrane and cause it to undergo a conformational transition ('PH-out'), exposing two phosphorylation sites. When the T308 and S473 sites are phosphorylated by the phosphatidylinositol-dependent protein kinase PDK1 and the mammalian target of rapamycin mTOR2 respectively, the fully activated Akt detaches from the cell membrane, activates a series of downstream signalling molecules, and then regulates physiological process of cells.

Akt plays an extremely important biological role in cell growth, survival, proliferation, apoptosis, angiogenesis, autophagy and so on. The study found that Akt is over-expressed in various human tumours such as gastric cancer, prostate cancer, ovarian cancer, breast cancer, etc, and the dysfunction or abnormal activation of Akt is closely related to the occurrence, development, metastasis and drug resistance to chemotherapy of these tumours. Therefore, Akt has become an antineoplastic drug target with broad development prospects, and it is an important strategy to find novel and highly effective Akt inhibitors for the development of antineoplastic drugs at present.

With the deep understanding of the structure and function of Akt, many different types of Akt inhibitors have been reported. According to its mode of action, it can be divided into three major classes: phosphatidylinositol (PIP) analogues, allosteric inhibitors and ATP competitive inhibitors. The phosphatidylinositol analogue inhibitor acts on the PH domain of Akt, blocking the combination of PIP3 and Akt, and preventing it from transferring from the cytoplasm to the cell membrane, thereby inhibiting the activation of Akt. Representative inhibitors are DPIEL, PIAS and perifosine, wherein the perifosine of Aeterna Antaris Corp has been used in a phase III clinical trial for the oral administration of new drugs for the treatment of multiple myeloma and refractory colorectal cancer, but it finally failed due to poor efficacy.

Akt allosteric inhibitors have received increasing attention in the industry in recent years due to their high specificity. As described above, Akt is mainly present in the conformation of PH-in' before activation, the PH domain and the kinase catalytic region are in a folded state, a special allosteric site is produced between the two regions, and the Akt allosteric inhibitor binds to this site with locking its PH-in' state and restricting the conformational change of Akt, thereby inhibiting the activation of the Akt. Since the three subtypes of Akt have differences in this allosteric site, this type of inhibitor can better achieve selectivity between the Akt subtypes. Representative Akt allosteric inhibitor MK-2206 has now entered phase II clinical trials for the treatment of various cancers such as gastric cancer, breast cancer and lymphoma.

ATP competitive inhibitors are the most widely studied class of Akt inhibitors that compete with ATP for acting on ATP binding pockets, hindering its phosphorylation of substrate proteins. Since Akt tighter with PKA, PKC, ROCK and so on belong to the AGC protein family, their ATP binding pockets are highly similar, which brings a huge challenge for designing specific Akt inhibitors. A large number of different structural types of small molecule ATP competitive inhibitors have been reported, and many of them have entered or are in clinical research, such as GSK690693, AZD5363, GDC-0068, GSK2110183, and GSK2141795.

SUMMARY OF THE INVENTION

An object of the present invention is to provide a novel polyfluoro-substituted aromatic heterocyclic derivative with strong anticancer action and Akt inhibition, and a pharmaceutically acceptable salt or solvate thereof.

The present invention also provides a pharmaceutical composition comprising the above polyfluoro-substituted aromatic heterocyclic derivative and a pharmaceutically acceptable salt or solvate thereof.

The present invention also provides an application for preparation of an antitumour drug using polyfluoro-substituted aromatic heterocyclic derivative and a pharmaceutically acceptable salt or solvate thereof.

The present invention adopts the following technical solutions:

The present application provides a polyfluoro-substituted aromatic heterocyclic derivative, having a structure as represented by formula I or formula I',

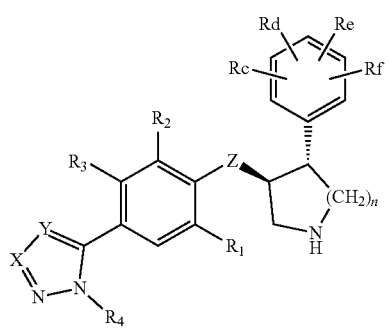

I

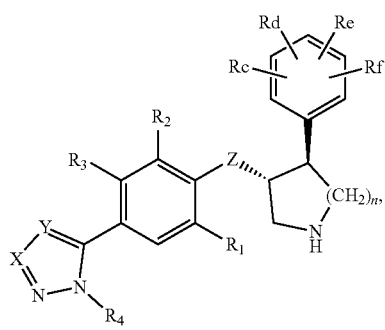

I' or an optical isomer thereof; or a pharmaceutically acceptable salt or solvate thereof; or a pharmaceutically acceptable salt or solvate of the optical isomer thereof,
wherein X and Y are independently selected from —C(Ra)— and —N—, and at least one of them is —C(Ra)—; Ra is selected from H, halogen, hydroxy, carboxyl, hydroxymethyl, saturated or unsaturated $C_1$-$C_4$ hydrocarbyl (including alkyl, alkenyl, alkynyl), halogenated $C_1$-$C_4$ alkyl, $C_1$-$C_4$ alkoxy, halogenated $C_1$-$C_4$ alkoxy, unsubstituted or substituted aryl of $C_4$-$C_{12}$, unsubstituted or substituted heterocyclic aryl of $C_4$-$C_{12}$, unsubstituted or substituted cycloalkyl of $C_3$-$C_8$;
$R_1$ and $R_2$ are each independently selected from a group consisting of H, F, Cl, Br, $CH_3$, and $CF_3$, and at least one of them is a fluorine atom; $R_3$ is H, $CH_3$, $CF_3$, F or Cl; $R_4$ is a $C_1$-$C_3$ alkyl or cycloalkyl;

Z is selected from

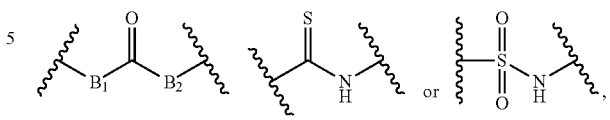

$B_1$ and $B_2$ are each independently selected from N(Rb) or a deletion, wherein Rb is independently selected from H, $C_1$-$C_3$ alkyl or cycloalkyl; Z in the present invention is equivalent to a bridging group for connection of two compound fragments; the term "deletion" as used herein refers to the side of the deletion is directly connected to the corresponding compound fragment by the intermediate carbonyl carbon when B1 or/and B2 are deleted, for example, when B1 is deleted, the structure of z is

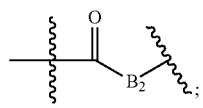

n is 1, 2, or 3, and
Rc, Rd, Re, and Rf are each independently selected from a group consisting of H, F, Cl, Br, $CF_3$, and $CF_2H$, and at least two of substituents are fluorine atoms.

Furthermore, preferably, the polyfluoro-substituted aromatic heterocyclic derivative of the present application has a structure as represented by formula II-1, formula II-2 or formula II-3,

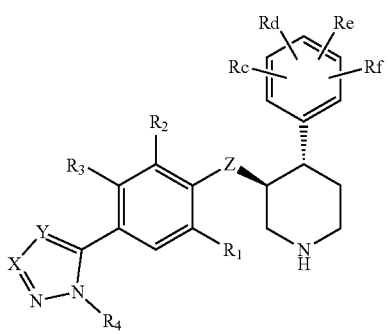

II-1

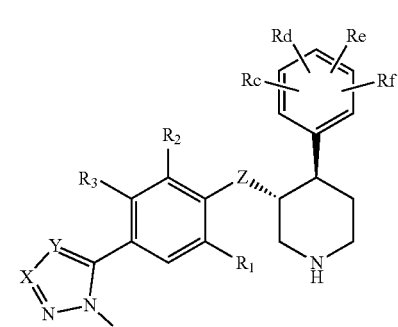

II-2

-continued

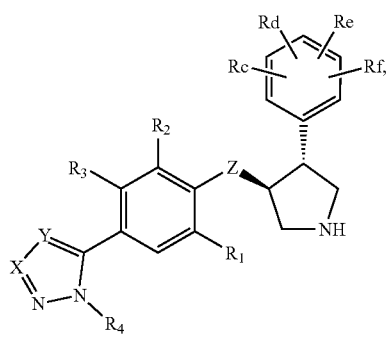

II-3 or has an optical isomer thereof, a pharmaceutically acceptable salt or solvate thereof, or a pharmaceutically acceptable salt or solvate of the optical isomer thereof,
wherein X, Y, $R_1$, $R_2$, Z, Rc, Rd, Re, and Rf are as defined above.

Furthermore, preferably, the polyfluoro-substituted aromatic heterocyclic derivative of the present application has a structure as represented by formula III-1, formula III-2 or formula III-3,

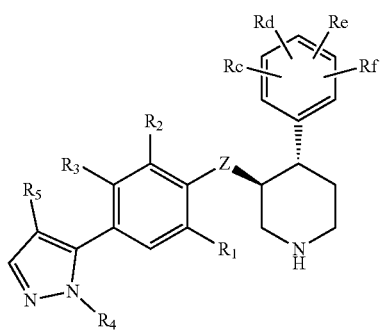

III-1

III-2

III-3 or has an optical isomer thereof, a pharmaceutically acceptable salt or solvate thereof, or a pharmaceutically acceptable salt or solvate of the optical isomer thereof,
wherein $R_1$, $R_2$, $R_3$, $R_4$, and Z are the same as defined above, and $R_5$ is H, halogen (F, Cl, Br), $C_1$-$C_3$ alkyl or cycloalkyl.

Furthermore, the

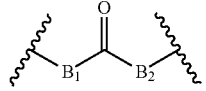

in the Z is preferably the following structure:

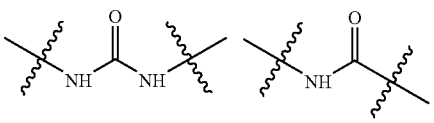

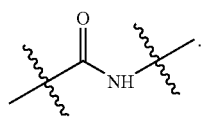

As a further preference, the polyfluoro-substituted aromatic heterocyclic derivative of the present application has a structure as represented by formula IVa, formula IVb, formula IVc or formula IVd,

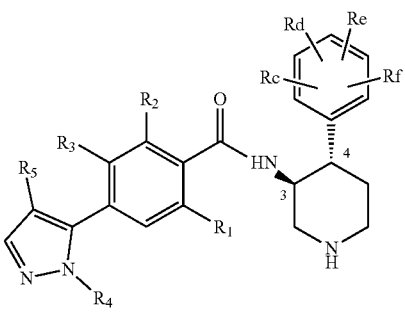

(3S,4S)-IVa

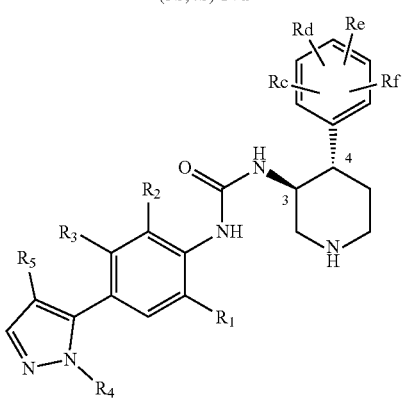

(3S,4S)-IVb

-continued

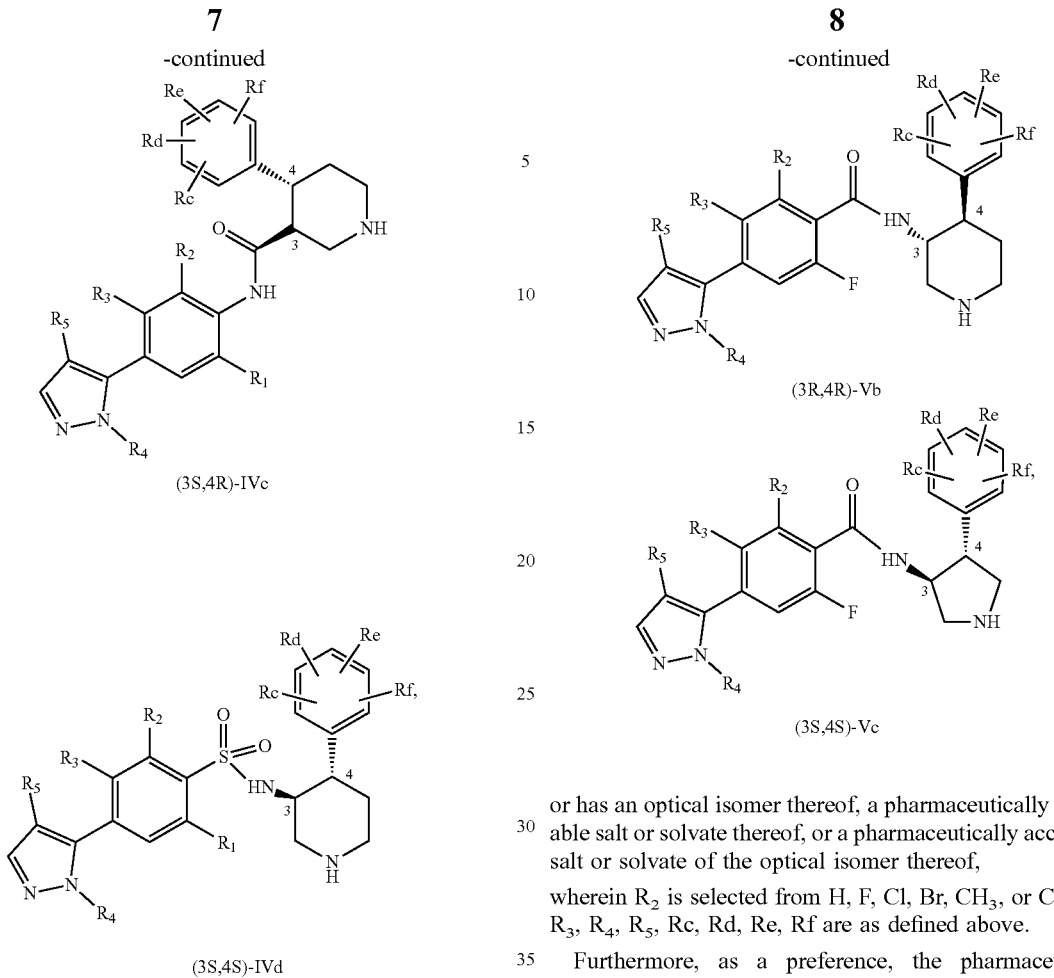

(3S,4R)-IVc (3S,4S)-IVd (3R,4R)-Vb (3S,4S)-Vc or has an optical isomer thereof, a pharmaceutically acceptable salt or solvate thereof, or a pharmaceutically acceptable salt or solvate of the optical isomer thereof.

Wherein $R_1$, $R_2$, $R_5$, Rc, Rd, Re, and Rf are as defined above.

Furthermore, a preferred compound of the invention has a structure as represented by formula Va, formula Vb, or formula Vc, or has an optical isomer thereof, a pharmaceutically acceptable salt or solvate thereof, or a pharmaceutically acceptable salt or solvate of the optical isomer thereof, wherein $R_2$ is selected from H, F, Cl, Br, $CH_3$, or $CF_3$, and $R_3$, $R_4$, $R_5$, Rc, Rd, Re, Rf are as defined above.

Furthermore, as a preference, the pharmaceutically acceptable salt thereof is preferably a salt consisting of one or more of 2-hydroxysuccinic acid((±)-malic acid), (S)-2-hydroxysuccinic acid(L-malic acid), (R)-2-hydroxyl succinic acid(D-malic acid), (2R, 3R)-2,3-dihydroxysuccinic acid, (2S,3S)-2,3-dihydroxysuccinic acid, L-tartaric acid, D-tartaric acid, tartaric acid, methanesulfonic acid, p-toluenesulfonic acid, and 2-hydroxypropanetricarboxylic acid. As a further preference, the pharmaceutically acceptable salt thereof is preferably a salt consisting of one or more of 2-hydroxysuccinic acid((±)-malic acid), (S)-2-hydroxysuccinic acid(L-malic acid), (R)-2-hydroxyl succinic acid(D-malic acid), (2R, 3R)-2,3-dihydroxysuccinic acid, (2S,3S)-2,3-dihydroxysuccinic acid, L-tartaric acid, D-tartaric acid, tartaric acid, and 2-hydroxypropanetricarboxylic acid. As a further preference, a structure of L-malate is represented by formula VIa, or formula VIb,

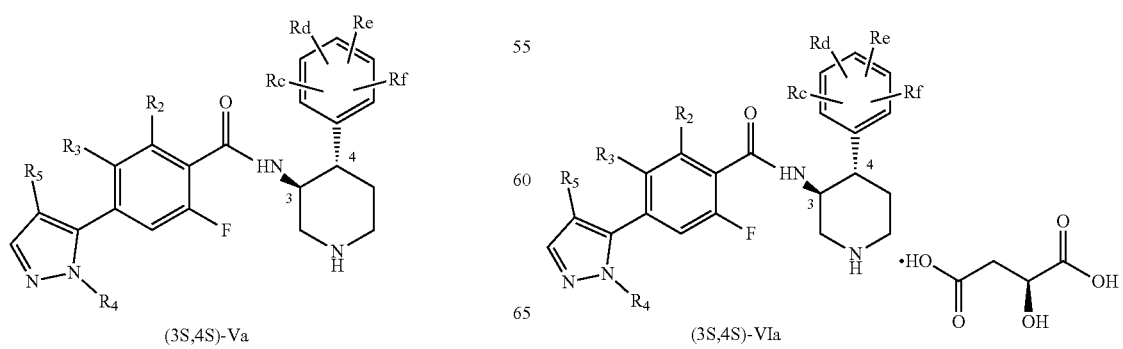

(3S,4S)-Va (3S,4S)-VIa

-continued

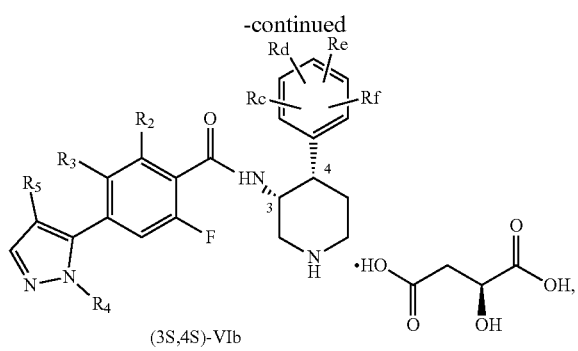

(3S,4S)-VIb or has an optical isomer thereof, wherein $R_2$ is selected from a group consisting of H, F, Cl, Br, $CH_3$, and $CF_3$; and $R_3$, $R_4$, $R_5$, Rc, Rd, Re, and Rf are as defined above.

As a further preference, $R_1$ and $R_2$ are each independently selected from a group consisting of H, F, Cl, $CH_3$, and $CF_3$, and at least one of them is a fluorine atom; R is H or F; R is a methyl, ethyl, cyclopropyl C1-C3 alkyl or cycloalkyl; X is methyl; and Y is N or —C(Ra)—, wherein, Ra is selected from a group consisting of H, Cl, methyl, cyclopropyl, hydroxyethyl, Br, and F; n is 1 or 2; at least two of Rc, Rd, Re, and Rf are fluorine, and the rest are H; Rc, Rd, Re, and Rf are further preferably 3, 4 disubstituted fluorine, 3, 4, 5 trisubstituted fluorine, 1, 2, 4, 5 tetrasubstituted fluorine, 2, 4 disubstituted fluorine, and the rest are H.

Z is selected from

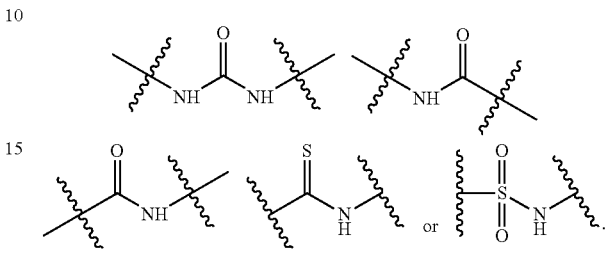

Specifically, according to formula I and formula I', preferred compounds of the invention are:

| No. | Structure | Name |
|---|---|---|
| VII-1 | 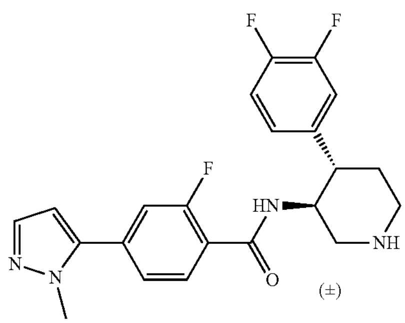 [SMILES: Cn1nccc1-c1ccc(C(=O)N[C@@H]2CNCC[C@H]2c2ccc(F)c(F)c2)c(F)c1] | 4-(1-methyl-1H-pyrazole-yl)-N-((±)-4-(3,4-difluorophenyl)piperidin-3-yl)-2-fluorobenzamide |
| VII-1a | 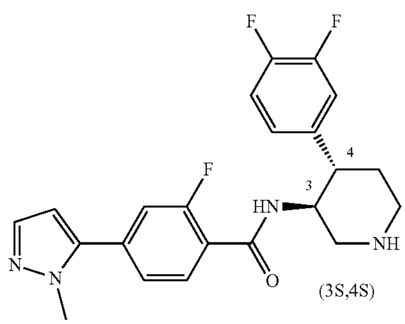 [SMILES: Cn1nccc1-c1ccc(C(=O)N[C@@H]2CNCC[C@H]2c2ccc(F)c(F)c2)c(F)c1] | 4-(1-methyl-1H-pyrazole-yl)-N-((3S,4S)-4-(3,4-difluorophenyl)piperidin-3-yl)-2-fluorobenzamide |
| VII-1b | 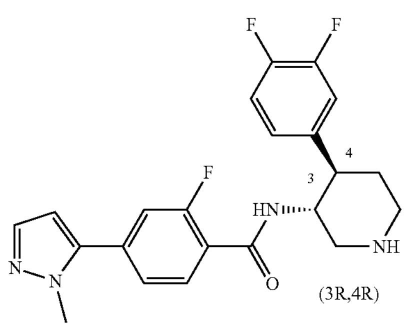 [SMILES: Cn1nccc1-c1ccc(C(=O)N[C@H]2CNCC[C@@H]2c2ccc(F)c(F)c2)c(F)c1] | 4-(1-methyl-1H-pyrazole-yl)-N-((3R,4R)-(3,4-difluorophenyl)piperidin-3-yl)-2-fluorobenzamide |

-continued

| No. | Structure | Name |
|---|---|---|
| VII-2 | 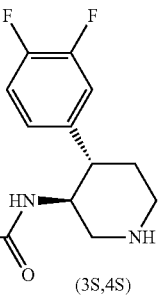 | 4-(1-methyl-4-chloro-1H-pyrazole-yl)-N-((3S,4S)-(3,4-difluorophenyl)piperidin-3-yl)-2-fluorobenzamide |
| VII-3 | 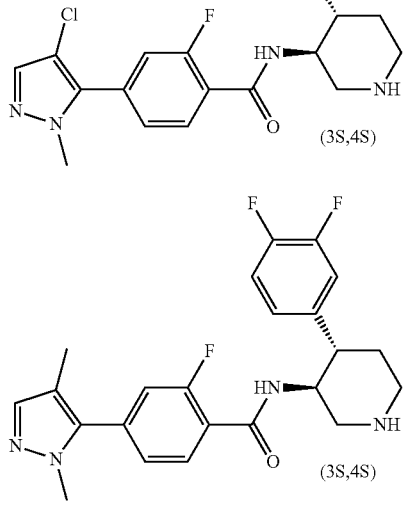 | 4-(1,4-dimethyl-1H-pyrazole-yl)-N-((3S,4S)-4-(3,4-difluorophenyl)piperidin-3-yl)-2-fluorobenzamide |
| VII-4 | 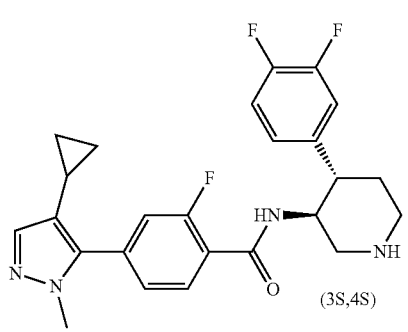 [SMILES: Cn1ncc(C2CC2)c1-c1ccc(C(=O)N[C@@H]2CNCC[C@H]2c2ccc(F)c(F)c2)c(F)c1] | 4-(1,4-dimethyl-1H-pyrazole-yl)-N-((3S,4S)-4-(3,4-difluorophenyl)piperidin-3-yl)-2-fluorobenzamide |
| VII-5 | 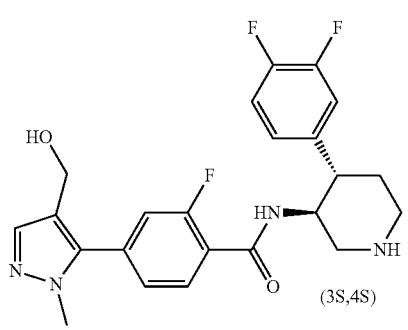 [SMILES: Cn1ncc(CO)c1-c1ccc(C(=O)N[C@@H]2CNCC[C@H]2c2ccc(F)c(F)c2)c(F)c1] | 4-(1-methyl-4-hydroxymethyl-1H-pyrazole-yl)-N-((3S,4S)-(3,4-difluorophenyl)piperidin-3-yl)-2-fluorobenzamide |
| VII-6 | 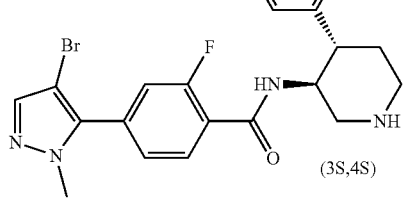 | 4-(1-methyl-4-bromo-1H-pyrazole-yl)-N-((3S,4S)-(3,4-difluorophenyl)piperidin-3-yl)-2-fluorobenzamide |

| No. | Structure | Name |
|---|---|---|
| VII-7 | 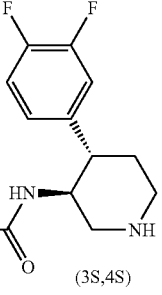 | 4-(1-methyl-4-fluoro-1H-pyrazole-yl)-N-((3S,4S)-(3,4-difluorophenyl)piperidin-3-yl)-2-fluorobenzamide |
| VII-8 | 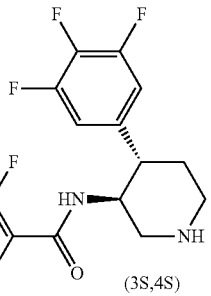 | 4-(1-methyl-1H-pyrazole-yl)-N-((3S,4S)-(3,4,5-trifluorophenyl)piperidin-3-yl)-2-fluorobenzamide |
| VII-9 | 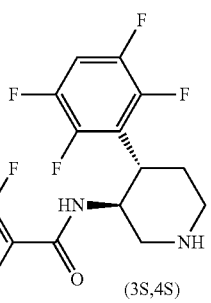 | 4-(1-methyl-1H-pyrazole-yl)-N-((3S,4S)-(2,3,5,6-tetrafluorophenyl)piperidin-3-yl)-2-fluorobenzamide |
| VII-10 | 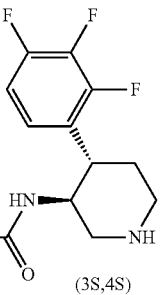 | 4-(1-methyl-1H-pyrazole-yl)-N-((3S,4S)-(2,3,4-trifluorophenyl)piperidin-3-yl)-2-fluorobenzamide |

| No. | Structure | Name |
|---|---|---|
| VII-11 | 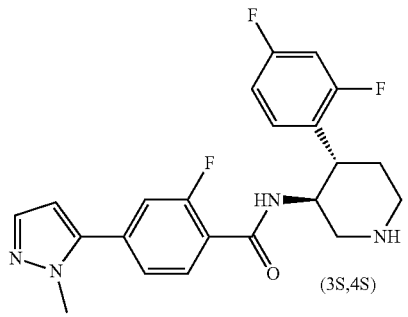 [SMILES: Cn1nccc1-c1ccc(C(=O)N[C@@H]2CNCC[C@H]2c2ccc(F)cc2F)c(F)c1] | 4-(1-methyl-1H-pyrazole-yl)-N-((3S,4S)-(2,4-difluorophenyl)piperidin-3-yl)-2-fluorobenzamide |
| VII-12 | 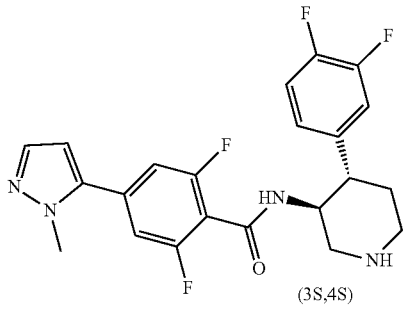 [SMILES: Cn1nccc1-c1cc(F)c(C(=O)N[C@@H]2CNCC[C@H]2c2ccc(F)c(F)c2)c(F)c1] | 4-(1-methyl-1H-pyrazole-yl)-N-((3S,4S)-4-(3,4-difluorophenyl)piperidin-3-yl)-2,6-difluorobenzamide |
| vII-13 | 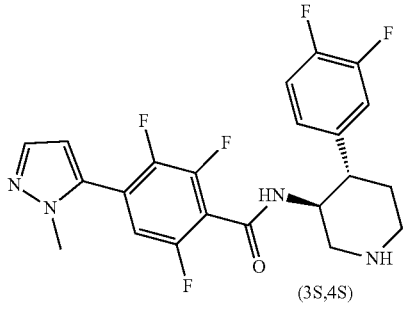 [SMILES: Cn1nccc1-c1cc(F)c(C(=O)N[C@@H]2CNCC[C@H]2c2ccc(F)c(F)c2)c(F)c1F] | 4-(1-methyl-1H-pyrazole-yl)-N-((3S,4S)-4-(3,4-difluorophenyl)piperidin-3-yl)-2,3,6-trifluorobenzamide |
| vII-14 | 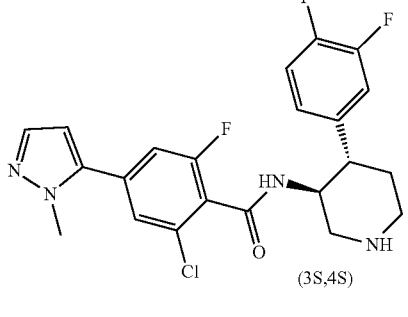 | 4-(1-methyl-1H-pyrazole-yl)-N-((3S,4S)-4-(3,4-difluorophenyl)piperidin-3-yl)-2,3,6-trifluorobenzamide |
| vII-15 | 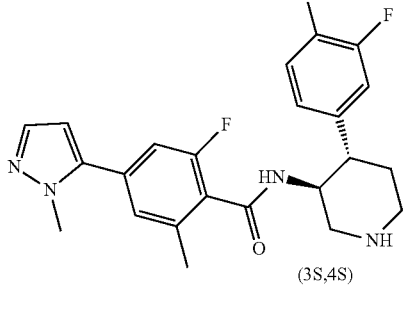 | 4-(1-methyl-1H-pyrazole-yl)-N-((3S,4S)-4-(3,4-difluorophenyl)piperidin-3-yl)-2-methyl-6-fluorobenzamide |

-continued

| No. | Structure | Name |
|---|---|---|
| vII-16 | (3S,4S) | 4-(1-methyl-1H-pyrazole-yl)-N-((3S,4S)-4-(3,4-difluorophenyl)piperidin-3-yl)-2-trifluoromethyl-6-fluorobenzamide |
| vII-17 | (3S,4S) | 4-(1-methyl-1H-pyrazole-yl)-N-((3S,4S)-4-(3,4-difluorophenyl)piperidin-3-yl)-2,3-difluorobenzamide |
| vII-18 | (3S,4S) | 4-(1-methyl-1H-pyrazole-yl)-N-43S,4S)-4-(3,4-difluorophenyl)piperidin-3-yl)-2,5-difluorobenzamide |
| vII-19 | (3S,4R) | 4-(1-methyl-4-chloro-1H-pyrazole-yl)-N-((3S,4R)-(3,4-difluorophenyl)pyrrolidin-3-yl)-2-fluorobenzamide |
| vII-20 | (3S,4R) | 4-(1-methyl-1H-pyrazole-yl)-N-((3S,4R)-(3,4-difluorophenyl)pyrrolidin-3-yl)-2-fluorobenzamide |

-continued

| No. | Structure | Name |
|---|---|---|
| VII-21 | (3S,4R) | 4-(1-methyl-1H-pyrazole-yl)-N-((3S,4R)-(3,4-difluorophenyl)pyrrolidin-3-yl)-2,6-difluorobenzamide |
| VII-22 | (3S,4S) | 1-((3S,4S)-4-(3,4-difluorophenyl)piperidin-3-yl)-3-(2-fluoro-4-(1-methyl-1H-pyrazole-5)-yl)phenylurea |
| VII-23 | (3S,4S) | N-((3S,4S)-4-(3,4-difluorophenyl)piperidin-3-yl)-2-fluoro-4-(1-methyl-1H-pyrazol-5-yl)benzenesulfonamide |
| VII-24 | (3S,4S) | (3S,4R)-4-(3,4-difluorophenyl)-N-(2-fluoro-4-(1-methyl-1H-pyrazolyl)phenyl)piperidine-3-carbamide |
| VII-25 | (3S,4S) | (3S,4R)-4-(3,4-difluorophenyl)-N-(2-fluoro-4-(1-methyl-4-chloro-1H-pyrazolyl)phenyl)piperidine-3-carbamide |

-continued
| No. | Structure | Name |
|---|---|---|
| VII-26 | 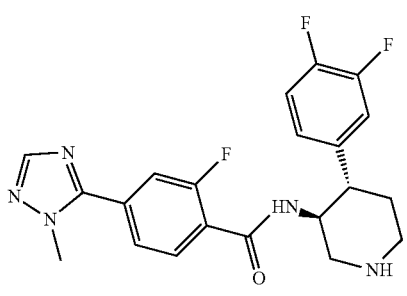 (3S,4S) | 4-(1-methyl-1H-1,2,4-triazol-5-yl)-N-43S,4S)-4-(3,4-difluorophenyl)piperidine-3-yl)-2-fluorobenzamide |
| VII-27 | 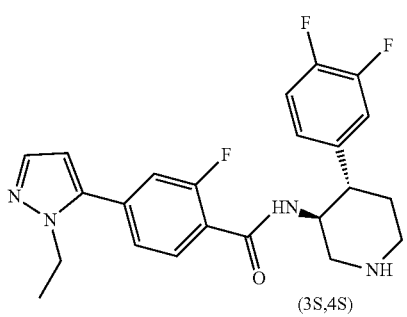 [SMILES: CCn1nccc1-c1ccc(C(=O)N[C@@H]2CNCC[C@H]2c2ccc(F)c(F)c2)c(F)c1] (3S,4S) | 4-(1-ethyl-1H-pyrazole-yl)-N-((3S,4S)-4-(3,4-difluorophenyl)piperidin-3-yl)-2-fluorobenzamide |
| VII-28 | 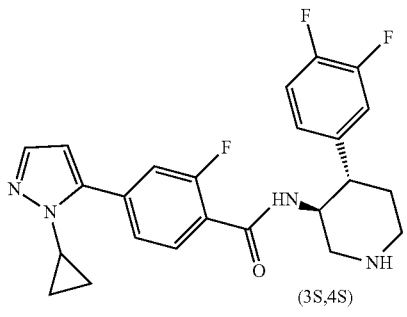 [SMILES: O=C(N[C@@H]1CNCC[C@H]1c1ccc(F)c(F)c1)c1ccc(-c2ccnn2C2CC2)cc1F] (3S,4S) | 4-(1-cyclopropyl-1H-pyrazol-yl)-N-((3S,4S)-4-(3,4-difluorophenyl)piperidin-3-yl)-2-fluorobenzamide |
| VII-29 | 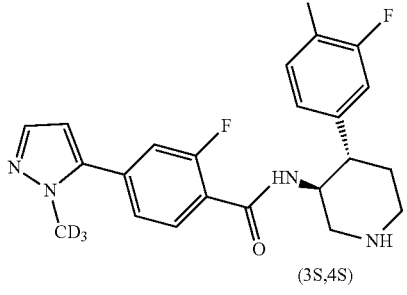 (3S,4S) | 4-(1-(methyl-d3)-1H-pyrazol-yl)-N-((3S,4S)-4-(3,4-difluorophenyl)piperidin-3-yl)-2-fluorobenzamide | and optical isomers of the above compounds; or pharmaceutically acceptable salt or solvate of the above compounds.

As a further preference, the polyfluoro-substituted aromatic heterocyclic derivative includes:

VII-30

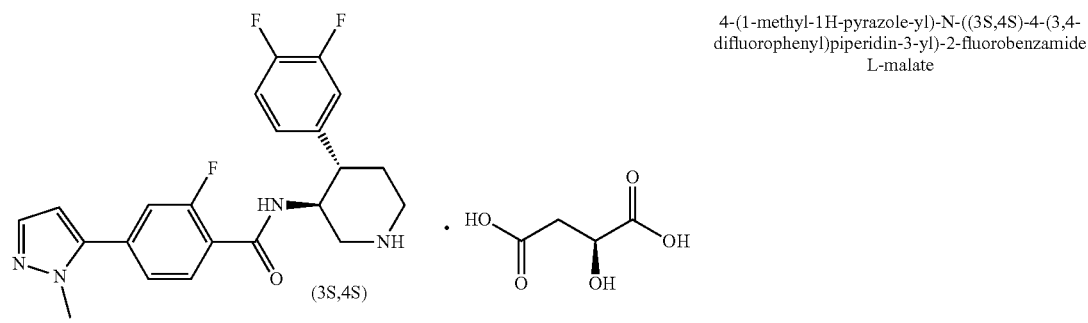

4-(1-methyl-1H-pyrazole-yl)-N-((3S,4S)-4-(3,4-difluorophenyl)piperidin-3-yl)-2-fluorobenzamide L-malate

VII-31

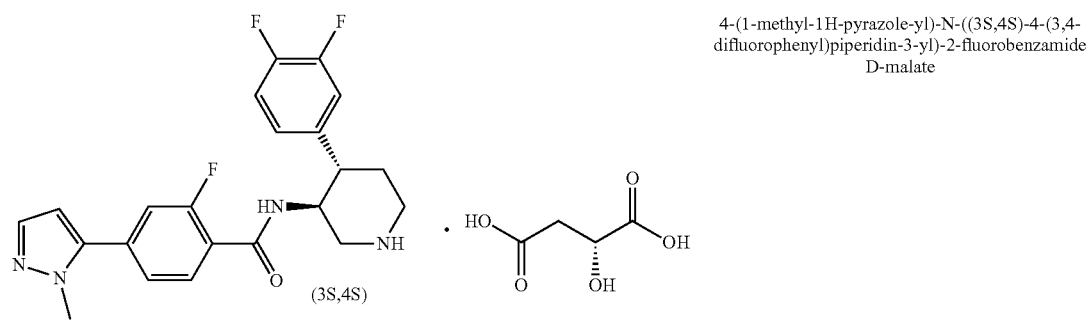

4-(1-methyl-1H-pyrazole-yl)-N-((3S,4S)-4-(3,4-difluorophenyl)piperidin-3-yl)-2-fluorobenzamide D-malate

VII-32

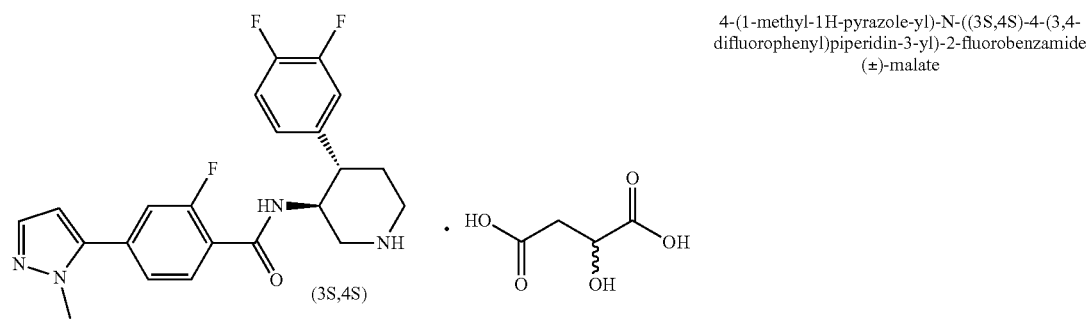

4-(1-methyl-1H-pyrazole-yl)-N-((3S,4S)-4-(3,4-difluorophenyl)piperidin-3-yl)-2-fluorobenzamide (±)-malate

VII-33

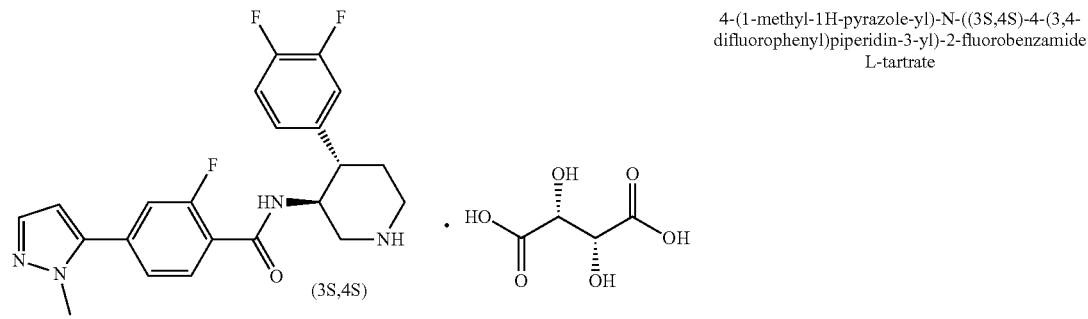

4-(1-methyl-1H-pyrazole-yl)-N-((3S,4S)-4-(3,4-difluorophenyl)piperidin-3-yl)-2-fluorobenzamide L-tartrate VII-34 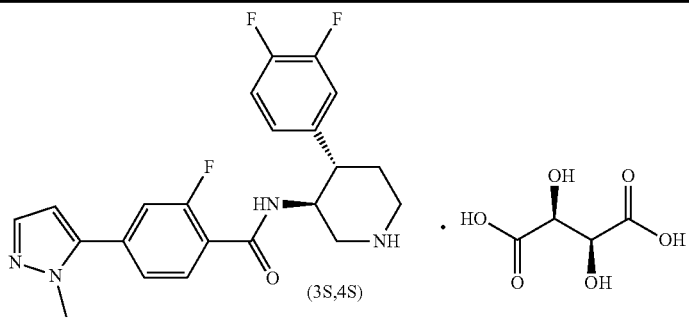

4-(1-methyl-1H-pyrazole-yl)-N-((3S,4S)-4-(3,4-difluorophenyl)piperidin-3-yl)-2-fluorobenzamide D-tartrate VII-35 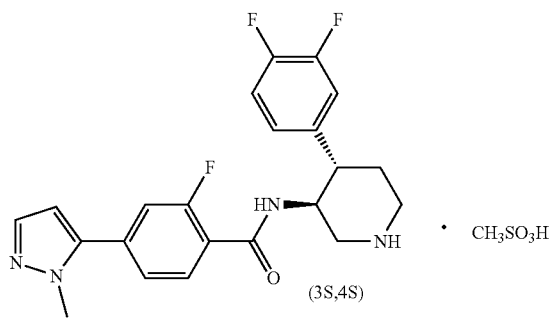

4-(1-Methyl-1H-pyrazole-yl)-N-((3S,4S)-4-(3,4-difluorophenyl)piperidin-3-yl)-2-fluorobenzamide methanesulfonate VII-36 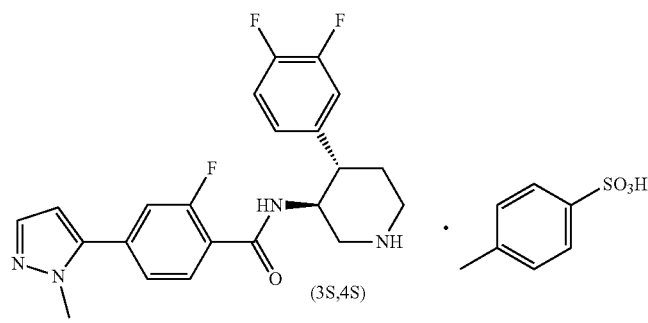 [SMILES: Cn1nccc1-c1ccc(C(=O)N[C@@H]2CNCC[C@H]2c2ccc(F)c(F)c2)c(F)c1 ; Cc1ccc(S(=O)(=O)O)cc1]

4-(1-methyl-1H-pyrazole-yl)-N-((3S,4S)-4-(3,4-difluorophenyl)piperidin-3-yl)-2-fluorobenzamide p-toluene sulfonate VII-37 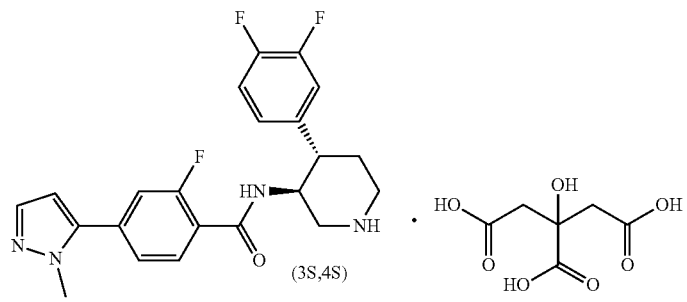 [SMILES: Cn1nccc1-c1ccc(C(=O)N[C@@H]2CNCC[C@H]2c2ccc(F)c(F)c2)c(F)c1 ; O=C(O)CC(O)(CC(=O)O)C(=O)O]

4-(1-methyl-1H-pyrazole-yl)-N-((3S,4S)-4-(3,4-difluorophenyl)piperidin-3-yl)-2-fluorobenzamide citrate or other optical isomers of the above compounds; or pharmaceutically acceptable solvate of the above compounds.

Description of terms: the term "aryl" as used herein refers to an all-carb monocyclic or condensed polycyclic group of 4 to 12 carbon atoms and has a fully conjugated pi-electron system. Non-limiting embodiments of aryl are: phenyl, naphthyl and anthracenyl. The aryl can be unsubstituted or substituted. The substituent of the aryl is selected from a group consisting of halogen, nitro, amino, cyano, hydroxy, $C_1$-$C_6$ alkyl, $C_1$-$C_6$ alkoxy, halogenated $C_1$-$C_6$ alkyl, halogenated $C_1$-$C_6$ alkoxy, $C_3$-$C_6$ cycloalkyl and halogenated $C_3$-$C_6$ cycloalkyl.

The term "heterocyclic aryl" as used herein refers to an unsaturated carboatomic ring of 4 to 12 annular atoms, wherein one or more carbons are replaced by a heteroatom such as oxygen, nitrogen, sulfur, etc., and also has a fully conjugated pi-electron system. The heterocyclic aryl may be a monocyclic ring or a bicyclic ring which is fused by two rings. Specific heterocyclic aryl may be: pyridyl, pyrimidinyl, pyrazinyl, isoxazolyl, isothiazolyl, pyrazolyl, thiazolyl, oxazolyl, imidazolyl, and the like. The heterocyclic aryl may be unsubstituted or substituted. The substituent of the heterocyclic aryl is selected from a group consisting of halogen, nitro, amino, cyano, hydroxy, $C_1$-$C_6$ alkyl, $C_1$-$C_6$ alkoxy, halogenated $C_1$-$C_6$ alkyl, halogenated $C_1$-$C_6$ alkoxy, $C_3$-$C_6$ cycloalkyl and halogenated $C_3$-$C_6$ cycloalkyl.

The term "cycloalkyl" as used herein refers to a saturated monocyclic carbon ring having from 3 to 8 carbon atoms unless a different number of atoms are indicated. For example, "cycloalkyl" includes cyclopropyl, cyclobutyl, cyclopentyl, cyclohexyl, cycloheptyl and cyclooctyl. "Cycloalkyl" also includes substituted cycloalkyl. The cycloalkyl can also be optionally substituted on any available carbon by one or more substituents selected from a group consisting of alkoxy, halogen and haloalkyl, such as perfluoroalkyl.

The term "alkoxy" as used herein refers to an —O-alkyl group. Embodiments of "alkoxy" as used herein include, but not limited to, methoxy, ethoxy, n-propoxy, isopropoxy, n-butoxy and tert-butoxy. "Alkoxy" also includes substituted alkoxy. The alkoxy can be optionally substituted one or more times by a halogen.

The term "halogen" as used herein refers to fluorine, chlorine, bromine or iodine, and is preferably fluorine or chlorine.

The term "pharmaceutically acceptable derivative" refers to a salt and solvate of the selected compounds.

The term "solvate" as used herein refers to a variable stoichiometric complex formed by a solute (for example, a compound of the formula I, formula I', formula II-1, formula II-2, formula II-3, etc. of the present invention) and a solvent. For the purposes of the present invention, the solvent does not interfere with the biological activity of the solute. Embodiments of suitable solvents include, but not limited to, water, methanol, ethanol, and acetic acid. The solvent used is preferably a pharmaceutically acceptable solvent. Suitable pharmaceutically acceptable solvents include, but not limited to, water, ethanol, and acetic acid. More preferably, the solvent used is water.

The present invention can be used to prepare salts of the substituted heterocyclic nitrogen compounds of the present invention by methods well known to the skilled in the art. The salts can be an organic acid salt, a mineral acid salt and the like, and the organic acid salt includes a citrate, a fumarate, an oxalate, a malate, a lactate, a camphor sulfonate, a tosilate, a mesylate, a metal triflates, a benzene sulfonate and a p-toluene sulfonate, etc.; and the inorganic acid salt includes a hydrohalide, a sulfate, a phosphate and a nitrate, etc. For example, methanesulfonate, triflate can be formed with a lower alkyl sulfonic acid, such as methanesulfonic acid, trifluoromethanesulfonic acid, etc.; benzene sulfonate, p-toluene sulfonate can be formed with arylsulfonic acid such as benzenesulfonic acid or p-toluenesulfonic acid, etc.; corresponding salts can be formed with organic carboxylic acids such as acetic acid, fumaric acid, tartaric acid, oxalic acid, maleic acid, malic acid, succinic acid or citric acid, etc, and glutamate or aspartate can be formed with amino acid, such as glutamic acid or aspartic acid. A corresponding salt can also be formed with a mineral acid such as a haloid acid (e.g. hydrofluoric acid, hydrobromic acid, hydroiodic acid, hydrochloric acid), nitric acid, carbonic acid, sulfuric acid or phosphoric acid, etc.

A second object of the present invention is to provide a pharmaceutical composition, wherein, the pharmaceutical composition includes at least one active ingredient and one or more pharmaceutically acceptable carriers or excipients, the active ingredient can be any one or more of the polyfluoro-substituted aromatic heterocyclic derivative of the structure as represented by the formula I and the formula I' of the present invention, and a preferred compound thereof, an optical isomer of the compound, a pharmaceutically acceptable salt of the compound or its optical isomerism, and a solvate of the compound or an optical isomer thereof.

The carrier includes one or more of conventional diluents, excipients, fillers, binders, wetting agents, disintegrants, absorption enhancers, surfactants, adsorption carriers, lubricants, and the like in the pharmaceutical field, and a flavoring agent, a sweetener, or the like can be added if necessary. The medicament of the present invention can be prepared into various forms such as tablets, powders, granules, capsules, oral liquids and injectable preparations, and the medicaments of the above various dosage forms can be prepared according to a conventional method in the pharmaceutical field.

The present application further provides an application of the compound of formula I and formula I', an optical isomer thereof, and a pharmaceutically acceptable salt or solvate thereof for preparation of an antitumour drug. The tumour is breast cancer, sarcoma, lung cancer, prostate cancer, colon cancer, rectal cancer, kidney cancer, pancreatic cancer, blood cancer, neuroblastoma, glioma, head cancer, neck cancer, thyroid cancer, liver cancer, ovarian cancer, vulvar cancer, cervical cancer, endometrial cancer, testicular cancer, bladder cancer, esophageal cancer, gastric cancer, nasopharyngeal cancer, buccal cancer, oral cancer, gastrointestinal stromal tumour, skin cancer, multiple myeloma acute myeloid leukemia, chronic myeloid leukemia, or chronic lymphocytic leukemia.

The present invention further provides an application of the compound of the present invention or a pharmaceutically acceptable salt thereof for the preparation of an Akt inhibitor, in particular for the preparation of a treatment for cell proliferative diseases. The cell proliferative diseases include cancer. In other words, the present invention provides an application of a substituted nitrogen heterocyclic compound or a pharmaceutically acceptable salt thereof, alone or in combination with other drugs, for the treatment of a proliferative disease such as cancer. Antineoplastic agents which can be used in combination with the compound provided in the present invention or a pharmaceutically acceptable salt thereof include, but not limited to, at least one of the following classes: mitotic inhibitors (such as vinblastine, vindesine, and vinorelbine), tubulin decomposition inhibitors (such as taxol), antimetabolites (such as cisplatin, carboplatin and cyclophosphamide); antimetabolites (such as 5-fluorouracil, tegafur, methotrexate, cytarabine and hydroxyl urea), insertable antibiotics (such as arezzo, mitomycin and bleomycin), enzymes (such as aspartate); topoisomerase inhibitors (such as etoricin and camptothecin), biological response regulation Agents (such as interferon); proteasome inhibitors (such as bortezomib), and tumour immune related drugs (PD-1 antibody drugs, CTLA-4 antibody drugs).

The inventors of the present invention has confirmed by repeated experiments that the compound of the present invention has a significant inhibitory effect on Akt1, and exhibits potent proliferation inhibitory activity against tumour cell lines such as human ovarian cancer cell line (OVCAR-8), human breast cancer cell line (MCF7), human kidney cancer cell line (786-O), colon cancer cell line (HCT116), and human myeloma cell line (CEM-C1), etc.

DESCRIPTION OF PREFERRED EMBODIMENTS

The implements of the present invention will be described below by way of embodiments, and those skilled in the art will understand that modifications and substitutions of the corresponding technical features in accordance with the teachings of the prior art are still within the scope of the invention as claimed.

A First Embodiment: Synthesis of Intermediate 4Aa

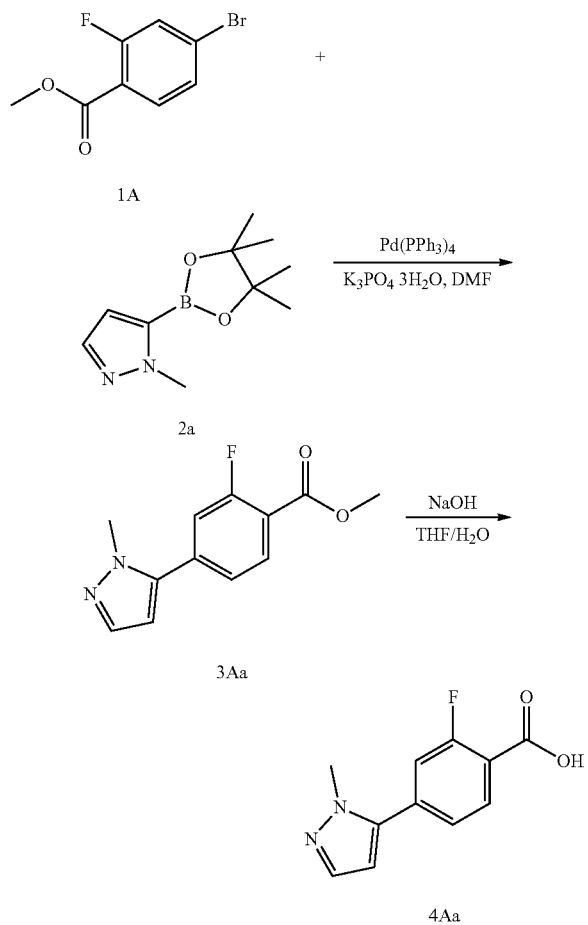

Step 1: 2-fluoro-4-methyl-bromobenzoate 1A (2.3 g, 10 mmol) tetrakis(triphenylphosphine)palladium (1.15 g, 1 mmol), 1-methyl-1H-pyrazole-5-boronic acid pinacol ester 2a (2.5 g, 12 mmol) and potassium phosphate trihydrate (4.0 g, 15 mmol) were added into a 100 ml three-necked bottle containing 50 mL of DMF in sequence under nitrogen protection and the reaction was placed at 90° C. with fully stirring overnight. The reaction mixture was cooled to room temperature after the reaction completes, the reaction mixture was poured into 100 mL of water and was extracted three times with ethyl acetate, and combined the organic layers, after washing twice with saturated sodium chloride, anhydrous sodium sulphate was dried and concentrated under reduced pressure, and the obtained crude product was purified by silica gelcolumn chromatography to obtain a pale yellow solid 2.38 g of intermediate 3Aa with a yield 85%, $^1$H NMR 500 MHz, CDCl$_3$) δ 8.09-7.99 (m, 1H), 7.55 (d, J=1.9 Hz, 1H), 7.29 (dd, J=8.1, 1.6 Hz, 1H), 7.23 (dd, J=11.3, 1.6 Hz, 1H), 6.40 (d, J=1.9 Hz, 1H), 3.97 (s, 3H), 3.95 (s, 3H). ESI(M+H)$^+$=235.

Step 2: the intermediate 3Aa (2.38 g, 10 mmol) was dissolved in 20 ml of tetrahydrofuran, 10 mL of a 6N aqueous sodium hydroxide solution was added thereto, the reaction was continued at room temperature for 6 hours, and the organic solvent was removed under reduced pressure. 10 mL of water was added to the remaining reaction mixture, and the mixture was washed twice with dichloromethane, the aqueous layer was adjusted to pH of about 3 with a 1N hydrochloric acid solution, a large amount of solid was precipitated, filtered, and the filter cake was washed once with water and dried to obtain 1.9 g of white solid 4Aa with a yield 86%, $^1$H NMR (500 MHz, DMSO) δ 13.46 (s, 1H), 8.03-7.87 (m, 1H), 7.55 (d, J=11.8 Hz, 1H), 7.51 (d, J=1.5 Hz, 1H), 7.49 (d, J=8.1 Hz, 1H), 6.58 (d, J=1.5 Hz, 1H), 3.92 (s, 3H). ESI(M+H)$^+$=221.

A Second Embodiment: Synthesis of Intermediate 4Aa-1

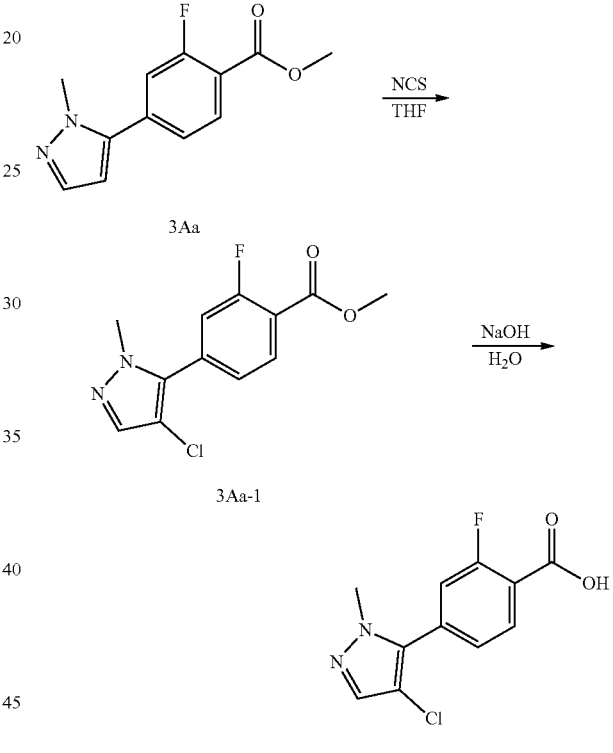

Step 1: the intermediate 3Aa (1.2 g, 5 mmol) was dissolved in 20 ml of tetrahydrofuran, and NCS (n-chlorosuccinimide) (348 mg, 6 mmol) was slowly added to thereto to react at room temperature for 5 hours, then an organic solvent was removed under reduced pressure, 10 mL of water was added to the remaining reaction mixture, and the mixture was extracted twice with methylene chloride to combine the organic layer, the organic layer was washed twice with saturated sodium chloride and dried over anhydrous sodium sulphate, and the obtained crude product was purified by silica gel column chromatography to yield pale yellow solid, and the pale yellow solid was dried to obtain 1.07 g of white solid 3Aa-1.

Step 2: the intermediate 3Aa-1 (1.2 g, 5 mmol) was dissolved in 20 ml of tetrahydrofuran, 10 mL of a 6N aqueous sodium hydroxide solution was added to thereto, the reaction was continued at room temperature for 6 hours, and the organic solvent was removed under reduced pressure. 10 mL of water was added to the remaining reaction mixture, and the mixture was washed twice with dichloromethane, the aqueous layer was adjusted to a pH of about 3 with a 1N hydrochloric acid solution with precipitating and filtering a large amount of solid, and the filter cake was washed once with water and dried to obtain 1.14 g of white solid 4Aa-1 with yield 90%, ESI(M+H)$^+$=255.

A Third Embodiment: Synthesis of Intermediate 4Ab

1A

+

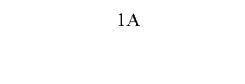

2b

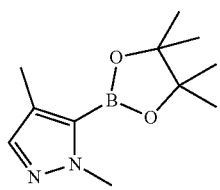

3Ab

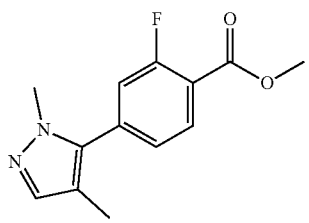

4Ab

A Forth Embodiment: Synthesis of Intermediate 4Ac

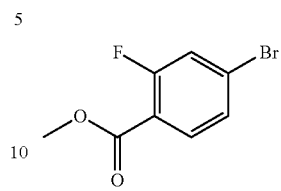

1A

+

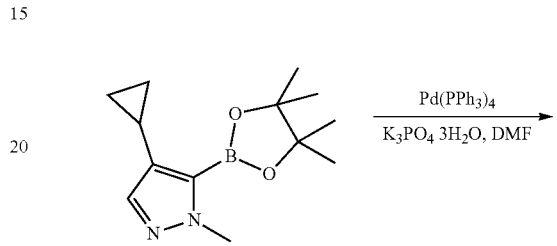

2c

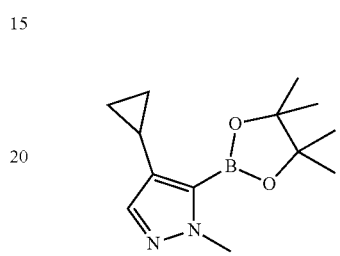

3Ac

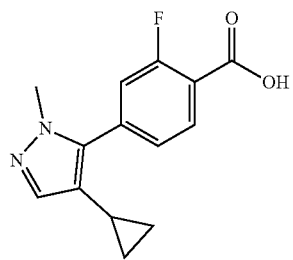

4Ac

Referring to the steps 1 and 2 of the first embodiment, 1-methyl-1H-pyrazole-5-boronic acid pinacol ester 2a was substituted with 1,4-dimethyl-1H-pyrazole-5-boronic acid pinacol ester 2b (2.66 g, 12 mmol) and 2-fluoro-4-bromobenzoic acid methyl ester 1A (2.3 g, 10 mmol) was used as a raw material to obtain 1.58 g of white solid 4Ab with a yield of 56% (two steps), ESI(M+H)$^+$=235.

Referring to the steps 1 and 2 of the first embodiment, 1-methyl-1H-pyrazole-5-boronic acid pinacol ester 2a was substituted with 1-methyl-4-cyclopropyl-1H-pyrazole-5-boronic acid pinacol ester 2c (2.98 g, 12 mmol), and methyl 2-fluoro-4-bromobenzoate 1A (2.3 g, 10 mmol) was used as a raw material to obtain 1.34 g of white solid 4Ac with a yield of 43% (two steps), ESI(M+H)$^+$=261.

A Fifth Embodiment: Synthesis of Intermediate 4Aa-2

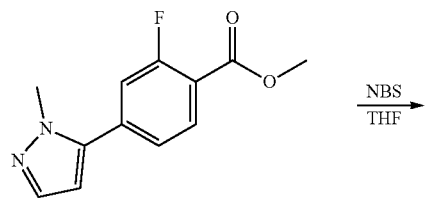

3Aa

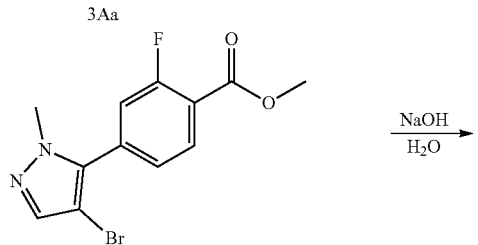

3Aa-2

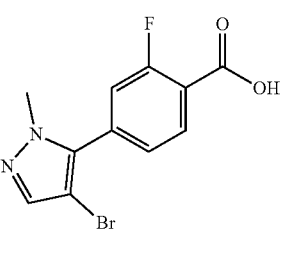

4Aa-2

Referring to steps 1 and 2 of the second embodiment, NCS was substituted with NBS (1.07 g, 6 mmol) and the intermediate 3Aa (1.2 g, 5 mmol) was used as a raw material to obtain 1.16 g of white solid 4Aa-2 with a yield of 78% (two steps), ESI(M+H)⁺=299.

A Sixth Embodiment: Synthesis of Intermediate 4Ad

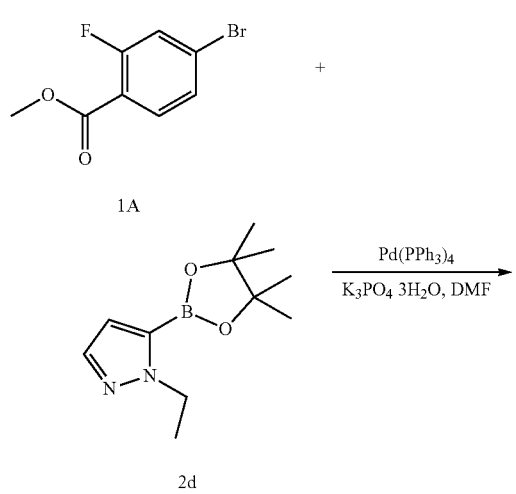

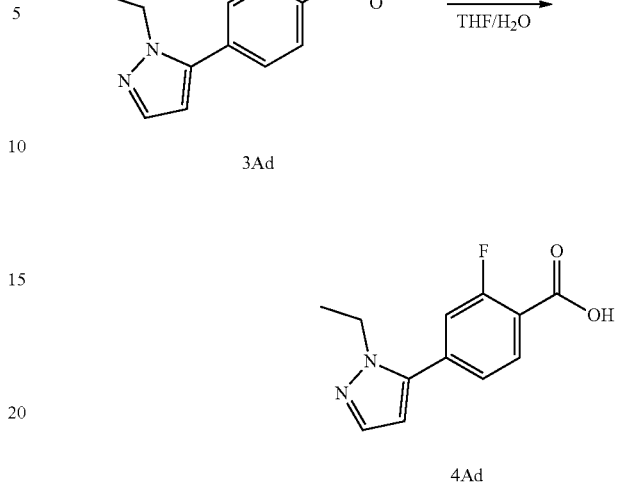

3Ad

4Ad

Referring to steps 1 and 2 of the first embodiment, 1-methyl-1H-pyrazole-5-boronic acid pinacol ester 2a was substituted with 1-ethyl-1H-pyrazole-5-boronic acid pinacol ester 2d (2.48, 12 mmol), methyl 2-fluoro-4-bromobenzoate 1A (2.3 g, 10 mmol) was used as a raw material to obtain 1.52 g of white solid 4Ad with a yield of 64.95% (two steps), ESI(M+H)⁺=235.

A Seventh Embodiment: Synthesis of Intermediate 4Ae

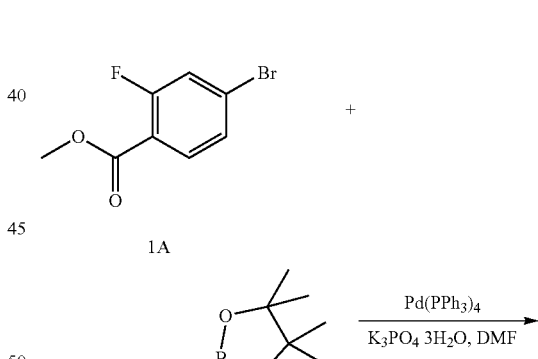

3Ae

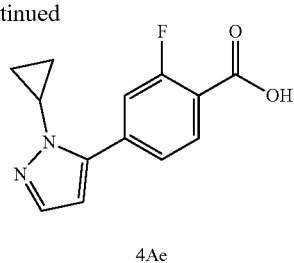

4Ae

Referring to steps 1 and 2 of the first embodiment, 1-methyl-1H-pyrazole-5-boronic acid pinacol ester 2a was substituted with 1-cyclopropyl-1H-pyrazole-5-boronic acid pinacol ester 2e (2.81 g, 12 mmol), and 2-fluoro-4-bromobenzoic acid methyl ester 1A (2.3 g, 10 mmol) was used as a raw material to obtain 1.30 g of white solid 4Ae with a yield 52% (two steps), ESI(M+H)$^+$=247.

An Eighth Embodiment: Synthesis of Intermediate 4Ba

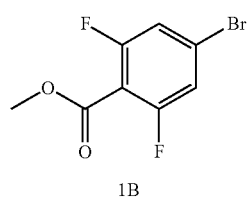

1B

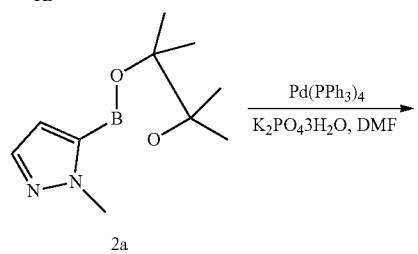

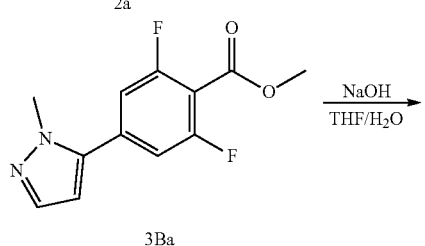

4Ba

Referring to steps 1 and 2 of the first embodiment, methyl 2-fluoro-4-bromobenzoate 1A was substituted with 4-bromo-2,6-difluoro-benzoic acid methyl ester 1B (2.49 g, 10 mmol) to obtain 1.63 g of white solid 4Ba with a yield of 57% (two steps), ESI(M+H)$^+$=239.

A Ninth Embodiment: Synthesis of Intermediate 4Ca

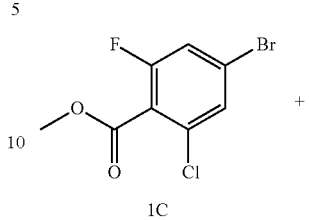

1C

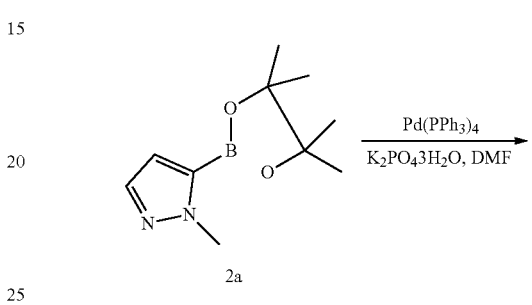

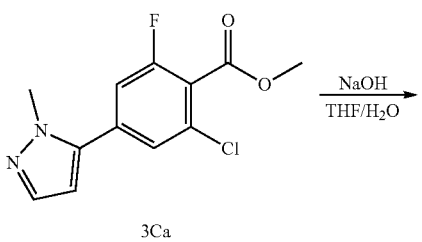

3Ca

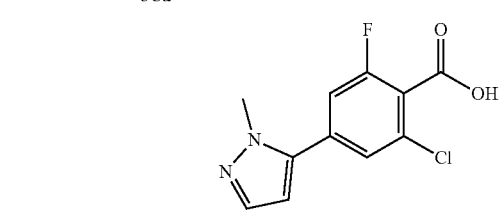

4Ca

Referring to steps 1 and 2 of the first embodiment, methyl 2-fluoro-4-bromobenzoate 1A was substituted with 4-bromo-2-chloro-6-fluoro-benzoic acid methyl ester 1C (2.52 g, 10 mmol) to obtain white solid 4Ca with a yield of 64% (two steps), ESI(M+H)$^+$=255.

A Tenth Embodiment: Synthesis of Intermediate 4Da

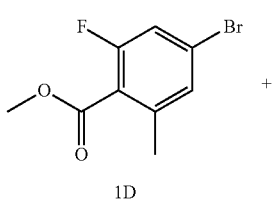

1D

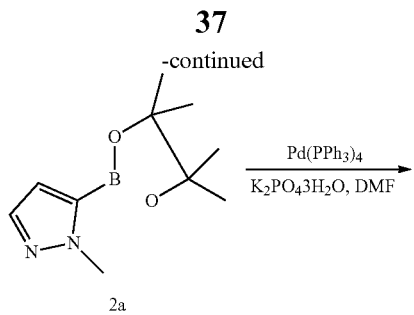
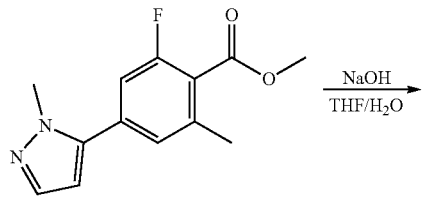

Referring to steps 1 and 2 of the first embodiment, methyl 2-fluoro-4-bromobenzoate 1A was substituted with methyl 4-bromo-2-fluoro-6-methylbenzoate 1D (2.32 g, 10 mmol) to obtain white solid 4 Da with a yield 57% (two steps), ESI(M+H)$^+$=235.

An Eleventh Embodiment: Synthesis of Intermediate 4Ea

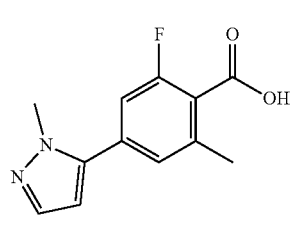
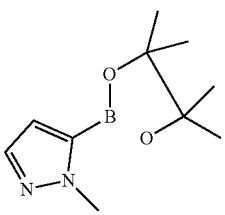
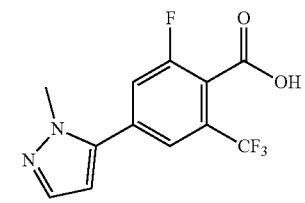

Referring to steps 1 and 2 of the first embodiment, methyl 2-fluoro-4-bromobenzoate 1A was substituted with methyl 4-bromo-2-fluoro-6-trifluoromethylbenzoate 1E (2.99 g, 10 mmol) to obtain white solid 4Ea with a yield of 61% (two steps), ESI(M+H)$^+$=289.

A Twelfth Embodiment: Synthesis of Intermediate 4Fa

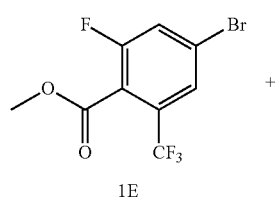
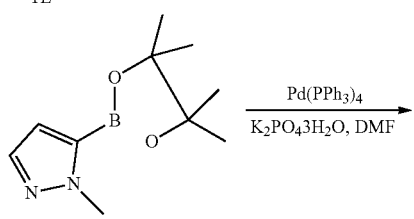
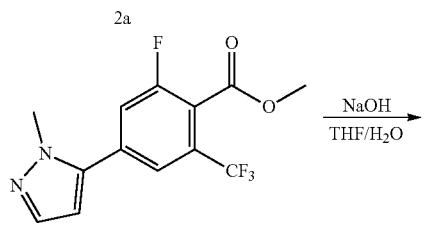
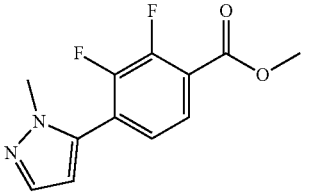
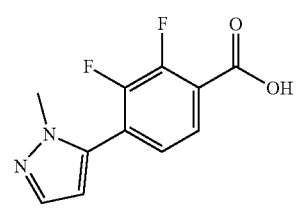

Referring to steps 1 and 2 of the first embodiment, methyl 2-fluoro-4-bromobenzoate 1A was substituted with methyl 4-bromo-2,3-difluorobenzoate 1F (2.49 g, 10 mmol) to obtain white solid 4Fa with a yield of 60% (two steps), ESI(M+H)$^+$=239.

A Thirteenth Embodiment: Synthesis of Intermediate 4Ga

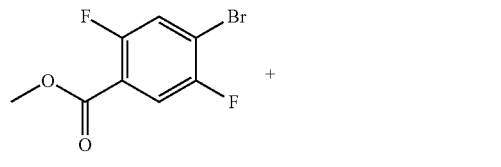

1G

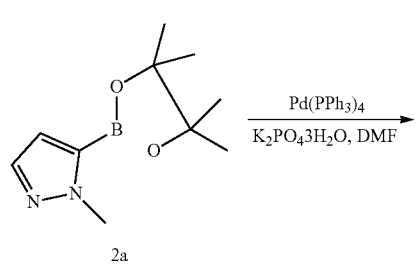

3Ga

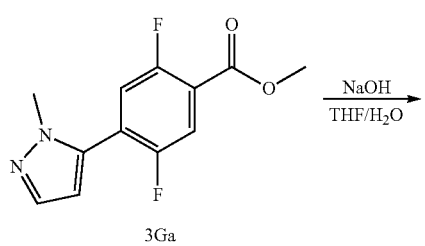

4Ga

Referring to steps 1 and 2 of the first embodiment, methyl 2-fluoro-4-bromobenzoate 1A was substituted with 4-Bromo-2,5-difluoro-benzoic acid methyl ester 1G (2.49 g, 10 mmol) to obtain white solid 4Ga with a yield 58% (two steps), ESI(M+H)$^+$=239.

A Fourteenth Embodiment: Synthesis of Intermediate 8

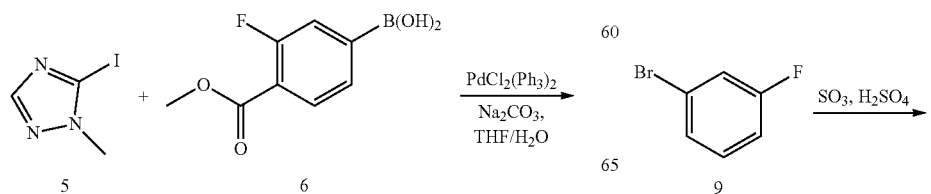

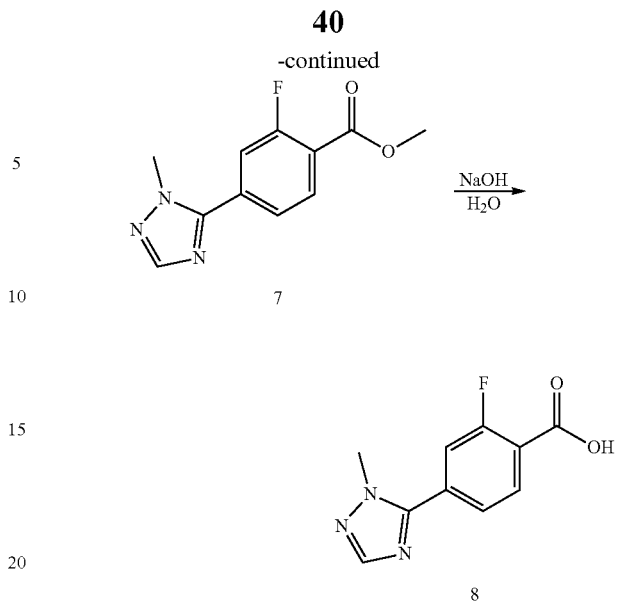

Step 1: 5-iodo-1-methyl-1 hydrogen-1,2,4 triazole 5 (416 mg, 2.0 mmol), 3-fluoro-4-methoxycarbonylbenzeneboronic acid 6 (475 mg, 2.40 mmol), double triphenylphosphine palladium chloride (63.8 mg, 0.10 mmol) was dissolved in tetrahydrofuran, saturated aqueous sodium carbonate (2.00 mmol) was added to thereto, and microwave reaction was performed (138° C., 28 min) under microwave atmosphere. The reaction mixture was cooled to room temperature after the reaction completes, the reaction mixture was poured into 100 mL of water and was extracted three times with ethyl acetate, and combined the organic layers, after washing twice with sodium chloride, anhydrous sodium sulphate was dried and concentrated under reduced pressure, and the obtained crude product was subjected to silica gel column chromatography to obtain intermediate 7 with a yield of 80, ESI (M+H)+=236.

Step 2: Intermediate 7 (2.36 g, 10 mmol) was dissolved in 20 ml of tetrahydrofuran, 10 mL of aqueous 6N sodium hydroxide solution was added to thereto, and the reaction was continued at room temperature for 6 hours, and the organic solvent was removed under reduced pressure. 10 mL of water was added to the remaining reaction mixture, and the mixture was washed twice with dichloromethane, the aqueous layer was adjusted to pH of about 3 with a 1N hydrochloric acid solution, a large amount of solid was precipitated, filtered, and the filter cake was washed once with water and dried to obtain 1.9 g of white solid 8 with a yield 85%, ESI(M+H)+=222.

A Fifteenth Embodiment: Synthesis of Intermediate 11

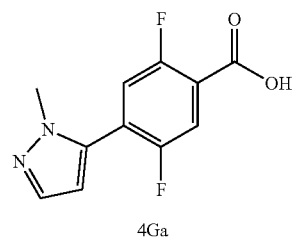

9

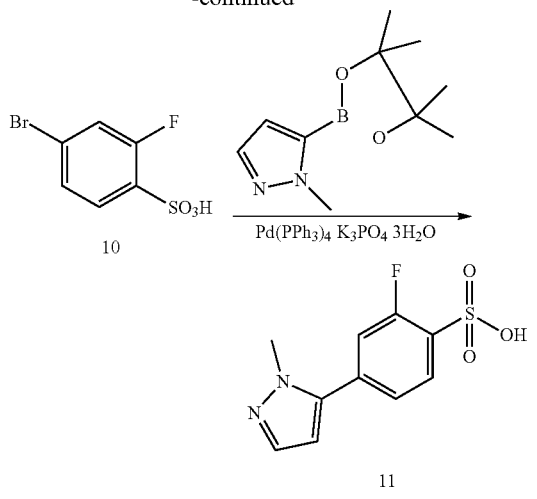

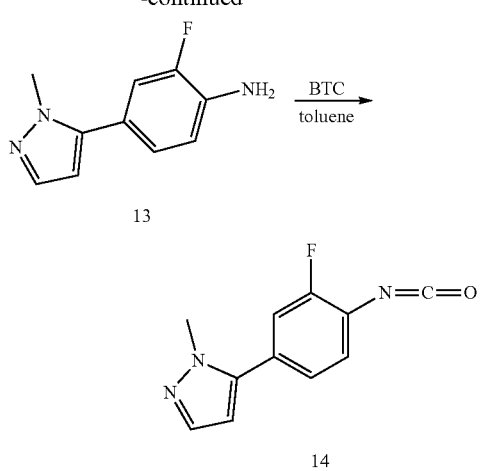

Step 1: under the protection of nitrogen, 1-bromo-3-fluorobenzene 9 was used as a solvent. fuming sulphuric acid (20% $SO_3$) was added dropwise to the system under ice-cooling conditions, then the system was transferred to normal temperature and heated to 110° C. After the reaction was completed, the reaction mixture was quenched with ice water, and extracted with ethyl acetate three times, the organic layer was combined and washed with saturated sodium chloride, and the obtained crude product was subjected to silica gel column chromatography to obtain white solid 10 with a yield of 37%.

Step 2: under the protection of nitrogen, the compound 10 (2.53 g, 10 mmol), tetrakis(triphenylphosphine)palladium (1.15 g, 1 mmol), 1-methyl-1H-pyrazole-5-boronic acid pinacol ester 2a (2.31 g, 12 Methyl) and potassium phosphate trihydrate (7.5 g, 15 mmol) were sequentially added to a 100 ml three-necked bottle containing 50 mL of DMF, and the reaction system was placed at 90° C. and stirred thoroughly overnight. After the reaction completes and was cooled to room temperature, the reaction solution was poured into 100 mL of water, extracted three times with ethyl acetate, the organic layer was combined, washed twice with saturated sodium sulfate and dried over anhydrous sodium sulfate. anhydrous sodium sulphate was dried and concentrated under reduced pressure, and the obtained crude product was subjected to silica gel column chromatography to obtain the 2.38 g of intermediate 11 with a yield of 92%, ESI(M+H)$^+$=257.

A Sixteenth Embodiment: Synthesis of Intermediate 14

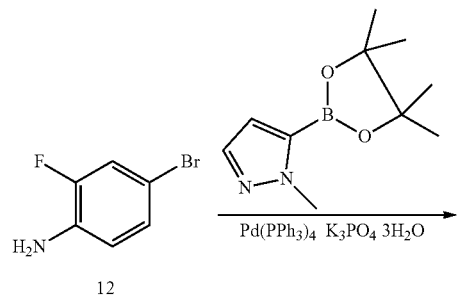

Step 1: under the protection of nitrogen, 4-bromo-2-fluoroaniline 12 (1.88 g, 10 mmol), tetrakis(triphenylphosphine)palladium (1.15 g, 1 mmol), 1-methyl-1H-pyrazole-5-boronic acid pinacol ester 2a (2.31 g, 12 mmol) and potassium phosphate trihydrate (7.5 g, 15 mmol) were sequentially added to a 100 ml three-necked bottle containing 50 mL of DMF, and the reaction system was placed at 90° C. and stirred thoroughly overnight. After the reaction completed and was cooled to room temperature, the reaction solution was poured into 100 mL of water, extracted three times with ethyl acetate, the organic layer was combined, washed twice with saturated sodium chloride and dried over anhydrous sodium sulfate. anhydrous sodium sulphate was dried and concentrated under reduced pressure, and the obtained crude product was subjected to silica gel column chromatography to obtain the 1.0 g of pale yellow solid 13 with a yield of 52%, ESI(M+H)$^+$=192.

Step 2: under the protection of nitrogen, the intermediate 13 (191 mg, 1 mmol), and triethylamine (202 mg, 2 mmol) were dissolved in 50 ml of toluene, and the phosgene (BTC) was slowly added dropwise to the toluene solution under ice bath, after the dropwise addition was completed, the mixture was heated to reflux, and the reaction was monitored by TLC, after the reaction completed, 30 ml of 1N $NaHCO_3$ solution was added to the reaction system, and the mixture was extracted three times with ethyl acetate, the organic layer was combined, washed once with anhydrous sodium chloride, anhydrous sodium sulphate was dried and the solvent was recovered under reduced pressure to obtain 92 mg of yellow oily liquid 14 with a yield of 45%, ESI(M+H)$^+$=218.

A Seventeenth Embodiment: Synthesis of Intermediate 19

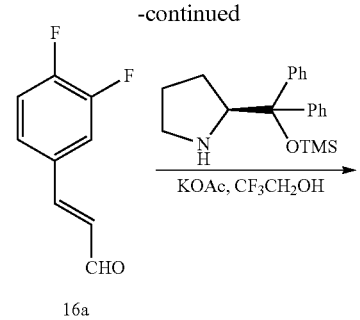

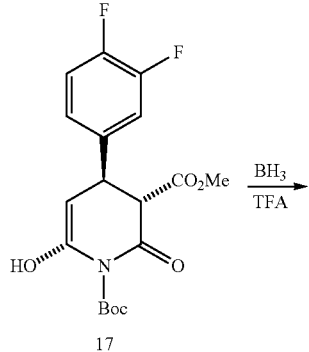

Step 1: methyl 3-((tert-butyloxycarbonyl)amino)-3-oxo-propanoate 15 (0.25 mmol, 1 equiv), 3,4-difluorocinnamaldehyde 16a (0.3 mmol, 1.2 equiv), ((S)-(−)-α,α-diphenyl-2-pyrrolemethyl)trimethylsilyl ether (0.05 mmol, 0.2 equiv), and potassium acetate (0.25 mmol, 1 equiv) were dissolved in 1 ml of 2,2,2-trifluoroethanol solution, the reaction mixture was stirred at room temperature overnight, after the reaction was completed, the mixture was quenched with water and then extracted three times with ethyl acetate, the organic layer was combined and washed with saturated sodium chloride, anhydrous sodium sulphate was dried and the obtained crude product was subjected to silica gel column chromatography to obtain pale yellow oily liquid 17 with a yield of 63%.

Step 2: under the protection of nitrogen, the intermediate 17 was dissolved in anhydrous THF, and borane in THF solution was slowly added dropwise to the reaction system at −74° C., after the addition was completed, the system was heated to −20° C., the reaction continues for 5 hours, and a saturated sodium carbonate solution was added to quench, the system was extracted three times with ethyl acetate, the organic layer was combined and washed with saturated sodium chloride, anhydrous sodium sulphate was dried and the obtained crude product was purified by silica gel column chromatography to obtain pale yellow solid 18 with a yield of 73%, ESI(M+H)$^+$=328.

Step 3: under the protection of nitrogen, the antimony trichloride and sodium periodate were dissolved in a solvent system of carbon tetrachloride:acetonitrile=1:1, and after stirring for 1 hour, the acetonitrile solution of the intermediate 18 was slowly added dropwise to the reaction system under ice bath, after the addition was completed, it was moved to normal temperature, after reacting for 7 hours, the reaction was quenched with water and extracted with ethyl acetate three times, the organic layer was combined and washed with saturated sodium chloride, anhydrous sodium sulphate was dried and the obtained crude product was purified by silica gel column chromatography to obtain white solid 19 with a yield of 83%, ESI(M+H)$^+$=342.

An Eighteenth Embodiment: Synthesis of Intermediate (±)23

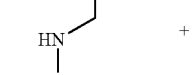

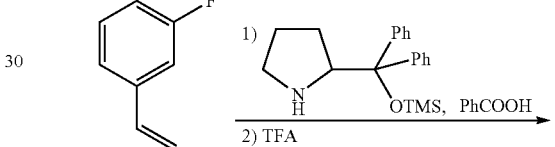

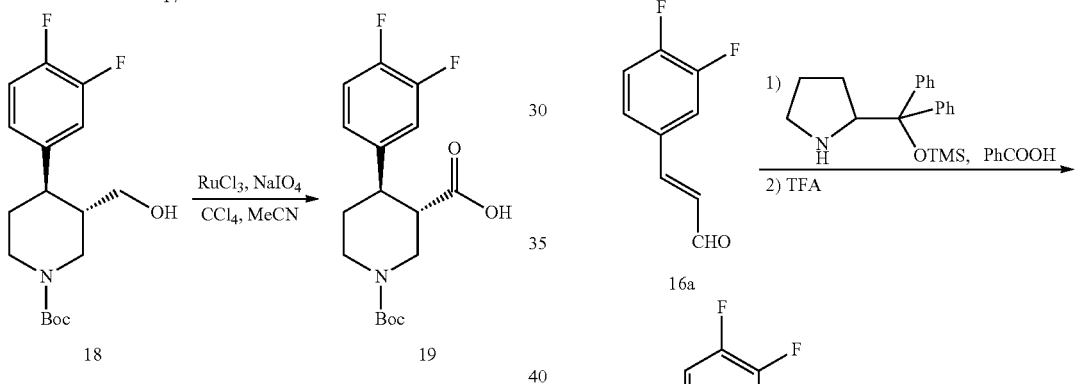

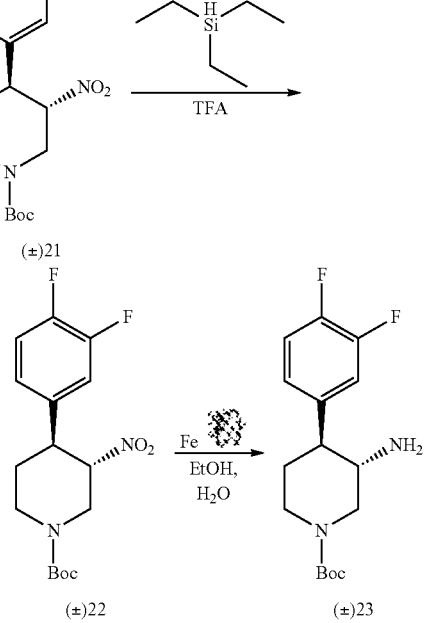

Step 1: tert-butyl 2-nitroethylcarbamate 20 (285 mg, 1.5 mmol), (α,α-diphenyl-2-pyrrolemethyl)trimethylsilyl ether (33 mg, 0.1 mmol) and benzene formic acid (25 mg, 0.2 mmol) were dissolved in 2 mL of re-distilled DCM, cooled to 0° C., slowly added 3,4-difluorocinnamaldehyde 16a (168 mg, 1 mmol), and stirred at room temperature overnight. After the reaction of the raw material completes, it was cooled to 0° C., and the DCM was evaporated from the reaction system and diluted to 10 mL, TFA (148 μL, 2 mmol) was slowly added dropwise, and stirred at room temperature for 5 h. The reaction was quenched by dropwise addition of 1N NaHCO$_3$ (10 mL) and continued stirring for 10 min and extracted with EtOAc (10 mL×3), the organic layer was combined and washed with saturated NaCl solution (20 mL×2), anhydrous Na$_2$SO$_4$ was dried, solvent was recovered under reduced pressure and the residue was purified by column chromatography (petroleum ether:EtOAc=30:1~10:1) to yield pale yellow solid (±) 21 (180 mg, 0.53 mmol) with a yield of 53%, ESI[M+Na]$^+$=363.

Step 2: the compound (±) 21 (1.84 g, 5.4 mmol) and triethylsilane (1.8 mL, 11 mmol) were dissolved in 25 mL of DCM, and TFA (3.7 mL, 50 mmol) was slowly added dropwise under ice bath, and the reaction was carried out at room temperature overnight. After the raw material was completely reacted, the reaction was quenched with a saturated NaHCO$_3$ solution (50 mL), and the mixture was stirred for 10 min, extracted with DCM (20 mL×3), and the organic layer was combined and washed with saturated NaCl solution (20 mL×2), the solvent was recovered under reduced pressure to obtain an oily matter. The obtained residual oily matter and TEA (triethylamine, 1.4 mL, 10 mmol) were dissolved into 45 mL of THF, and Boc$_2$O acid anhydride (1.78 g, 8.2 mmol) was added in batches under ice bath, after the addition was completed, the reaction system was stirred at room temperature for 5 h. The THF was evaporated under reduced pressure and the residue was dissolved in 50 ml of EtOAc, it was washed with 0.5 N aqueous HCl solution (20 mL×2), saturated NaCl solution (20 mL×2), and dried over anhydrous Na$_2$SO$_4$ and solvent was recovered under reduced pressure, and the residue was purified by column chromatography to obtain a white solid (±) 22 (1.44 g, 4.2 mmol) with a yield of 78%, ESI(M+H)$^+$=343.

Step 3: the compound (±) 22 (1.44 g, 4.2 mmol), reduced iron powder (2.82 g, 50.4 mmol) and NH$_4$Cl (1.0 g, 16.8 mmol) were suspended in 40 mL of a mixed solution of EtOH and H$_2$O (v/v, 3:1), the mixture was heated to reflux for 5 h under mechanical stirring. After the reaction of the raw material completed, the mixture was filtered, and the filtrate was concentrated, the residue was dissolved in 50 mL of EtOAc, washed with saturated NaHCO$_3$ solution (20 mL×2) and saturated NaCl solution (20 mL×2), anhydrous Na$_2$SO$_4$ was dried, the solvent was recovered under reduced pressure and dried in vacuum to obtain an off-white solid (±) 23 (1.15 g, 3.7 mmol), with a yield of 88%, $^1$H NMR (500 MHz, CDCl$_3$) δ 7.15-7.09 (m, 1H), 7.05-7.01 (m, 1H), 6.97-6.93 (m, 1H), 4.45-4.09 (m, 2H), 2.92-2.67 (m, 2H), 2.56-2.43 (m, 1H), 2.38-2.29 (m, 1H), 1.76 (d, J=12.6 Hz, 1H), 1.71-1.57 (m, 1H), 1.48 (s, 9H). ESI(M+H)$^+$=313.

A Nineteenth Embodiment: Synthesis of Intermediate (3S,4S)-23

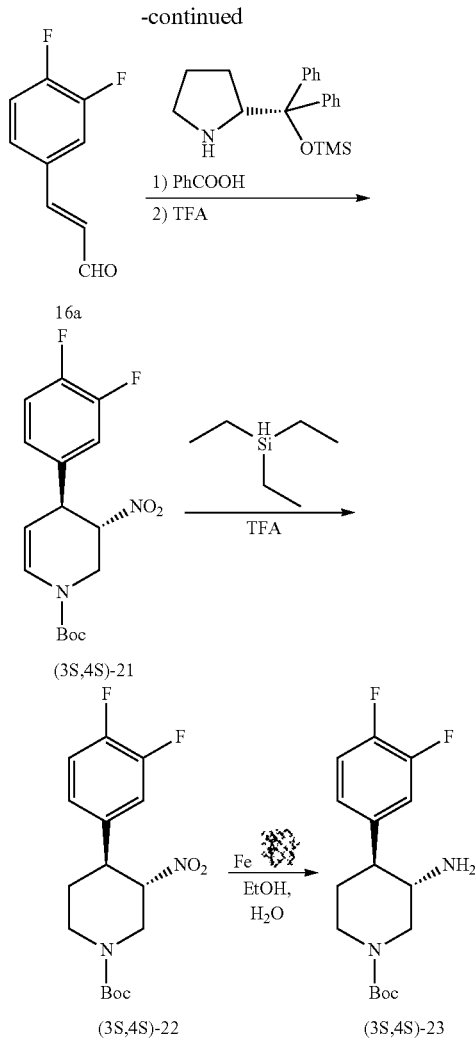

Referring to the steps 1, 2, and 3 of the eighteenth embodiment, (α,α-diphenyl-2-pyrrolemethyl)trimethylsilane was substituted with ((S)-(−)-α,α-diphenyl-2-pyrrolemethyl)trimethylsilyl ether, and 3,4-difluorocinnamaldehyde 16a (2.52 g, 15 mmol) was used as a raw material to obtain 1.64 g of an off-white solid (3S, 4S)-23 with a yield of 35% (three steps), ESI(M+H)$^+$=313.

Chiral analysis conditions: flow rate: 0.8 ml/min, mobile phase: 0.1% aqueous formic acid/methanol=1:4; ultraviolet: 254 nm; column temperature: 30° C.; injection amount: 5 μl; injection concentration: 1 mg/ml; chiral column model: Daicel OJ-RH CD-UG026. The analytical condition determines that the intermediate (3S, 4S)-22 has an ee=98%.

A Twentieth Embodiment: Synthesis of Intermediate (3R,4R)-23

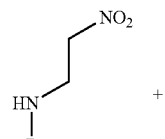

20

+

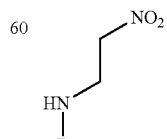

20

-continued

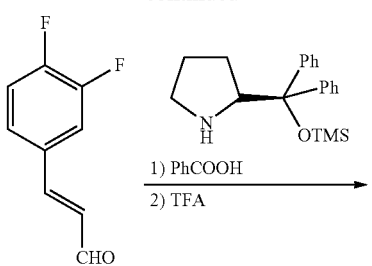

16a

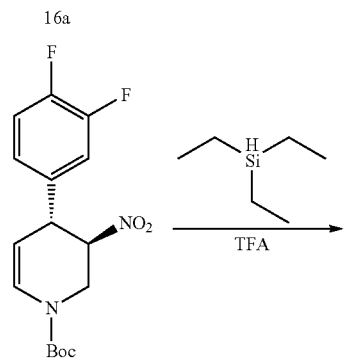

(3R,4R)-21

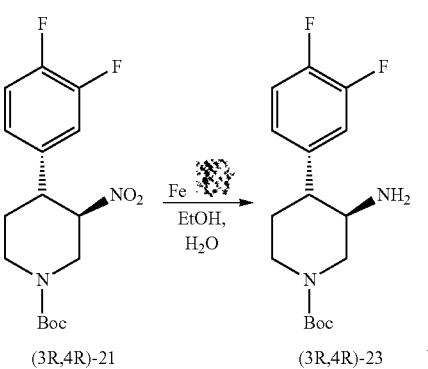

(3R,4R)-21    (3R,4R)-23

Referring to the steps 1, 2, and 3 of the eighteenth embodiment, (α,α-diphenyl-2-pyrrolemethyl)trimethylsilyl ether was substituted with ((R)-(−)-α,α-diphenyl-2-pyrrolemethyl)trimethylsilyl ether, and 3,4-difluorocinnamaldehyde 16a (2.52 g, 15 mmol) is used as a raw material to obtain 1.69 g of an off-white solid (3R, 4R)-23 with a yield of 36% (three steps), ESI(M+H)$^+$=313, and the ee of the intermediate (3R, 4R)-22 equals to 97% (analytical conditions are the same as the nineteenth embodiment).

A Twenty-First Embodiment: Synthesis of Intermediate 23b

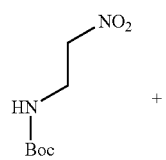

20

-continued

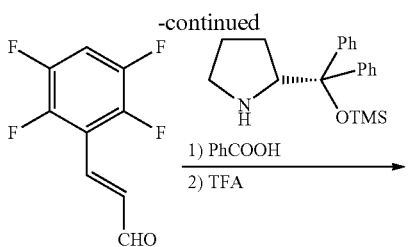

16c

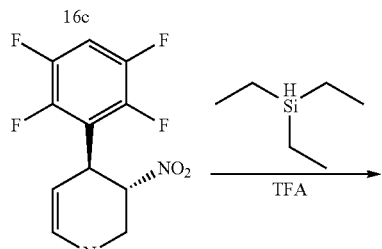

21c

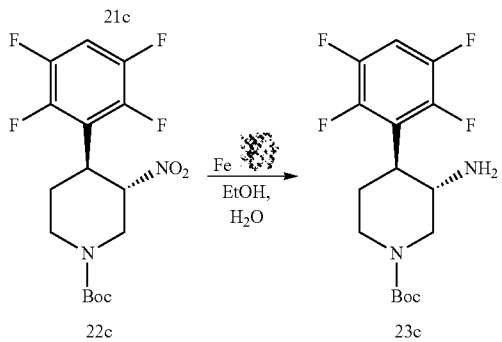

22c    23c

Referring to the steps 1, 2, and 3 of the nineteenth embodiment, the 3,4-difluorocinnamaldehyde in the step 1 was substituted with 3,4,5-trifluorocinnamaldehyde, and the 3,4,5-trifluorocinnamaldehyde 16b (2.79 g, 15 mmol) was used as raw material to obtain 1.98 g of an off-white solid 23b with a yield of 40% (three steps), ESI(M+H)$^+$=331, and the ee of the intermediate 22b equals to 97%.

A Twenty-Second Embodiment: Synthesis of Intermediate 23c

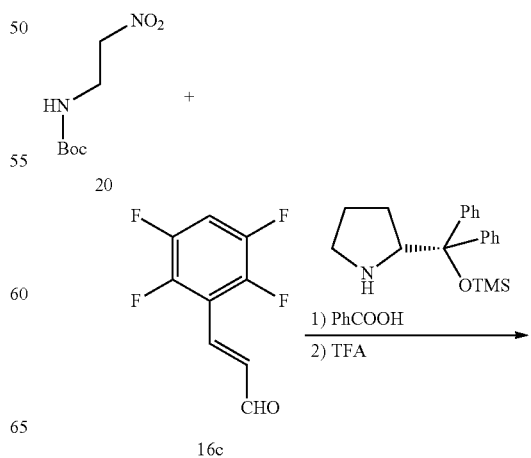

16c

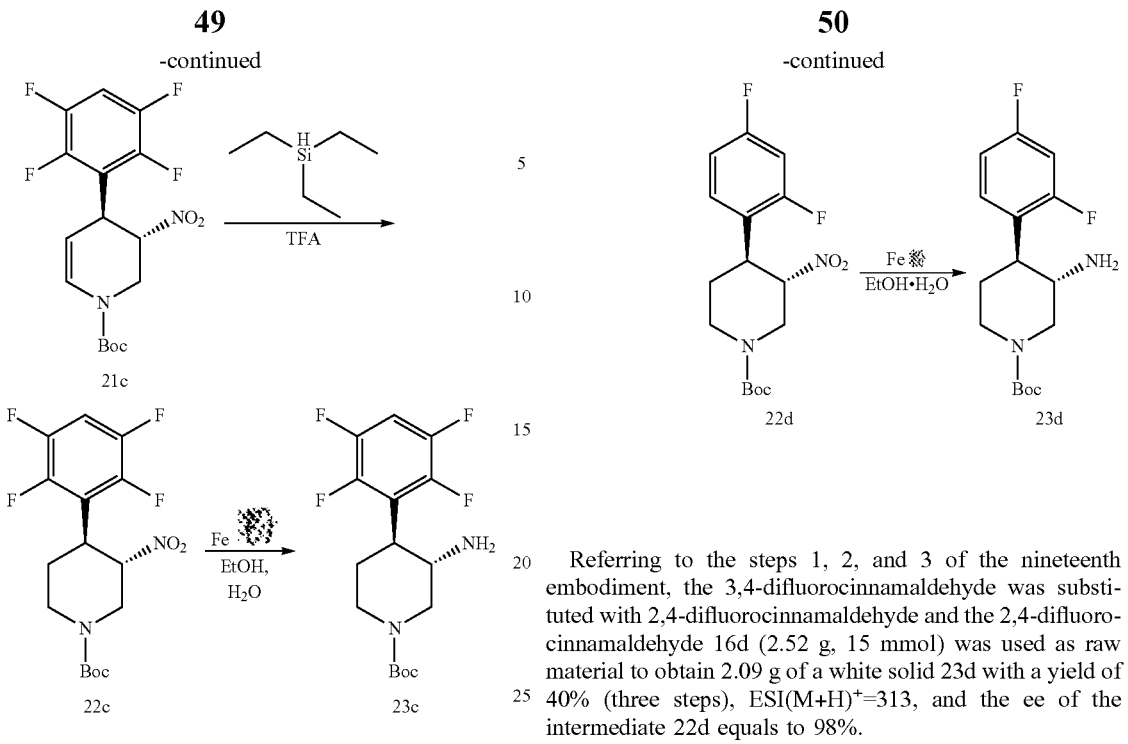

Referring to the steps 1, 2, and 3 of the nineteenth embodiment, 3,4-difluorocinnamaldehyde in the step 1 was substituted with 2,3,5,6-tetrafluorocinnamaldehyde, and the 2,3,5,6-tetrafluorocinnamaldehyde 16c (3.06 g, 15 mmol) was used as raw material to obtain 2.09 g of an off-white solid 23c with a yield of 40% (three steps), ESI(M+H)$^+$=349, and the ee of the intermediate 22c equals to 97%.

A Twenty-Third Embodiment: Synthesis of Intermediate 23d

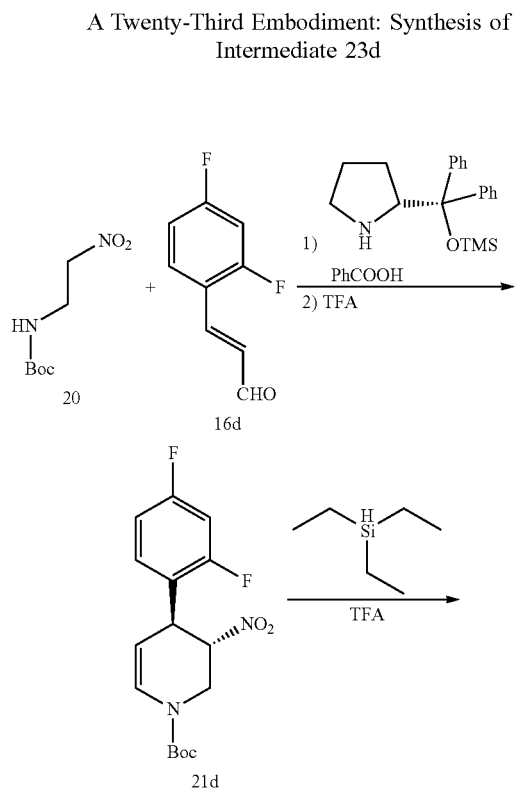

Referring to the steps 1, 2, and 3 of the nineteenth embodiment, the 3,4-difluorocinnamaldehyde was substituted with 2,4-difluorocinnamaldehyde and the 2,4-difluorocinnamaldehyde 16d (2.52 g, 15 mmol) was used as raw material to obtain 2.09 g of a white solid 23d with a yield of 40% (three steps), ESI(M+H)$^+$=313, and the ee of the intermediate 22d equals to 98%.

A Twenty-Fourth Embodiment: Synthesis of Intermediate 23e

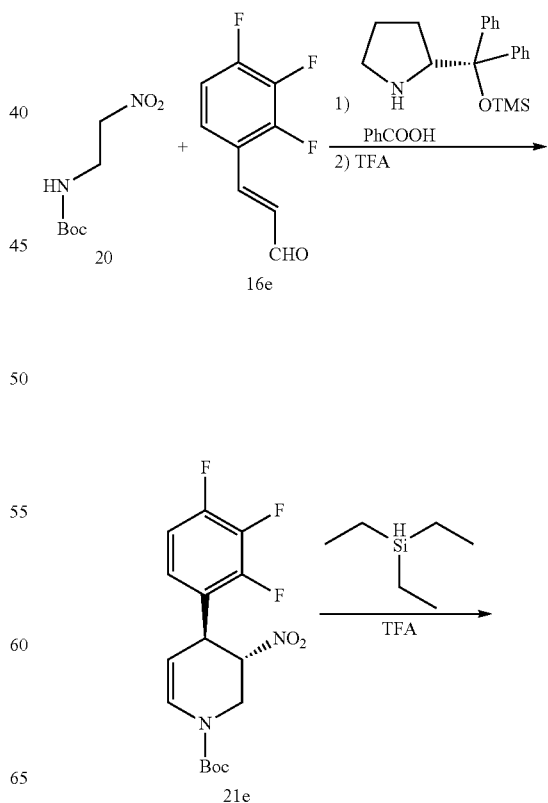

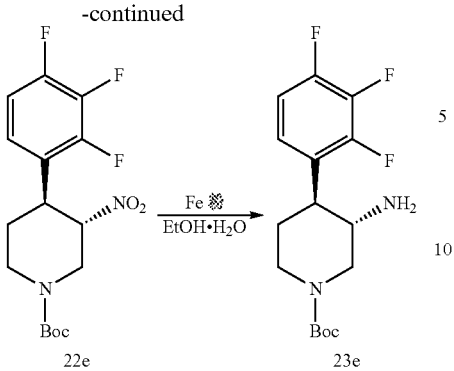

Referring to the steps 1, 2, and 3 of the nineteenth embodiment, in the step 1, 3,4-difluorocinnamaldehyde was substituted with 2,3,4-trifluorocinnamaldehyde, and the 2,3,4-trifluorocinnamaldehyde 16e (2.79 g, 15 mmol) is used as a raw material to obtain 2.09 g of a white solid 23e with a yield of 40% (three steps), ESI(M+H)$^+$=313, and the ee of the intermediate 22e equals to 97%.

A Twenty-Fifth Embodiment: Synthesis of Intermediate 23e

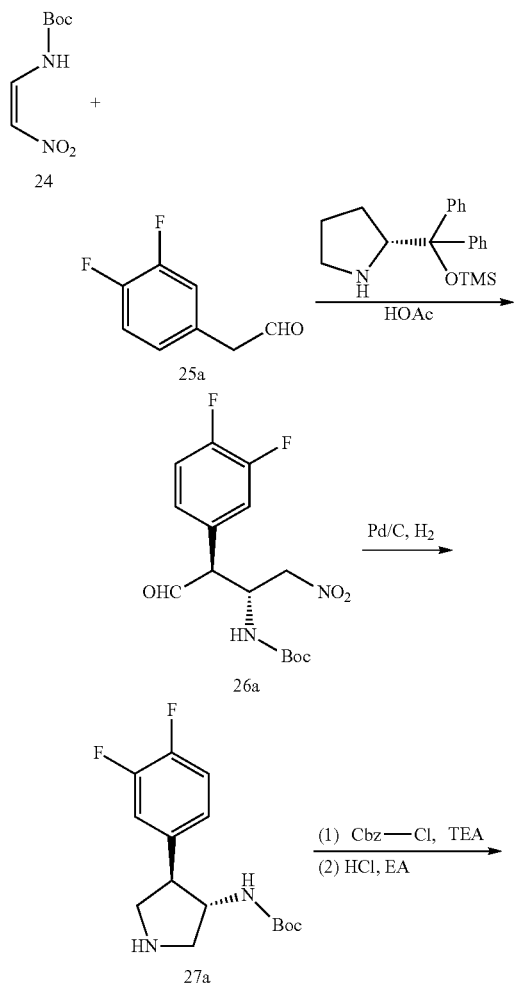

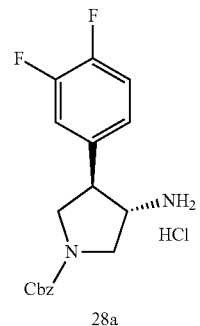

Step 1: (Z)-(2-nitrovinyl)-tert-butyl carbamate 24 (0.94 g, 5 mmol), and ((S)-(−)-α,α-diphenyl-2-pyrrolemethyl trimethylsilyl ether (0.081 g, 0.25 mmol) were sequentially added to a 50 ml of reaction bottle containing 10 ml of chloroform, and 2-(3,4-difluorophenyl)acetaldehyde 25a (1.56 g, 10 mmol) and acetic acid (30 mg, 0.5 mmol) were slowly added dropwise with stirring at room temperature, After the addition was completed, the reaction was carried out at room temperature overnight. A 30 ml of 1N sodium bicarbonate solution was added to the reaction solution with stirring at room temperature for 10 min, then the reaction solution was extracted three times with dichloromethane, and the organic phase was combined and washed with saturated sodium chloride, and dried over anhydrous sodium sulfate. The obtained crude product was subjected to silica gel column to obtain a transparent oily matter 26a with a yield of 75%.

Step 2: the 1 g of the intermediate 26a was dissolved in 10 ml of a methanol solution, and 100 mg of 10% Pd/C was added thereto, and the mixture was hydrogenated at room temperature overnight. After the completion of the reaction, the mixture was filtered, and the filtrate was evaporated to obtain 784 mg of an oily liquid 27a with a yield of 88%.

Step 3: the intermediate 27a (596 mg, 2 mmol) and triethylamine (253 mg, 2.5 mmol) were dissolved in 20 ml of dichloromethane, and benzyl chloroformate (340 mg, 2 mmol) was slowly added dropwise in an ice bath. After the completion was completed, the reaction system was moved to room temperature for 2 h, then the reaction system was diluted with 30 ml of dichloromethane, washed once with 1N HCl solution, once with saturated sodium chloride solution, dried over anhydrous sodium sulfate, and passed through a silica gel column to obtain 648 mg of a yellow oily liquid in a yield of 75%. The yellow oily liquid was dissolved in 1 ml of ethyl acetate, and then 3 ml of ethyl acetate saturated with hydrochloric acid was added, after reacting for 5 hours, the white solid in the system was filtered to obtain an intermediate 28a with a yield of 96%; ESI (M+H)$^+$=333, the ee of intermediate 28a equals to 95%.

A Twenty-Sixth Embodiment: Synthesis of Intermediate 28b

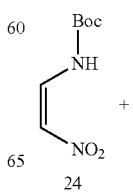

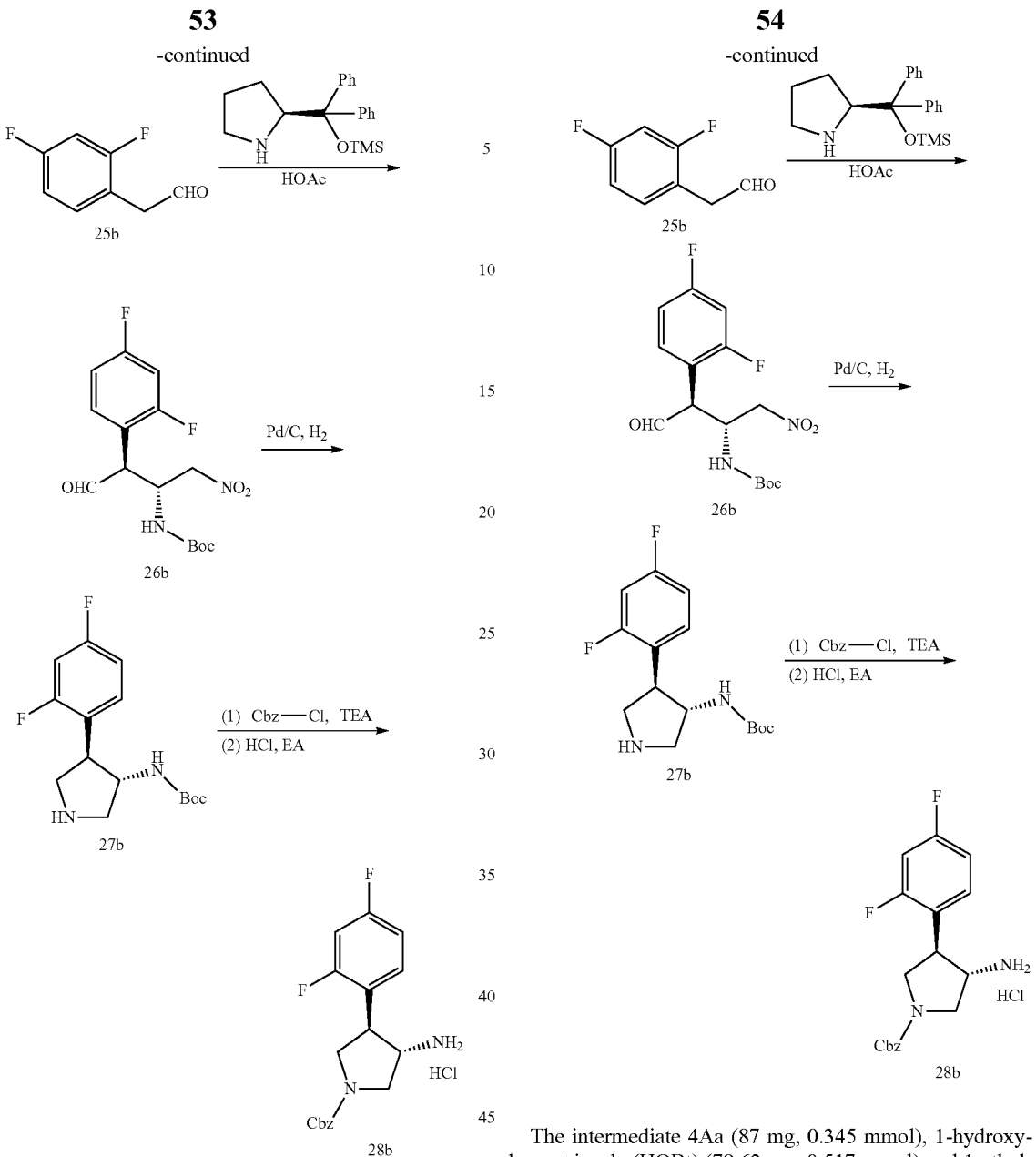

Referring to the steps 1, 2, and 3 of the twenty-forth embodiment, 2-(3,4-difluorophenyl)acetaldehyde 25a was substituted with 2-(2,4-difluorophenyl)acetaldehyde 25b to obtain an intermediate 28b in a yield of 57% (three steps), ESI (M+H)⁺=333, the ee of the intermediate 28b equals to 97%.

A twenty-seventh Embodiment: Synthesis of a Target Compound VII-1

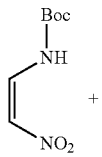

The intermediate 4Aa (87 mg, 0.345 mmol), 1-hydroxybenzotriazole (HOBt) (78.62 mg, 0.517 mmol) and 1-ethyl-(3-dimethylaminopropyl)carbodiimide hydrochloride, the salt (EDC.HCl) (98.8 mg, 0.517 mmol) were dissolved in anhydrous dichloromethane (4 ml), and the mixture was stirred for 10 min under ice bath, then diisopropylethylamine (0.115 ml, 1.21 mmol) was added, and the mixture was stirred for 15 min under ice bath, and then the dichloromethane solution (4 ml) in which the intermediate was dissolved is slowly added, and stirred at room temperature overnight, after the reaction was completed, poured into 15 ml of water, after completion of the reaction, 15 ml of water was poured into and the reaction mixture is extracted with dichloromethane three times, and the organic phase is combined, washed twice with saturated sodium chloride, dried over anhydrous sodium sulfate and revolved to dry, the resulting residue is dissolved in a small amount of ethyl acetate, hydrogen chloride saturated ethyl ester was slowly add under ice bath conditions, after the reaction was carried out for 2 hours at room temperature, spin dried and added saturated sodium bicarbonate, the reaction system was extracted two times with ethyl acetate and the organic phase is combined, dried over and the obtained crude product was purified by silica gel column chromatography to obtain 75 mg of white power (compound VII-1) in a yield of 49%. $^1$H NMR (500 MHz, MeOD-d4-d6) δ 7.68 (d, J=2.2 Hz, 1H), 7.55 (t, J=7.6 Hz, 1H), 7.42-7.34 (m, 2H), 7.32-7.26 (m, 1H), 7.24-7.21 (m, 1H), 7.20-7.16 (m, 1H), 6.55 (d, J=2.2 Hz, 1H), 4.61-4.55 (m, 1H), 3.91 (s, 3H), 3.68 (dd, J=12.4, 4.0 Hz, 1H), 3.57-3.50 (m, 1H), 3.21-3.07 (m, 3H), 2.22 (d, J=12.0 Hz, 1H), 2.09-2.01 (m, 1H); ESI(M+H)$^+$=415.

A Twenty-Eighth Embodiment: Synthesis of a Target Compound VII-1a

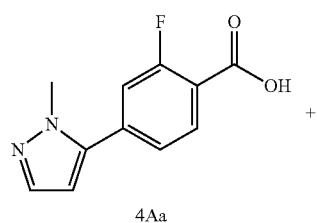

4Aa

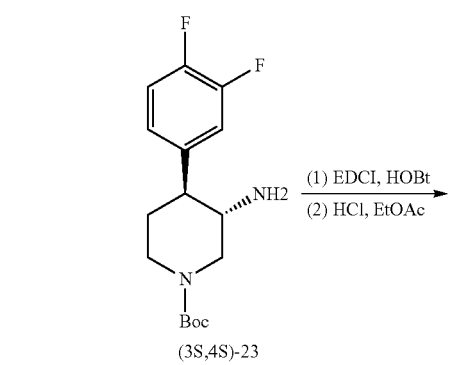

(3S,4S)-23

A Twenty-Ninth Embodiment: Synthesis of a Target Compound VII-1b

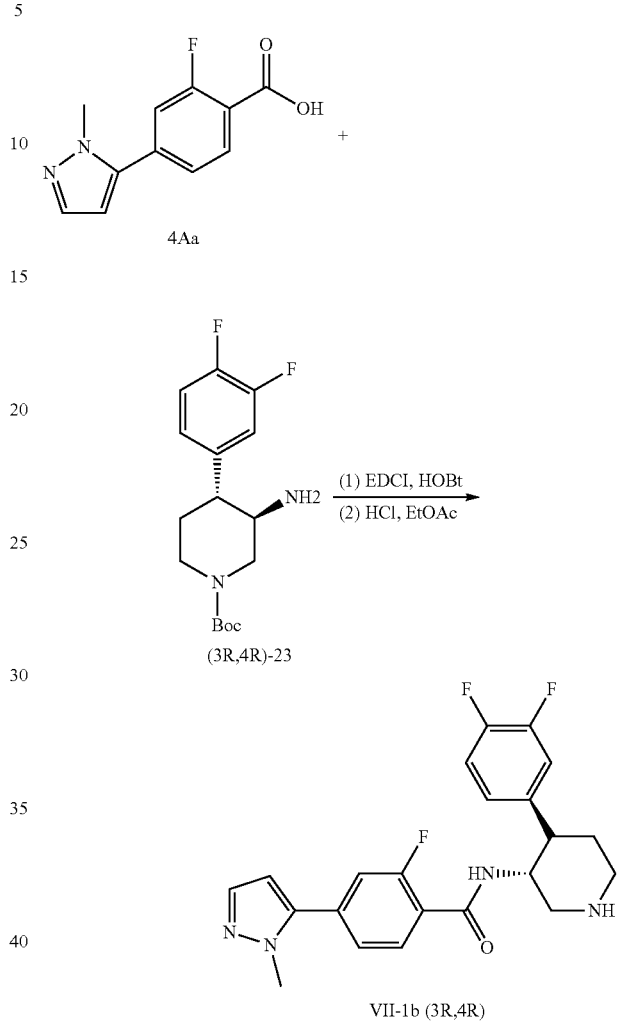

Referring to the step of the twenty-seventh embodiment, the intermediate (±) 23 was substituted with the intermediate (3R, 4R)-23, to obtain the target compound VII-1b in a yield of 43% (two steps), ESI(M+H)$^+$=415, and the measured ee of VII-1b equals to 97%.

A Thirtieth Embodiment: Synthesis of a Target Compound VII-2

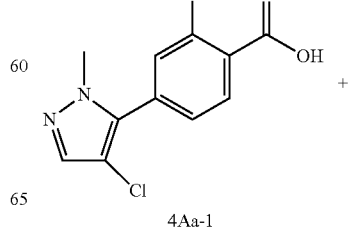

4Aa-1

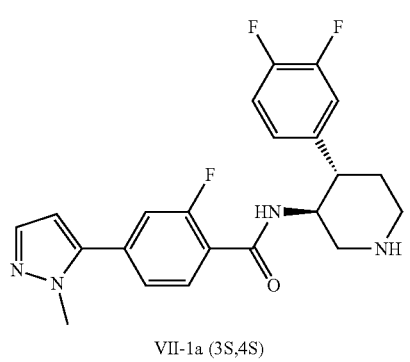

VII-1a (3S,4S)

Referring to the step of the twenty-seventh embodiment, the intermediate (±) 23 was substituted with the intermediate (3S, 4S)-23 to obtain the target compound VII-1a in a yield of 57% (two steps), ESI(M+H)$^+$=415, and the measured ee of VII-1a equals to 99%.

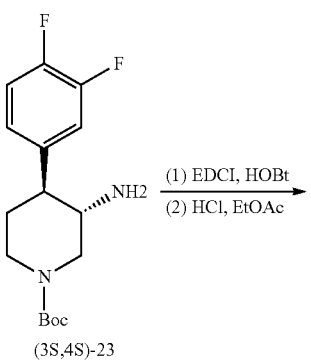

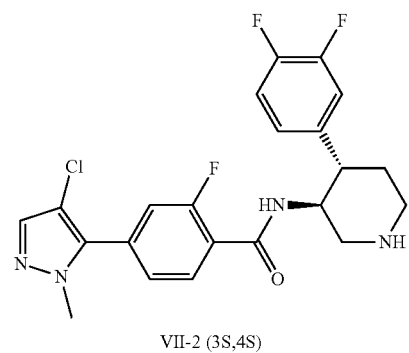

Referring to the step of the twenty-seventh embodiment, the intermediate 4Aa was substituted with the intermediate 4Aa-1 and the intermediate (±)23 was substituted with the intermediate (3S,4S)-23, to obtain the target compound VII-2 in a yield of 58% (two steps), ESI(M+H)⁺=449.

A Thirty-First Embodiment: Synthesis of a Target Compound VII-3

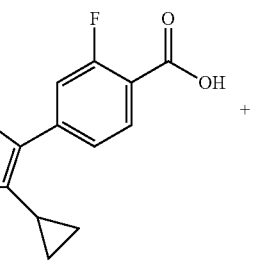

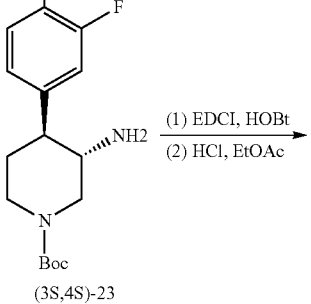

Referring to the step of the twenty-seventh embodiment, the intermediate 4Aa was substituted with the intermediate 4Ab and the intermediate (±) 23 was substituted with the intermediate (3S,4S)-23, to obtain the target compound VII-3 in a yield of 45% (two steps), ESI(M+H)⁺=429.

A Thirty-Second Embodiment: Synthesis of a Target Compound VII-4

Referring to the step of the twenty-seventh embodiment, the intermediate 4Aa was substituted with the intermediate 4Ac and the intermediate (±) 23 was substituted with the intermediate (3S,4S)-23, to obtain the target compound VII-4 in a yield of 43% (two steps), ESI(M+H)⁺=455.

A Thirty-Third Embodiment: Synthesis of a Target Compound VII-6

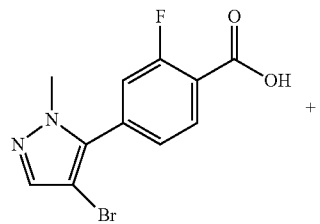

4Aa-2

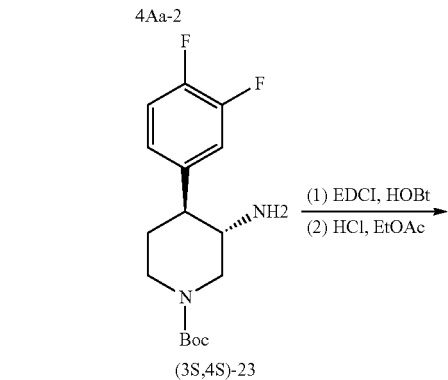

(3S,4S)-23

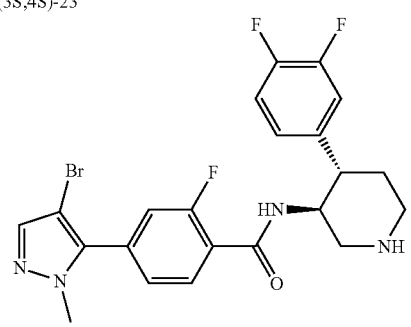

VII-6 (3S,4S)

Referring to the step of the twenty-seventh embodiment, the intermediate 4Aa was substituted with the intermediate 4Aa-2 and the intermediate (±) 23 was substituted with the intermediate (3S,4S)-23, to obtain the target compound VII-6 in a yield of 47% (two steps), ESI(M+H)⁺=493.

A Thirty-Forth Embodiment: Synthesis of a Target Compound VII-8

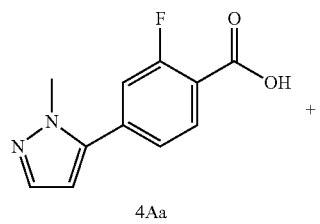

4Aa

-continued

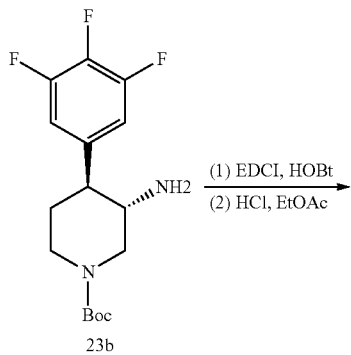

23b

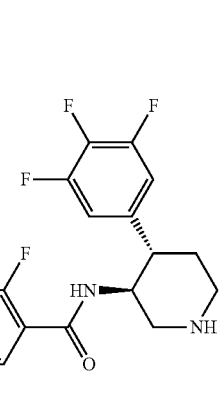

VII-8 (3S,4S)

Referring to the step of the twenty-seventh embodiment, the intermediate (±) 23 was substituted with the intermediate 23b, to obtain the target compound VII-8 in a yield of 41% (two steps), ESI(M+H)⁺=433.

A Thirty-Fifth Embodiment: Synthesis of a Target Compound VII-9

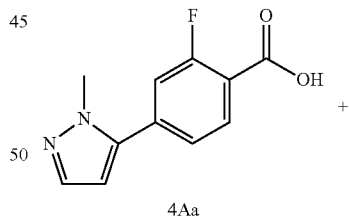

4Aa

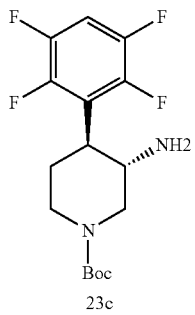

23c

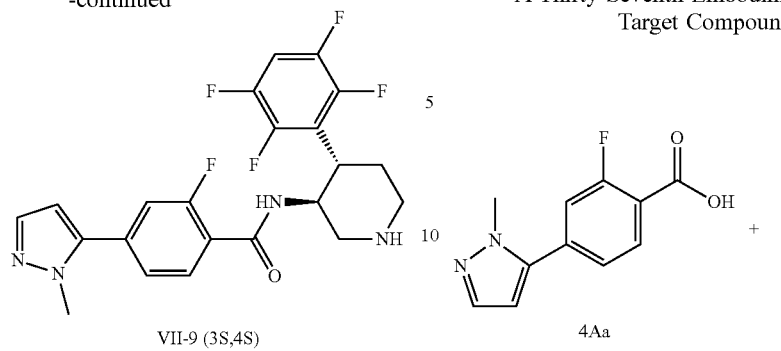

VII-9 (3S,4S)

Referring to the step of the twenty-seventh embodiment, the intermediate (±) 23 was substituted with the intermediate 23c, to obtain the target compound VII-9 in a yield of 56% (two steps), ESI(M+H)$^+$=451.

A Thirty-Sixth Embodiment: Synthesis of a Target Compound VII-10

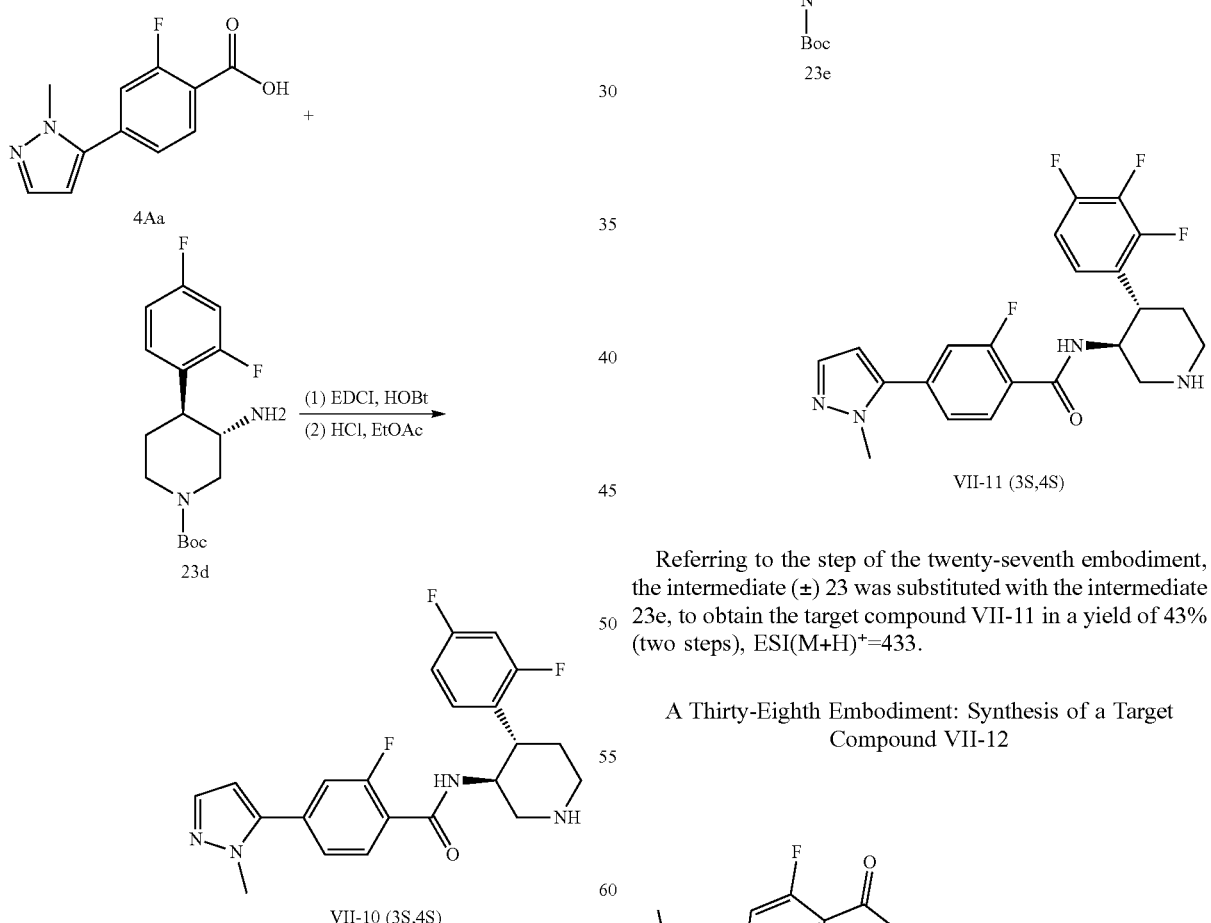

Referring to the step of the twenty-seventh embodiment, the intermediate (±) 23 was substituted with the intermediate 23d, to obtain the target compound VII-10 in a yield of 43% (two steps), ESI(M+H)$^+$=415.

A Thirty-Seventh Embodiment: Synthesis of a Target Compound VII-11

Referring to the step of the twenty-seventh embodiment, the intermediate (±) 23 was substituted with the intermediate 23e, to obtain the target compound VII-11 in a yield of 43% (two steps), ESI(M+H)$^+$=433.

A Thirty-Eighth Embodiment: Synthesis of a Target Compound VII-12

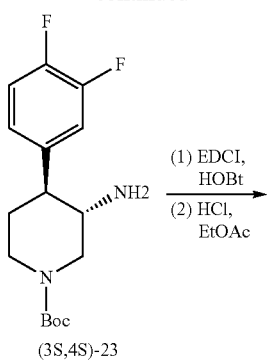

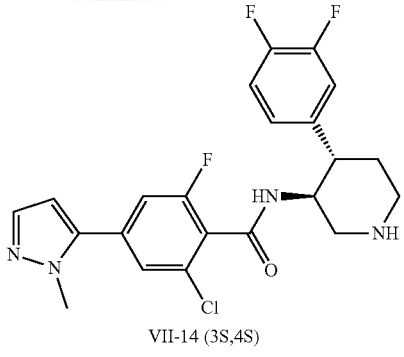 [SMILES: Cn1nccc1-c1ccc(C(=O)N[C@@H]2CNCC[C@H]2c2ccc(F)c(F)c2)cc1]

VII-14 (3S,4S)

Referring to the step of the twenty-seventh embodiment, the intermediate 4Aa was substituted with the intermediate 4Ca and the intermediate (±) 23 was substituted with the intermediate (3S,4S)-23, to obtain the target compound VII-14 in a yield of 52% (two steps), ESI(M+H)$^+$=449.

A Fortieth Embodiment: Synthesis of a Target Compound VII-15

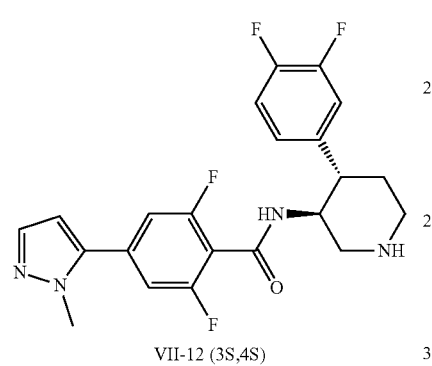

VII-12 (3S,4S)

Referring to the step of the twenty-seventh embodiment, the intermediate 4Aa was substituted with the intermediate 4Ba and the intermediate (±) 23 was substituted with the intermediate (3S,4S)-23, to obtain the target compound VII-12 in a yield of 52% (two steps), ESI(M+H)$^+$=433.

A Thirty-Ninth Embodiment: Synthesis of a Target Compound VII-14

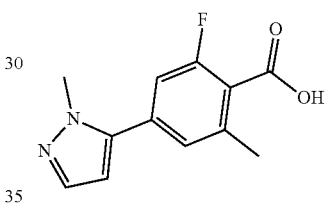

4Da

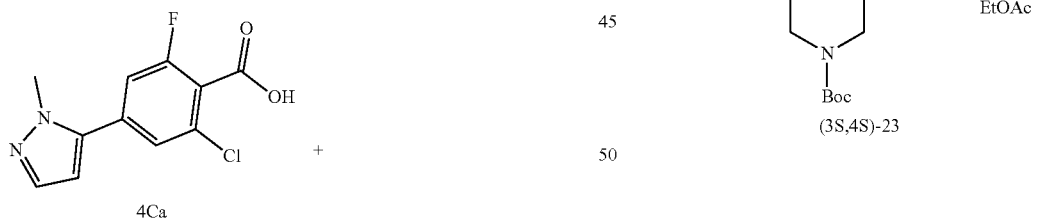

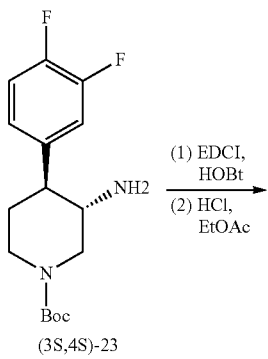

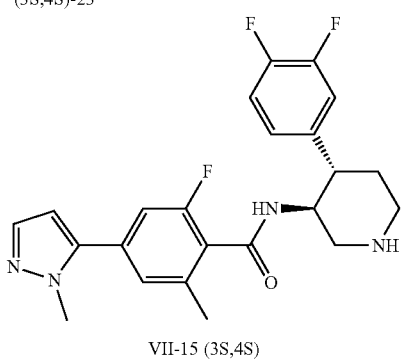

VII-15 (3S,4S)

Referring to the step of the twenty-seventh embodiment, the intermediate 4Aa was substituted with the intermediate 4 Da and the intermediate (±) 23 was substituted with the intermediate (3S,4S)-23, to obtain the target compound VII-15 in a yield of 33% (two steps), ESI(M+H)⁺=429.

A Forty-First Embodiment: Synthesis of a Target Compound VII-16

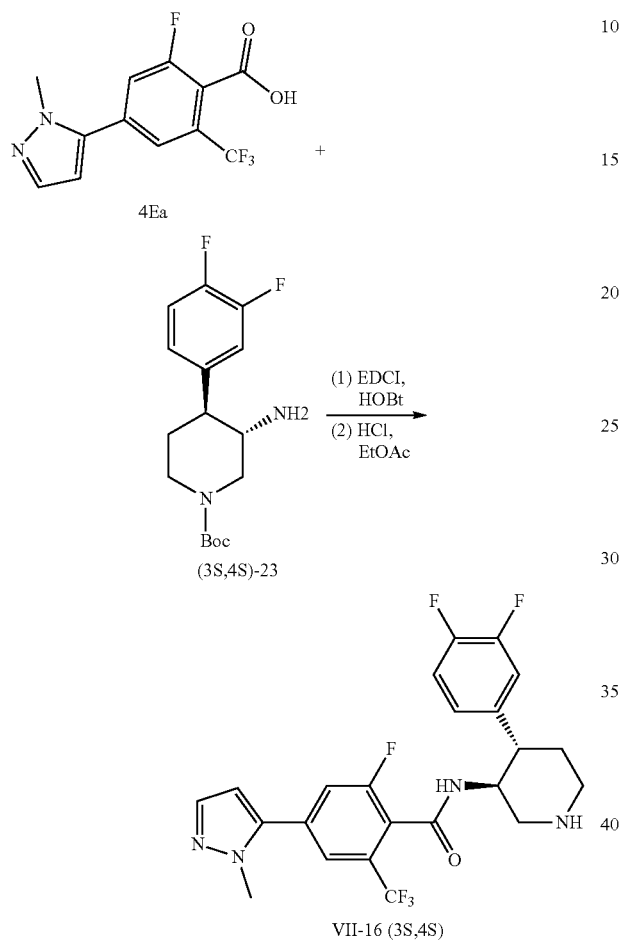

VII-16 (3S,4S)

Referring to the step of the twenty-seventh embodiment, the intermediate 4Aa is substituted with the intermediate 4Ea and the intermediate (±) 23 is substituted with the intermediate (3S,4S)-23, to obtain the target compound VII-16 in a yield of 32% (two steps), ESI(M+H)⁺=483.

A Forty-Second Embodiment: Synthesis of a Target Compound VII-17

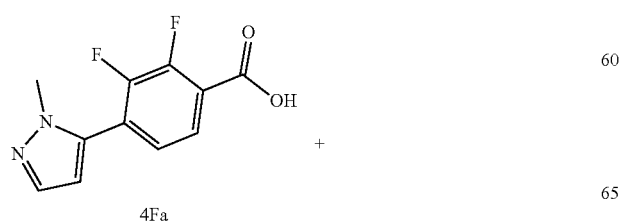

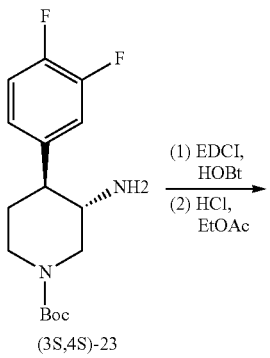

(3S,4S)-23

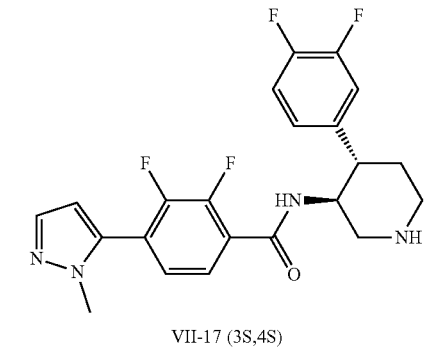

VII-17 (3S,4S)

Referring to the step of the twenty-seventh embodiment, the intermediate 4Aa was substituted with the intermediate 4Fa and the intermediate (±) 23 was substituted with the intermediate (3S,4S)-23, to obtain the target compound VII-17 in a yield of 49% (two steps), ESI(M+H)⁺=433.

A Forty-Third Embodiment: Synthesis of a Target Compound VII-18

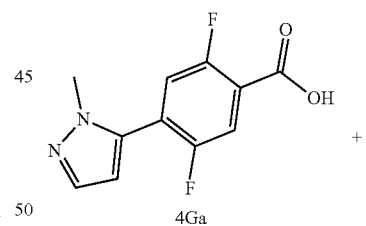

4Ga

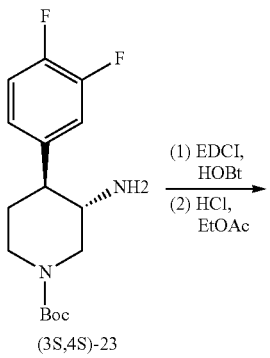

(3S,4S)-23

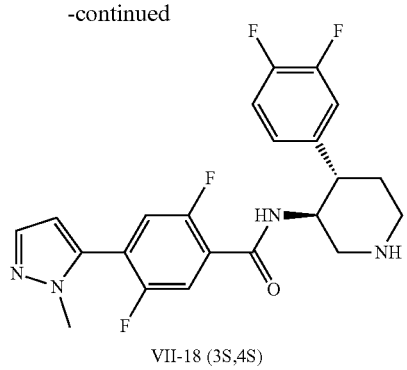

VII-18 (3S,4S)

Referring to the step of the twenty-seventh embodiment, the intermediate 4Aa was substituted with the intermediate 4Ga and the intermediate (±) 23 was substituted with the intermediate (3S,4S)-23, to obtain the target compound VII-18 in a yield of 43% (two steps), ESI(M+H)⁺=433.

A Forty-Forth Embodiment: Synthesis of a Target Compound VII-19

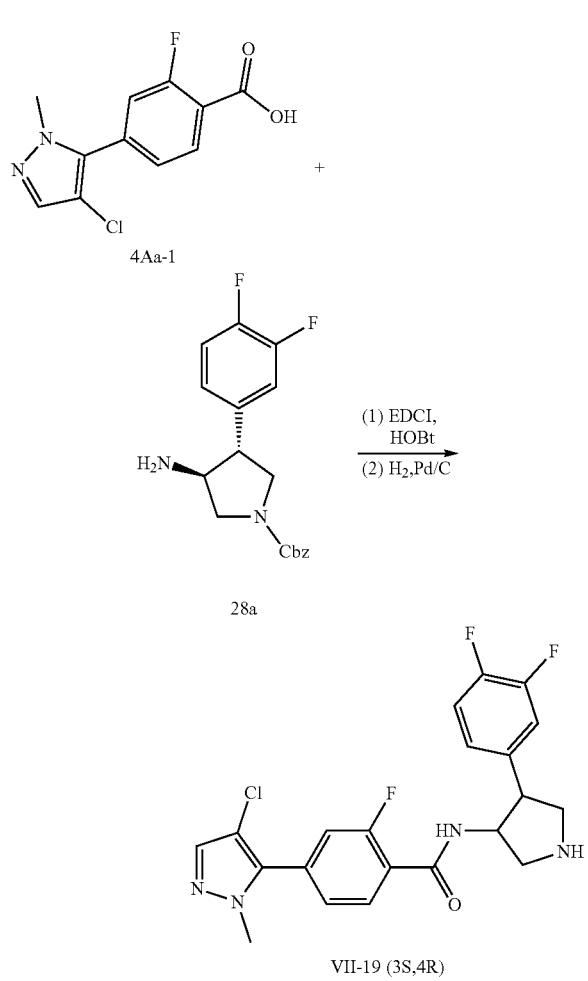

VII-19 (3S,4R)

Intermediate 4Aa-1 (97 mg, 0.345 mmol), 1-hydroxybenzotriazole (HOBt) (78.62 mg, 0.517 mmol) and 1-ethyl-(3-dimethylaminopropyl)carbodiimide hydrochloride (ED-C.HCl) (98.8 mg, 0.517 mmol) were dissolved in methylene chloride (4 ml), after stirring for 10 min in ice bath, diisopropylethylamine (0.115 ml, 1.21 mmol) was added thereto, after continuing to stir for 15 min in an ice bath, the intermediate 28a (130 mg, 0.35 mmol) was slowly added and stirred at room temperature overnight. After completion of the reaction, 15 ml of water poured into reaction mixture, and the mixture is extracted three times with dichloromethane. The organic phase was combined, washed twice with saturated sodium chloride and dried over anhydrous sodium sulphate and spin dry to obtain 122 mg of a yellow oily matter in a yield of 62%.

The yellow oily matter is dissolved in a methanol solution, and 10% Pd/C was added thereto, and the mixture was hydrogenated at room temperature overnight. After completion of the reaction, the mixture was filtered, and the filtrate was evaporated to dryness. The obtained crude product was purified by silica gel column chromatography to obtain 46 mg of a white solid VII-19 in a yield of 49%, ESI (M+H)⁺=435.

A Forty-Fifth Embodiment: Synthesis of a Target Compound VII-20

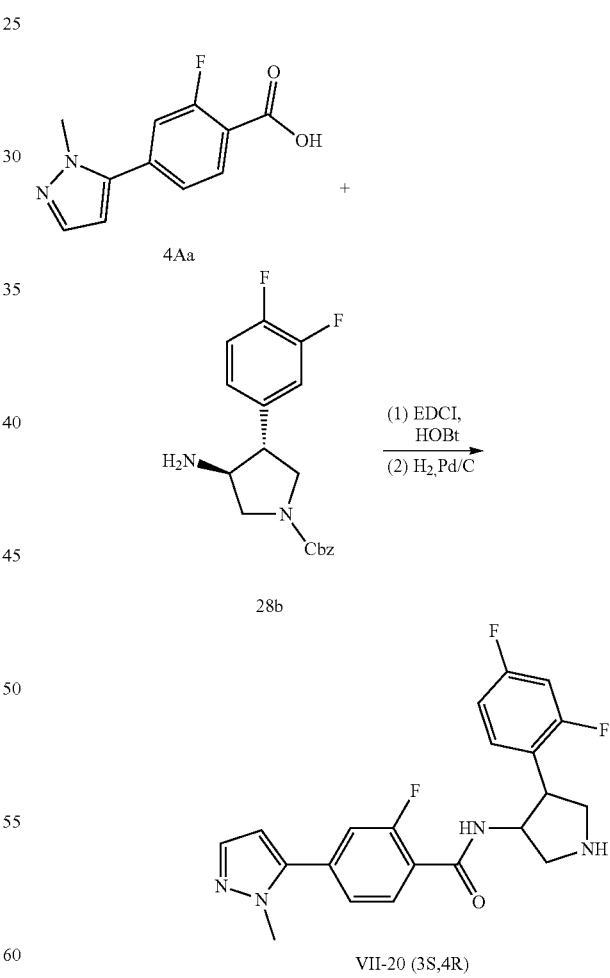

VII-20 (3S,4R)

Referring to the step of the forty-forth embodiment, the intermediate 4Aa-1 was substituted with the intermediate 4Aa and the intermediate 28A was substituted with the intermediate 28b, to obtain the target compound VII-20 in a yield of 53% (two steps), ESI(M+H)⁺=401.

A Forty-Sixth Embodiment: Synthesis of a Target Compound VII-21

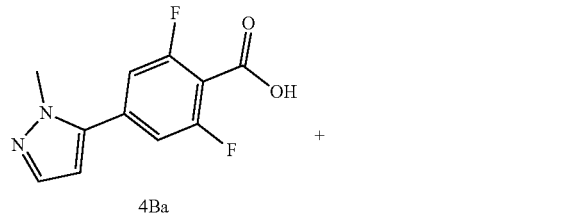

4Ba

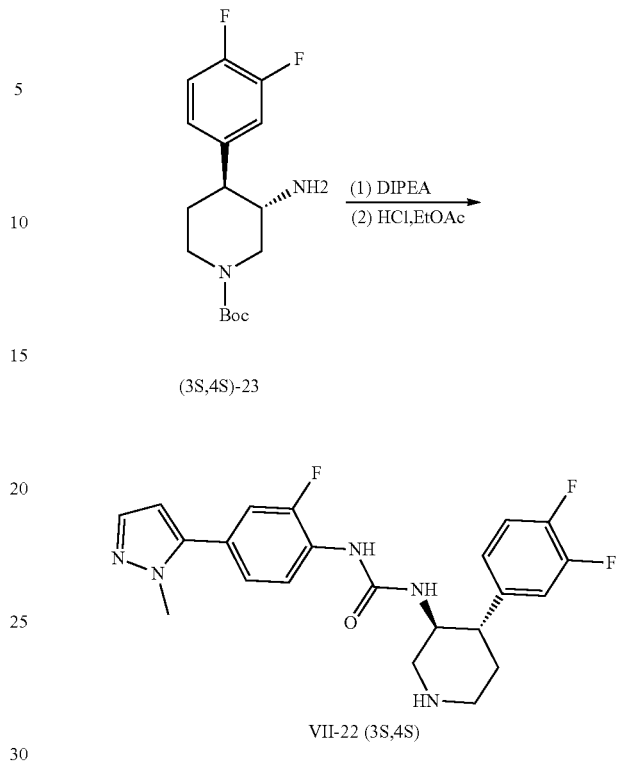

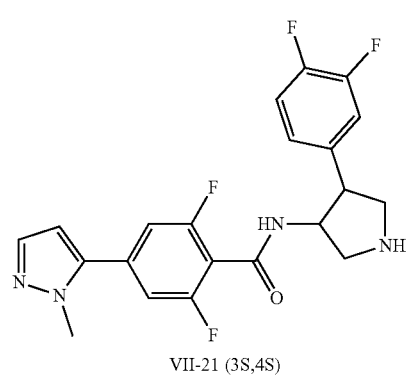

VII-21 (3S,4S)

Referring to the step of the forty-forth embodiment, the intermediate 4Aa-1 was substituted with the intermediate 4Ba, to obtain the target compound VII-21 in a yield of 56% (two steps), ESI(M+H)$^+$=419.

A Forty-Seventh Embodiment: Synthesis of a Target Compound VII-22

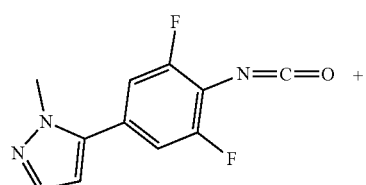

14

The intermediate 14 and DIPEA were dissolved in anhydrous dichloromethane (4 ml), and the mixture was stirred for 10 min under ice-cooling, and then the dichloromethane solution in which the intermediate was dissolved was slowly added, and stirred at room temperature for 2 h. After the reaction was completed, the organic layer was washed once with 1N aqueous hydrochloric acid and then washed twice with saturated sodium chloride, dried over anhydrous sodium sulfate and evaporated to dryness. The residue was dissolved in a small amount of ethyl acetate, ethyl chloride ethyl ester saturated with hydrogen chloride was added slowly thereto under ice bath conditions, after the reaction was carried out for 2 hours at room temperature, spin dried and added saturated sodium bicarbonate, the reaction system was extracted two times with ethyl acetate and the organic phase was combined, dried over anhydrous sodium sulfate and the obtained crude product was purified by silica gel column chromatography to obtain 75 mg of white power VII-22 in a yield of 49%, ESI(M+H)$^+$=430.

A Forty-Eighth Embodiment: Synthesis of a Target Compound VII-23

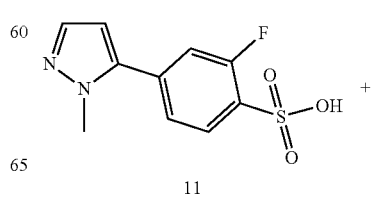

11

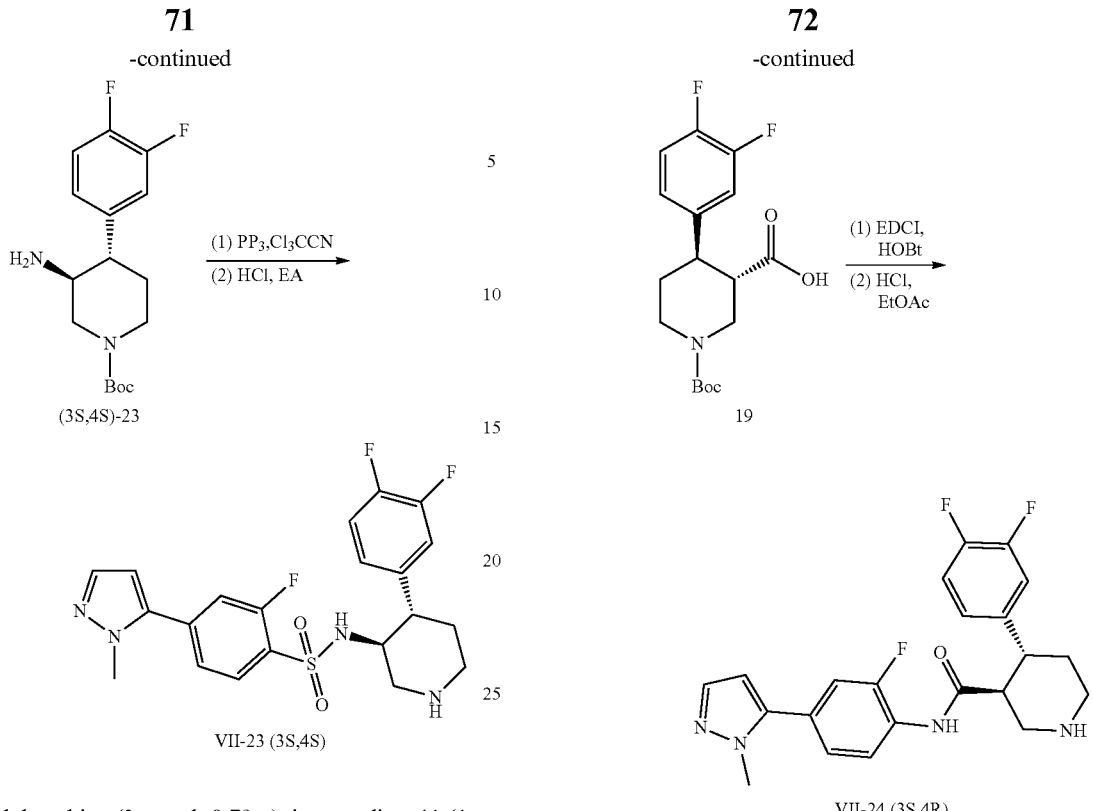

Triphenylphosphine (3 mmol, 0.79 g), intermediate 11 (1 mmol, 0.25 g) and trichloroacetonitrile (3 mmol, 0.43 g) were dissolved in 6 ml of dichloromethane and stirred to reflux for about 1 h. (3S,4S)-23 (1 mmol, 0.34 g) and 4-methylpyridine (3 mmol, 0.28 g) were added thereto, and reacted at room temperature for 1 h. After the reaction completed, the solvent was evaporated and extracted three times with ethyl acetate. The organic layer was combined and washed with a saturated aqueous solution of sodium chloride, dried over anhydrous sodium sulfate and dried. The residue was dissolved in a small amount of ethyl acetate, hydrogen chloride saturated ethyl ethyl ester was added slowly thereto under ice bath conditions, after the reaction was carried out for 2 hours at room temperature, spin dried and added saturated sodium bicarbonate, the reaction system was extracted two times with ethyl acetate and the organic phase was combined, dried over anhydrous sodium sulfate and the obtained crude product was purified by silica gel column chromatography to obtain 0.39 g of pale yellow oily matter VII-23 in a yield of 87%, ESI(M+H)$^+$=451.

A Forty-Ninth Embodiment: Synthesis of a Target Compound VII-24

Referring to the step of the forty-seventh embodiment, the intermediate 4Aa was substituted with the intermediate 19 and the intermediate (±)23 was substituted with the intermediate 13, to obtain the target compound VII-24 in a yield of 38% (two steps), ESI(M+H)$^+$=415.

A Fiftieth Embodiment: Synthesis of a Target Compound VII-26

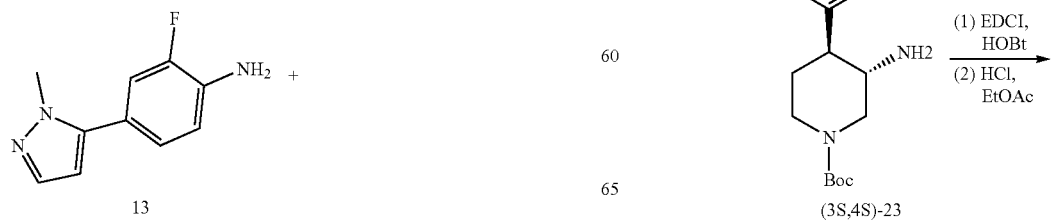

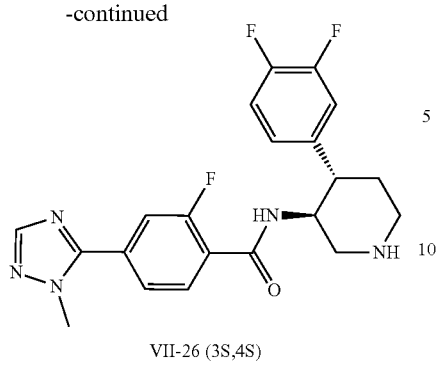

VII-26 (3S,4S)

Referring to the step of the forty-seventh embodiment, the intermediate 4Aa was substituted with the intermediate 8 and the intermediate (±)23 was substituted with the intermediate (3S,4S)-23, to obtain the target compound VII-26 in a yield of 47% (two steps), ESI(M+H)⁺=416.

A Fifty-First Embodiment: Synthesis of a Target Compound VII-27

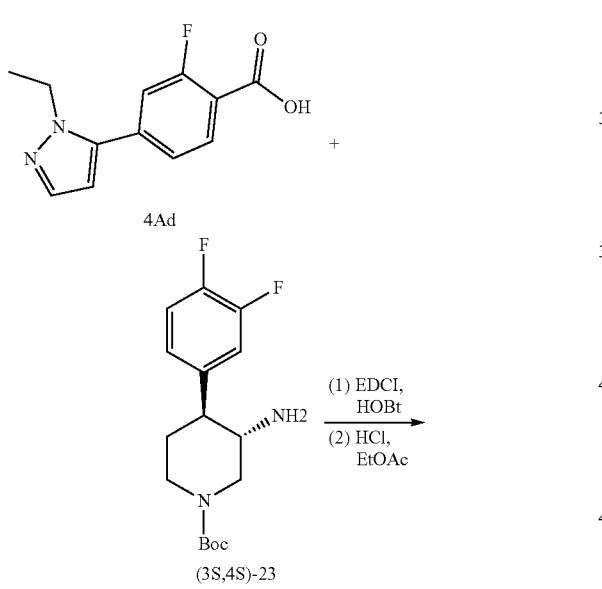

VII-27 (3S,4S)

Referring to the step of the forty-seventh embodiment, the intermediate 4Aa was substituted with the intermediate 4Ad and the intermediate (±)23 was substituted with the intermediate (3S,4S)-23, to obtain the target compound VII-27 in a yield of 49% (two steps), ESI(M+H)⁺=429.

A Fifty-Second Embodiment: Synthesis of a Target Compound VII-28

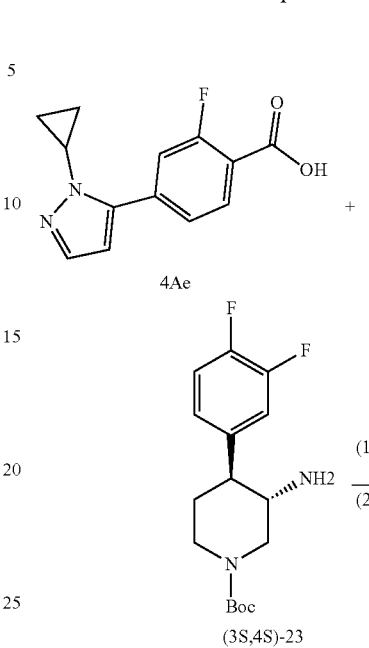

VII-28 (3S,4S)

Referring to the step of the forty-seventh embodiment, the intermediate 4Aa was substituted with the intermediate 4Ae and the intermediate (±)23 was substituted with the intermediate (3S,4S)-23, to obtain the target compound VII-28 in a yield of 57% (two steps), ESI(M+H)⁺=441.

A Fifty-Third Embodiment: Synthesis of a Target Compound VII-30

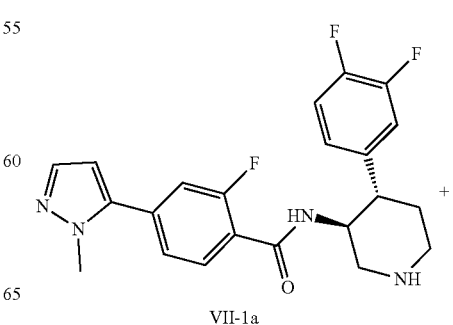

VII-1a

-continued

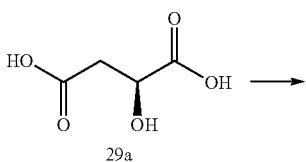
29a

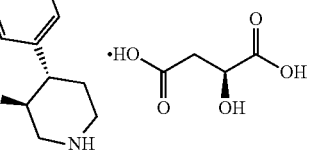
VII-30

The compound 4-(1-methyl-1H-pyrazole-yl)-N-((3S,4S)-4-(3,4-difluorophenyl)piperidin-3-yl)-2-fluoro benzoyl amide VII-1a (0.25 g, 0.60 mmol) and L-malic acid 29a (0.08 g, 0.60 mmol) were dissolved in 5 mL of absolute ethanol, dissolved in 1 ml of absolute ethanol, and reacted overnight at room temperature to precipitate a white solid, and taken filtration to obtain 0.31 g of white solid VII-30 in a yield of 93%. $^1$H NMR (500 MHz, DMSO-d6) δ 9.40 (brs, 2H), 8.42 (d, J=8.8 Hz, 1H), 7.52-7.34 (m, 4H), 7.33-7.23 (m, 1H), 7.11 (s, 1H), 6.50 (d, J=1.9 Hz, 1H), 4.36 (d, J=12.3 Hz, 1H), 3.93 (dd, J=9.5, 4.3 Hz, 1H), 3.87 (s, 3H), 3.38 (dd, J=11.5, 4.2 Hz, 1H), 3.30 (d, J=12.2 Hz, 1H), 3.00-2.84 (m, 2H), 2.78 (t, J=11.7 Hz, 1H), 2.57-2.51 (m, 1H), 2.34 (dd, J=15.6, 4.3 Hz, 1H), 2.04-1.81 (m, 2H).

A Fifty-Forth Embodiment: Synthesis of a Target Compound VII-31

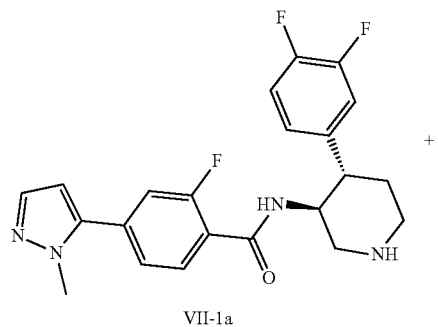
VII-1a

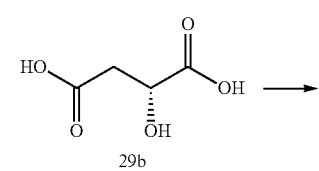
29b

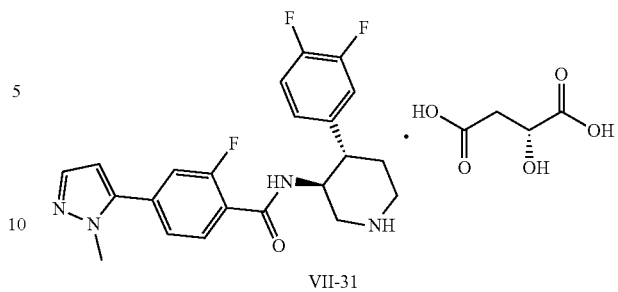
VII-31

Referring to the step of the fifty-third embodiment, the (S)-2-hydroxysuccinic acid 29a was substituted with the D-malic acid 29b (0.08 g, 0.60 mmol) and 4-(1-Methyl-1H-pyrazole-yl)-N-((3S,4S)-4-(3,4-difluorophenyl)piperidin-3-yl)-2-fluoro benzamide VII-1a (0.25 g, 0.60 mmol) was used as a raw material, to obtain 0.3 g of the white solid VII-31 in a yield of 90%.

A Fifty-Fifth Embodiment: Synthesis of a Target Compound VII-32

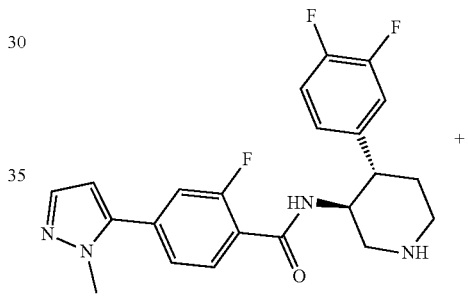
VII-1a

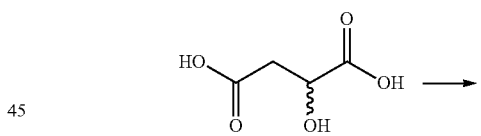
29

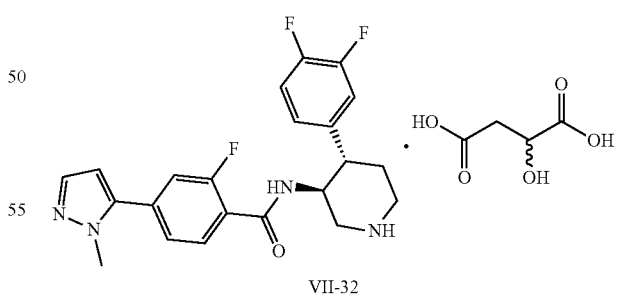
VII-32

Referring to the step of the fifty-third embodiment, the (S)-2-hydroxysuccinic acid 29a (0.08 g, 0.60 mmol) was substituted with the 2-hydroxysuccinic acid 29 and 4-(1-Methyl-1H-pyrazole-yl)-N-43S,4S)-4-(3,4-difluorophenyl)piperidin-3-yl)-2-fluoro Benzamide VII-1a (0.25 g, 0.60 mmol) was used as a raw material, to obtain 0.31 g of the white solid VII-32 in a yield of 85%.

A Fifty-Sixth Embodiment: Synthesis of a Target Compound VII-33

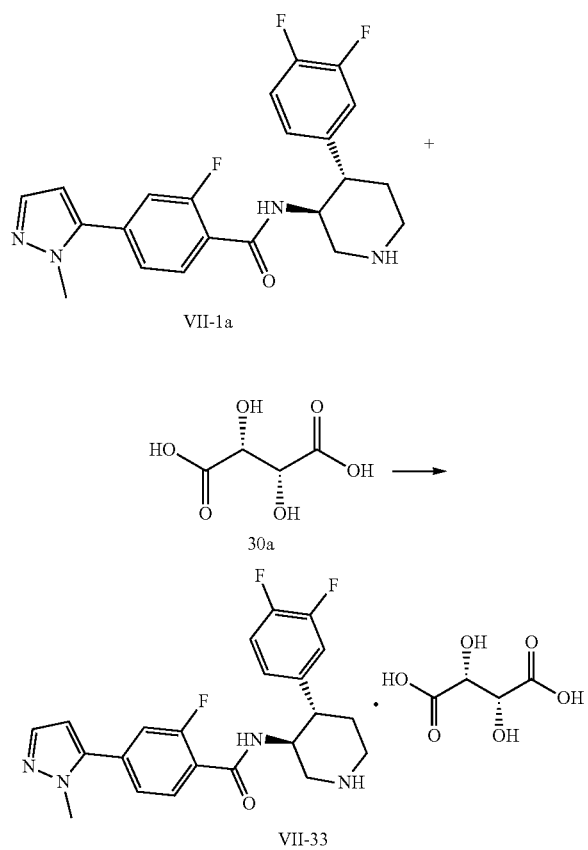

Referring to the step of the fifty-third embodiment, the (S)-2-hydroxysuccinic acid 29a was substituted with the (2R,3R)-2,3-dihydroxysuccinic acid 30a (90 mg, 0.60 mmol) and 4-(1-Methyl-1H-pyrazole-yl)-N-((3S,4S)-4-(3,4-difluorophenyl)piperidin-3-yl)-2-fluoro benzamide VII-1a (250 mg, 0.60 mmol) was used as a raw material, to obtain 0.28 g of the white solid VII-33 in a yield of 82%, ESI(M+H)$^+$=415.

A Fifty-Seventh Embodiment: Synthesis of a Target Compound VII-34

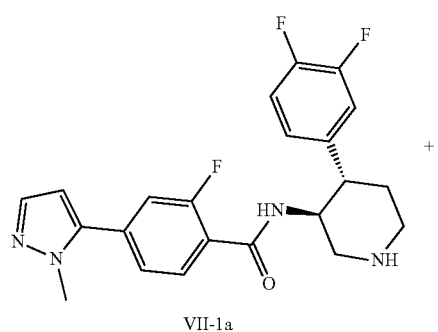

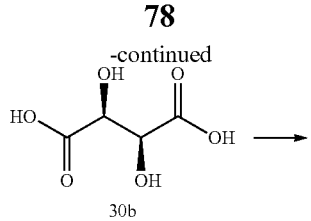

Referring to the step of the fifty-third embodiment, the (S)-2-hydroxysuccinic acid 29a was substituted with the D-tartaric acid 30b (90 mg, 0.60 mmol) and 4-(1-methyl-1H-pyrazole-yl)-N-((4S,4S)-4-(3,4-difluorophenyl)piperidin-3-yl)-2-fluorobenzoate amide VII-1a (0.2 g, 0.60 mmol) was used as a raw material, to obtain 0.29 g of the white solid VII-34 in a yield of 85%, 1H NMR (500 MHz, DMSO-d$_6$) δ 8.35 (d, J=8.9 Hz, 1H), 7.48 (d, J=1.9 Hz, 1H), 7.46 (d, J=11.6 Hz, 1H), 7.42-7.33 (m, 3H), 7.29 (ddd, J=11.8, 7.9, 1.8 Hz, 1H), 7.12 (s, 1H), 6.49 (d, J=1.9 Hz, 1H), 4.27 (td, J=10.9, 5.6 Hz, 1H), 3.91 (s, 2H), 3.86 (s, 3H), 3.30 (dd, J=12.0, 4.1 Hz, 1H), 3.20 (d, J=12.1 Hz, 1H), 2.90 (td, J=11.7, 3.8 Hz, 1H), 2.78 (t, J=11.2 Hz, 1H), 2.69 (t, J=11.6 Hz, 1H), 1.95-1.76 (m, 2H), ESI(M+H)+=415.

A Fifty-Eighth Embodiment: Synthesis of a Target Compound VII-35

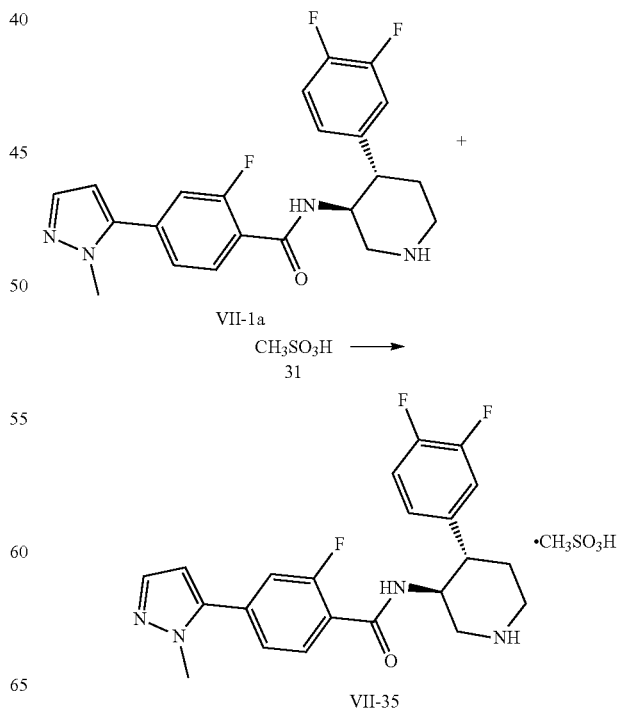

Referring to the step of the fifty-third embodiment, the (S)-2-hydroxysuccinic acid 29a was substituted with the methanesulfonic acid 31 (57 mg, 0.60 mmol) and 4-(1-methyl-1H-pyrazole-yl)-N-43S,4S)-4-(3,4-difluorophenyl)piperidin-3-yl)-2-fluorobenzoate Amide VII-1a (250 mg, 0.60 mmol) was used as a raw material, to obtain 0.24 g of the white solid VII-35 in a yield of 79%.

A Fifty-Ninth Embodiment: Synthesis of a Target Compound VII-36

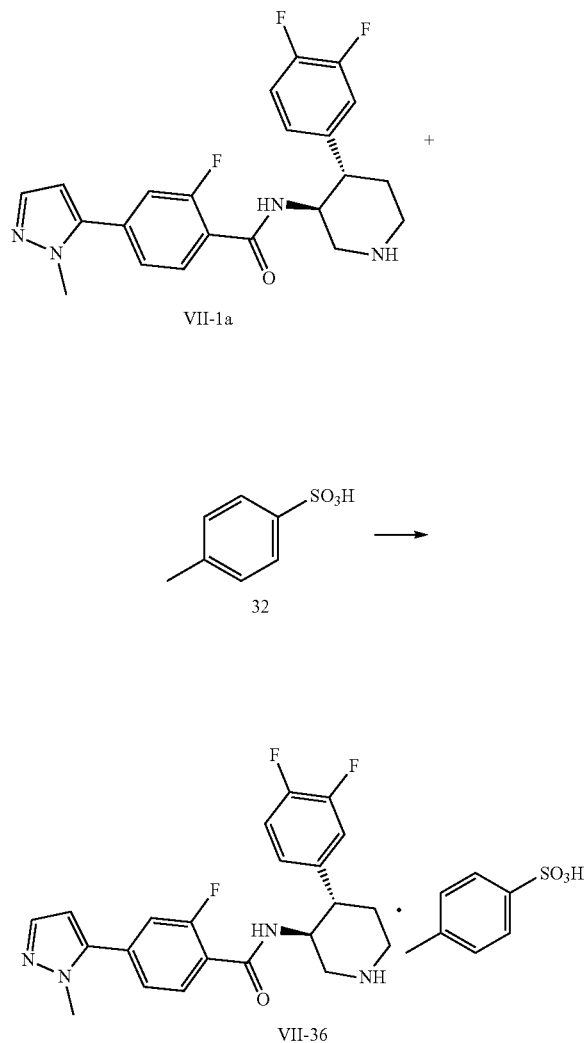

Referring to the step of the fifty-third embodiment, the (S)-2-hydroxysuccinic acid 29a was substituted with the P-toluenesulfonic acid 32 (140 mg, 0.72 mmol) and 4-(1-methyl-1H-pyrazole-yl)-N-((3S,4S)-4-(3,4-difluorophenyl)piperidin-3-yl)-2-fluorobenzoate amide VII-1a (300 mg, 0.60 mmol) was used as a raw material, to obtain 0.27 g of the white solid VII-36 in a yield of 61%.

A Sixtieth Embodiment: Synthesis of a Target Compound VII-37

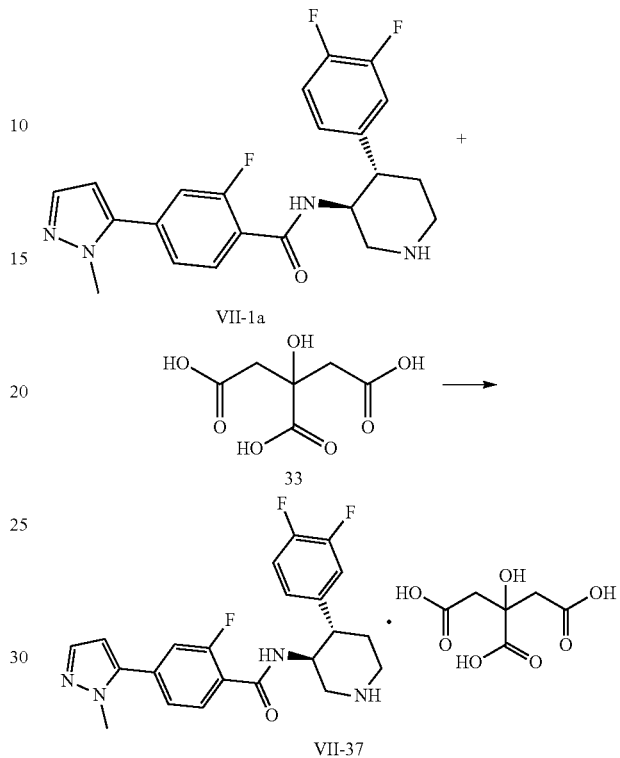

Referring to the step of the fifty-third embodiment, the (S)-2-hydroxysuccinic acid 29a was substituted with the citric acid 33 (180 mg, 0.85 mmol) and 4-(1-methyl-1H-pyrazole-yl)-N-((3S,4S)-4-(3,4-difluorophenyl)piperidin-3-yl)-2-fluorobenzoate Amide VII-1a (350 mg, 0.85 mmol) was used as a raw material, to obtain 0.27 g of the white solid VII-37 in a yield of 51%. $^1$H NMR (500 MHz, DMSO-d6) δ 9.68 (brs, 2H), 8.36 (d, J=8.9 Hz, 1H), 7.50-7.32 (m, 4H), 7.27 (ddd, J=11.8, 7.8, 1.8 Hz, 1H), 7.09 (d, J=4.6 Hz, 1H), 6.48 (d, J=1.9 Hz, 1H), 4.28 (d, J=11.9 Hz, 1H), 3.31 (dd, J=11.8, 3.8 Hz, 1H), 3.22 (d, J=12.0 Hz, 1H), 2.90 (t, J=10.1 Hz, 1H), 2.80 (t, J=11.8 Hz, 1H), 2.70 (t, J=11.4 Hz, 1H), 2.55-2.45 (m, 4H), 2.53 (d, J=15.1 Hz, 1H), 2.46 (d, J=15.1 Hz, 1H), 1.91 (d, J=11.8 Hz, 1H), 1.87-1.72 (m, 1H). 36 (d, J=8.8 Hz, 1H), 7.49-7.41 (m, 2H), 7.40-7.33 (m, 3H), 7.27 (ddd, J=12.2, 7.8, 2.1 Hz, 1H), 7.13-7.06 (m, 1H), 4.28 (d, J=11.5 Hz, 1H), 3.85 (s, 3H), 3.35-3.18 (m, 4H), 2.94-2.66 (m, 4H), 1.95-1.77 (m, 2H).

A Sixty-First Embodiment: Akt1 Enzyme Inhibitory Activity and Tumour Cell Proliferation Activity of the Compounds Disclosed in the Present Invention Compound AZD5363 (NCT02208375, NCT02208375, NCT01625286), which have entered the clinical phase II study, was used as a positive control, and the compound was assayed against common tumour cell lines (human ovarian cancer cell line OVCAR-8 and human colon cancer cell line HCT-116) by MTT assay, at the same time, the akt1 enzyme inhibitory activity (IC50) was evaluated using a commercial Akt1 kit.

1) The pharmacological test method for the tumour cell proliferation inhibiting activity of the compound of the present invention was as follows:

The first was the determination of in vitro tumour growth inhibitory activity and the preliminary structure-activity relationship study, and different solid tumour cell lines were used to determine the in vitro antitumour activity of the synthesized compounds.

Experimental materials: cell lines: human ovarian cancer cells (OVCAR8), colon adenocarcinoma cells (HCT-116),
Medium: OVCAR8: RPMI 1640+fetal calf serum
Drug preparation method: dissolving the drug in DMSO to make a 50 mM of stock solution, and diluting it to a certain ratio to obtain 5 different concentrations.

Tumour Cells being Cultured In Vitro:

The selected tumour cells were incubated in a, 5% of $CO_2$ cell incubator at 37° C., and passaged until the cell density was 70 to 90% (the adherent cells were passaged with Duck's EDTA) and used for subsequent experiments.

The compound was dissolved in dimethyl sulfoxide (DMSO), diluted, and tumour cells were seeded into 4000 cells/200 μL/well in 96-well plates, and 1 μL of compound was added to each well to a final concentration of 50 μM, 10 μM, 2 μM, and 0.4 μM. 0.08 μM were incubated in a, 5% of $CO_2$ cell incubator at 37° C. for 72 hours with DMSO (1%) as a blank control. After 72 hours, MTT with a final concentration of 0.25 mg/mL was added thereto, placed in a 5% of $CO_2$ cell incubator for 4 hours at 37° C., then the culture solution was drained, 100 μL of DMSO was added to each well, and the absorbance (OD value) was measured at 570 nm using an enzyme-linked immunometric meter, and the obtained data was used to calculate $IC_{50}$.

The calculation formula of the cell inhibition rate is: cell inhibition rate %=(control group OD value−drug group OD value)/control cell OD value×100%, and the half inhibition concentration ($IC_{50}$) was determined by the Bliss method.

2) Test method for the inhibitory activity of the compound of the present invention against Akt1 enzyme:

The AKT1/PKBα KinEASE™ FP Fluorescein Green Assay (Kinase Green Fluorescence Detection System) was used to detect the inhibitory activity of the compound on AKT1/PKBα.

Fluorescence polarization detection protein kinase B employs the principle of a competitive reaction: a fluorescently labeled phosphorylated tracer and an unlabeled phosphorylated product produced by the reaction of protein kinase B will compete with the anti-serine antibody for binding. In a reaction mixture of phosphorylated products, when a part of the fluorescent tracer binds to the antibody, it causes a higher polarization value. However, in the reaction solution mixture containing the phosphorylated product, less tracer binds to the antibody (the fluorescent tracer was replaced from the antibody) and the emitted signal was depolarized. Therefore, the change in polarization was directly related to the activity of protein kinase B in the reaction.

The compound of the present invention and the positive control AZD5363 were dissolved in dimethyl sulfoxide (DMSO) and diluted to a concentration of 50 μM. At room temperature, 0.25 μl of the compound sample and the positive control at a concentration of 50 μM were taken and added to the 384-well plate, and three parallel wells were set for each sample, and then 10 μl of STK Substrate 3, Working Solution, 5 μl AKT1/PKBα Working Solution, 10 μl ATP Working Solution were added to each sample well plate with vibrating gently and shaking for a few minutes. The reaction starts after 10 μl of ATP Working Solution was added to the well, and the reaction was timed at room temperature for 1 hour. After one hour, 5 μl of STK Stop Mix and 5 μl of STK Antibody Mix were added to each well respectively to stop the reaction. After the addition completes, it was allowed to stand at room temperature for four hours, and the polarization value of the sample was detected by the fluorescence polarization of the microplate reader (it was effective to detect its signal within 24 hours), and the inhibition rate of the compound was calculated by the polarization value, and then $IC_{50}$ was calculated.

Four sets of controls were set in the experiment, namely Buffer Control Wells, Tracer Control Wells, No Enzyme Wells, and a blank dimethyl sulfoxide control. The resulting data was used to calculate the inhibition rate.

The activity of the compound was divided into three grades according to the size of the $IC_{50}$ of the Akt inhibitory activity: "+++", 1 nM<$IC_{50}$<10 nM; "++", 10 nM<$IC_{50}$<50 nM; "+", 50 nM<$IC_{50}$.

TABLE 1

Inhibitory activity of compounds on Akt1 and antiproliferative activity against tumour cells

| Compd. | Akt1 | $IC_{50}$ (μM) | | | | |
| --- | --- | --- | --- | --- | --- | --- |
| | | HGC27 | MCF-7 | 786-O | HCT-116 | CEM-C1 |
| VII-1 | +++ | 0.06 | / | / | / | / |
| VII-1a | +++ | 0.04 | 2.25 | 0.56 | 1.34 | 0.10 |
| VII-1b | ++ | / | / | / | / | / |
| VII-2 | ++ | 0.07 | / | / | / | / |
| VII-3 | ++ | 0.09 | / | / | / | 0.16 |
| VII-4 | + | / | / | / | / | / |
| VII-6 | ++ | 0.04 | / | / | / | 0.15 |
| VII-7 | ++ | 0.06 | 2.84 | 0.99 | 2.39 | 0.09 |
| VII-8 | +++ | 0.02 | 1.85 | 1.65 | 1.52 | 0.12 |
| VII-9 | ++ | 0.08 | / | / | / | 0.21 |
| VII-10 | +++ | 0.03 | 1.89 | 0.65 | 1.98 | 0.03 |
| VII-11 | +++ | 0.07 | 2.09 | 1.41 | 2.66 | 0.01 |
| VII-12 | ++ | 0.05 | / | / | / | 0.21 |
| VII-13 | + | / | / | / | / | / |
| VII-14 | ++ | 0.10 | / | / | / | 0.18 |
| VII-15 | + | / | / | / | / | / |
| VII-16 | ++ | 0.08 | / | / | / | 0.11 |
| VII-17 | ++ | 0.04 | / | / | / | 0.09 |

TABLE 1-continued

Inhibitory activity of compounds on Akt1 and antiproliferative activity against tumour cells

| Compd. | Akt1 | IC$_{50}$ (μM) | | | | |
| --- | --- | --- | --- | --- | --- | --- |
| | | HGC27 | MCF-7 | 786-O | HCT-116 | CEM-C1 |
| VII-18 | +++ | 0.03 | 1.18 | 0.55 | 0.99 | 0.02 |
| VII-19 | ++ | 0.02 | / | / | / | 0.06 |
| VII-20 | ++ | 0.05 | / | / | / | 0.03 |
| VII-21 | ++ | 0.08 | / | / | / | 0.15 |
| VII-23 | + | / | / | / | / | / |
| VII-26 | ++ | 0.07 | / | / | / | 0.07 |
| VII-27 | ++ | 0.09 | / | / | / | 0.13 |
| VII-28 | ++ | 0.05 | / | / | / | 0.10 |
| VII-29 | ++ | 0.04 | / | / | / | 0.06 |
| VII-30 | +++ | 0.03 | 1.58 | 0.55 | 1.99 | 0.08 |
| VII-31 | +++ | 0.01 | 2.96 | 0.65 | 1.52 | 0.10 |
| VII-32 | +++ | 0.06 | 1.98 | 0.91 | 0.98 | 0.07 |
| VII-33 | +++ | 0.04 | 2.25 | 0.82 | 3.10 | 0.09 |
| VII-34 | +++ | 0.03 | 3.09 | 1.06. | 2.15 | 0.13 |
| VII-37 | +++ | 0.05 | 1.36 | 0.67 | 1.06 | 0.11 |
| 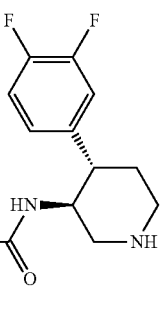 Comparative compound 6 | ++ | 0.19 | 10.56 | 2.06 | 10.51 | 0.62 |
| 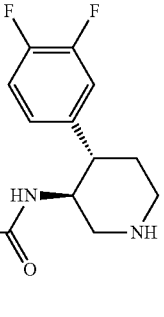 Comparative compound 11 | ++ | 0.12 | 6.32 | 1.28 | 5.86 | 0.57 |
| 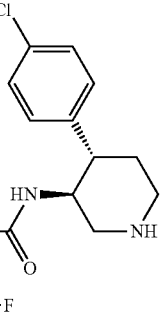 Compound 9 | +++ | 0.18 | 5.13 | 2.99 | 6.15 | 0.44 |

According to research, the present invention discloses a class of polyfluoro-substituted pyrazole-biphenylcarboxamide Akt inhibitors containing a specific substitution type, which has potent Akt1 inhibitory activity and tumour cell proliferation inhibitory activity, as shown in Table 1, when the pyrazole-biphenylcarboxamide skeleton was introduced into the F atom at the 2-position on the benzene ring, and the piperidine was substituted with at least 2 fluorine atoms in the para-phenyl ring, the antitumour activity was the biggest. Taking compound VII-1a and its salt form (VII-30 to VII-37) as an example, compound VII-1a and its salt form (VII-30~VII-37) have stronger Akt1 inhibitory activity than compounds 6 and 11 in the comparison document CN201510101220, and similarly, compared with the compounds 6, 9, 11 in the comparison document CN201510101220, compound VII-1a and its salt form (VII-30~VII-37) were more active in tumour growth inhibitory activity of tumour cell proliferation inhibitory activity (Human gastric cancer HGC27, human kidney cancer 786-0, human ovarian cancer OVCAR-8, human colon cancer HCT116, and human myeloma cells CEM-1C).

A Sixty-Second Embodiment: Kinase Selectivity Assay Test Compound Configuration

1) DMSO was configured with 50× compound stock solution for use.
2) Each compound was diluted in a 96-well plate at a concentration gradient of 5 to 7 to ensure a drug volume of 10 μl per well, to 6 to 7 concentrations, while 100 μl of DMSO was added as a blank control group, and a negative control group without an enzyme substrate was added.
3) Another 96-well plate was prepared, and 10 μl of the above compound was added to 90 μl of 1×kinase base buffer and mixed for 10 min.

The board to be tested was prepared:
1) Take a mixture of 5 μl to 384-well plates in a 96-well plate of the above configuration, and per compound has two replicate wells.

Kinase Reaction:
1) Configurate a 2.5×kinase solution and add the corresponding 1×kinase base buffer;
2) Configurate a 2.5× polypeptide solution, add a FAM-labeled polypeptide and ATP in a 1×kinase base buffer;
3) 10 μl of 2.5× kinase solution was added to the 384-well plate to be tested, put at room temperature for 10 min, then 10 μl of 2.5× polypeptide solution was added, and after reacting at 28° C. for 1 h, 25 μl of reaction stop buffer was added.

The Caliper program reads the plate and uses the data to obtain the $IC_{50}$ value of the corresponding compound inhibiting kinase. The test results are shown in Table 2.

Kinase selectivity: (other kinase inhibitory activity $IC_{50}$)/ (Akt1 inhibitory activity $IC_{50}$), the larger value represents the higher selectivity.

TABLE 2

| The kinase selectivity of the compounds | | | |
|---|---|---|---|
| kinase | VII-12 | VII-30 | GSK2141795 |
| Akt2 | 5.5-times | 5.9-times | 2-times |
| Akt3 | 4.1-times | 4.5-times | 2.6-times |
| PKA | 1.3-times | 1.77-times | 1.2-times |
| PKC | 123-times | 101-times | 28-times |

The test results of Table 2 indicate that the compounds of the present invention have subtype selectivity to Akt2 and Akt3, and VII-30 was exemplified, and its selectivity to Akt2 and Akt3 was 5.9 and 4.5 times, in contrast, GSK's Phase II clinical GSK2141795 has a selectivity of 2 and 2.6 times for Akt2 and Akt3, respectively. The current research on Akt subtype selectivity was still very limited, and the improvement of subtype selectivity was beneficial to reduce its side effects. For PKA and PKC (two targets with greater side effects), the compounds of the present invention also have certain selectivity, taking VII-30 as an example, it achieves 1.77 and 101 times selectivity for PKA and PKC, respectively and thus such compounds will have significant advantages in terms of side effects due to poor selectivity.

A Sixty-Third Embodiment: hERG Potassium Channel Inhibition Activity Experiment

1. Cell Culture
The cells used in this assay were CHO cell lines transfected with hERG cDNA and stably expressing the hERG channel (supplied by Sophion Bioscience, Denmark). The cells were cultured in medium containing the following components (all from Invitrogen): Ham's F12 medium, 10% (v/v) inactivated fetal bovine serum, 100 μg/ml hygromycin B, and 100 μg/ml Geneticin. 2.1.2CHO hERG cells were grown in a Petri dish containing the above culture solution, and cultured in an incubator containing 5% of $CO_2$ at 37° C. 24 to 48 hours prior to electrophysiological experiments, CHO hERG cells were transferred to circular glass slides placed in petri dishes and grown under the same culture and culture conditions as above. The density of CHO hERG cells on each circular slide requires that most cells achieve independent, individual requirements.

2. Compound Treatment and Dilution
To obtain the IC50 of the compound, we selecte the following concentrations (30, 10, 3, 1, 0.3, and 0.1 μM) for testing. Prior to testing, the cells were first diluted to 10, 3, 1, 0.3, and 0.1 mM stock solution in gradual dilution with DMSO and then diluted to the final μM test concentration with extracellular fluid. The final concentration of DMSO in each of the other compound solutions was 0.1% except that the DMSO concentration in the 30 μM compound test solution was 0.3%. The positive control Cisapride (cishabili) was tested at a concentration of 0.1 μM. All compound solutions were sonicated and shaken for 5 to 10 minutes to ensure complete dissolution of the compound.

3. Electrophysiological Recording System and Data Analysis
This experiment uses a manual patch clamp system (HEKA EPC-10 signal amplifier and digital conversion system, purchased from HEKA Electronics, Germany) for the recording of whole cell currents. Round slide with CHO hERG cells on the surface was placed in an electrophysiology recording cell under an inverted microscope. The extracellular fluid was continuously perfused in the recording tank (about 1 ml per minute). The experimental procedure uses conventional whole-cell patch clamp current recording techniques. Unless otherwise stated, the experiments were carried out at regular room temperature (~25° C.). The cells were clamped at a voltage of −80 mV. The cell clamp voltage was depolarized to +20 mV to activate the hERG potassium channel, and after 5 seconds it was clamped to −50 mV to eliminate inactivation and generate tail current. The tail current peak was used as the value of the hERG current magnitude. After the hERG potassium current recorded in the above step was stabilized under the continuous extracellular fluid perfusion in the recording tank, the drug to be tested can be superimposed and filled until the inhibitory effect of the drug on the hERG current reaches a steady state. Generally, the recent three consecutive current recording lines were recombined as a criterion for judging whether or not the state is stable. After reaching a steady state, extracellular fluid perfusion rinse until hERG current returns to the size before adding drug. One cell can test one or more drugs, or multiple concentrations of the same drug, but need to be flushed with extracellular fluid between different drugs. Cisapride (cisapride, purchased from Sigma) was used in the experiment as a positive control to ensure that the cells used were of normal quality. The test data was analysed by HEKA Patchmaster, Microsoft Excel and data analysis software provided by Graphpad Prism. The test results are shown in Table 3.

TABLE 3

Blocking activity of some compounds on hERG potassium channel

| Compound name | hERG (Inhibition rate at 3 μM concentration) |
| --- | --- |
| VII-1a | 15.9% |
| VII-8 | 11.8% |
| VII-10 | 21.5% |
| VII-11 | 9.6% |
| VII-18 | 17.6% |
| VII-30 | 20% |
| Comparative compound 31 | 62% |
| GSK2141795 | 50% |

The test results of Table 3 indicate that the compounds involved in the present invention have a weaker hERG channel block effect, which was significantly weaker than GSK's phase II clinical GSK2141795, and also weaker than the benzene ring substituted by a heterocyclic ring such as a furan ring 31 (WO2015/144021A1), for example, at the same concentration, the blocking effect of compound VII-30 was 0.32 and 0.4 of compound 31 and GSK2141795 respectively, since hERG channel blockade is associated with the risk of cardiotoxicity of the drug. Therefore, the low hERG potassium channel block activity of this class of compounds is beneficial to reduce the risk of side effects and improve its drug-forming properties.

A Sixty-Forth Embodiment: Oral Pharmacokinetic Experiment

Experimental methods: SD rats were used as experimental animals, and 10 mg/kg was administered by intragastric administration, and 2 mg/kg was administered intravenously to the tail vein. The blood sampling times of the tail vein administered by intragastric administration were 0.25, 0.5, 1, 2, 4, 6, 8, 10, 24 hours; the times of blood collection by intravenous administration were 0.05, 0.1, 0.17, 0.5, 1, 2, 4, 6, 8, 10, 24 hours. 0.3 ml of whole blood was taken, and after centrifugation, 0.1 ml of plasma was taken and analysed by LC-MS.

TABLE 4

Summary of main pharmacokinetic parameters of SD rats after oral administration

| parameters (Mean, n = 3) | VII-1a | VII-30 | VII-33 |
| --- | --- | --- | --- |
| administration amount (mg/kg) | 20 mg/kg | 20 mg/kg | 20 mg/kg |
| $C_{max}$ (ng/mL) | 132 | 253 | 200 |
| $T_{max}$ (h) | 4.17 | 1.75 | 4.00 |
| $_{1/2}$(h) | 3.34 | 3.63 | 3.69 |
| $AUC_{0-t}$ (ng/h/mL) | 1484 | 2354 | 1948 |
| $AUC_{0-inf}$(ng/h/mL) | 1500 | 2391 | 2157 |

The present invention examines the pharmacokinetic properties of compounds VII-1a, VII-30 and VII-33 in rats, respectively, the results of table 4 indicate that compound VII-1a can be orally absorbed and has a high exposure in vivo, $C_{max}$ reaches 132 ng/mL and AUC0-t reaches 1484 ng/h/mL. In contrast, after the organic salt was prepared, the oral bioavailability of L-malate VII-30 and D-tartrate VII-33 was significantly improved, and the AUC0-t reaches 2354 and 1948 ng/h/mL with improving 58% and 30% respectively. Studies have shown that L-malate and D-tartaric acid salt are helpful for oral absorption, which is more conducive to subsequent research and development.

A Sixty-Fifth Embodiment: In Vivo Antitumour Activity of Compounds

1) Establishment of a nude mouse xenograft model: $1\times10^7$ test tumour cells were injected into the armpit of nude mice, after three generations, HGC27 mouse tumour blocks were dissected and placed in a glass dish containing physiological saline, after the necrotic area was removed by incision, the tumour mass was cut into 1-2 mm$^3$ and inserted into the left axilla of the nude mouse with a trocar.

2) Animal grouping and drug delivery arrangements: after the tumour grows to an average volume of 100-300 mm$^3$, 20 mice were randomly grouped according to the tumour volume, and the above test animals were given the corresponding test substances by intragastric administration at a dose of 10 mL/kg with once a day.

3) Data measurement and statistics: The tumour volume was weighed and measured twice and dosing period was 21 days. On the 22nd day, after the body weight was weighed and the tumour volume was measured, the nude mice were sacrificed and the tumours were weighed to calculate the relative tumour volume (RTV), relative tumour growth rate (T/C) and tumour inhibition percentage (IR) for statistical testing. The calculation formula was as follows: (a) TV (tumour volume)=½×a×b$^2$, wherein a and b represent the length and width of the tumour respectively, (b) RTV (relative tumour volume)=$V_t/V_0$, Where $V_0$ is the tumour volume measured at the time of group administration (i.e. d0), $V_t$ is the tumour volume at each measurement, (c) T/C (%)=TRTV/CRTV×100%, wherein TRTV is the RTV of treatment group, CRTV is the RTV of the solvent control group, (d) IR (%)=(1−$TW_t/TW_c$)×100%, wherein $TW_t$ is the tumour weight of the treatment group, and $TW_c$ is the tumour weight of the solvent control group.

TABLE 5

Experimental treatment of compound gastric cancer in human gastric cancer HGC27 nude mice

| Group | Dosage (mg/kg) | Tumour volume (mm³) | | | T/C(%) |
|---|---|---|---|---|---|
| | | D1 | D22 | RTV | |
| Vehicle | — | 215 ± 66 | 6733 ± 1708 | 42.19 ± 14.08 | — |
| VII-1a | 50 | 213 ± 102 | 1498 ± 206* | 11.37 ± 3.07 | 26.95 |
| VII-30 | 50 | 215 ± 88 | 1157 ± 452* | 7.29 ± 3.03* | 17.27 |
| Compound 6 | 50 | 216 ± 98 | 1650 ± 720* | 22.60 ± 12.41 | 53.75 |

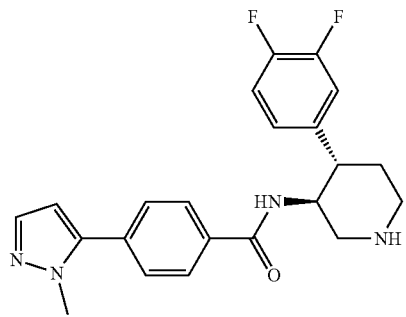

Compound 6 t-test, compared with the control, ***: $P < 0.001$, *: $P < 0.05$

TABLE 6

Effect of compounds on tumour weight of human ovarian cancer SKOV3 Nude mice xenografts ($\bar{x} \pm SE$)

| Group | Dosage (mg/kg) | Tumour volume (mm³) | | | T/C (%) |
|---|---|---|---|---|---|
| | | D 1 | D 22 | RTV | |
| Vehicle | — | 125 ± 55 | 2475 ± 528 | 25.12 ± 6.20 | — |
| VII-3 0 | 50 | 117 ± 65 | 248 ± 19* | 3.60 ± 2.67 | 32.96 | t-test, compared with the control,
***$P < 0.001$,
*$P < 0.05$

TABLE 7

Experimental treatment of human kidney cancer 786-O nude mice xenografts ($\bar{x} \pm SE$)

| Group | Dosage (mg/kg) | Tumour volume (mm³) | | | T/C (%) |
|---|---|---|---|---|---|
| | | D 1 | D 21 | RTV | |
| Vehicle | — | 125 ± 30 | 1330 ± 264 | 11.46 ± 1.69 | — |
| VII-3 0 | 100 | 126 ± 13 | 127 ± 51** | 1.06 ± 0.43** | 9.26 |
| VII-3 0 | 50 | 125 ± 14 | 328 ± 105 | 2.62 ± 0.83* | 22.86 | t-test, compared with the control,
***$P < 0.001$,
*$P < 0.05$

As shown in Tables 5, 6, and 7, compounds VII-1a and VII-30 have potent in vivo antitumour activity, taking compound VII-30 as an example (50 mg/kg, gavage), and in human gastric cancer HGC27 nude mice xenografts, human ovarian cancer SKOV3 nude mice xenografts, and human kidney cancer 786-0 nude mice xenografts, tumour growth can be effectively inhibited, and its T/C reaches 17.27%, 32.96% and 22.86% respectively, its in vivo antitumour activity was superior to the free form of VII-1a (Table 4), and the results were consistent with the results of pharmacokinetic properties, indicating that salt formation with L-malic acid helps to increase its antitumour activity in vivo. Compound VII-1a and its malate salt have stronger in vivo antitumour activity than compound 6 in comparative document CN201510101220.

In summary, the polyfluoro-substituted nitrogen heterocyclic derivatives of the present invention have broad antitumour application prospects

The invention claimed is:

1. A polyfluoro-substituted aromatic heterocyclic derivative, having a structure as represented by formula I or formula I',

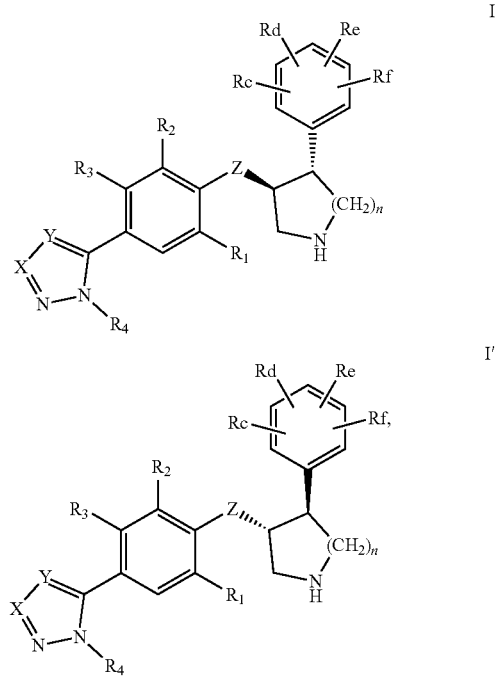

or an optical isomer thereof;
or a pharmaceutically acceptable salt or solvate thereof;
or a pharmaceutically acceptable salt or solvate of the optical isomer thereof,
wherein X and Y are independently selected from —C(Ra)— and —N—, and at least one of them is —C(Ra)—; Ra is selected from H, halogen, hydroxy, carboxyl, hydroxymethyl, saturated or unsaturated $C_1$-$C_4$ hydrocarbyl, halogenated $C_1$-$C_4$ alkyl, $C_1$-$C_4$ alkoxy, halogenated $C_1$-$C_4$ alkoxy, unsubstituted or substituted aryl of $C_4$-$C_{12}$, unsubstituted or substituted heterocyclic aryl of $C_4$-$C_{12}$, unsubstituted or substituted cycloalkyl of $C_3$-$C_8$;

$R_1$ and $R_2$ are each independently selected from a group consisting of H, F, Cl, Br, $CH_3$, and $CF_3$, and at least one of them is a fluorine atom;

$R_3$ is H, $CH_3$, $CF_3$, F or Cl;

$R_4$ is a $C_1$-$C_3$ alkyl or cycloalkyl;

Z is selected from

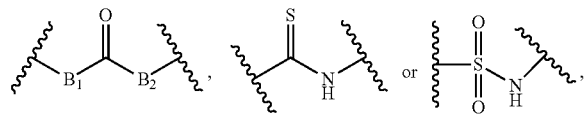

$B_1$ and $B_2$ are each independently selected from N(Rb) or a deletion, wherein Rb is independently selected from H, $C_1$-$C_3$ alkyl or cycloalkyl;

n is 1, 2, or 3, and

Rc, Rd, Re, and Rf are each independently selected from a group consisting of H, F, Cl, Br, $CF_3$, and $CF_2H$, and at least two of substituents are fluorine atoms;

characterised in that, the polyfluoro-substituted aromatic heterocyclic derivative comprises:
4-(1-methyl-1H-pyrazole-yl)-N-((3S,4S)-4-(3,4-difluorophenyl)piperidin-3-yl)-2-fluorobenzamide L-malate,
4-(1-methyl-1H-pyrazole-yl)-N-((3S,4S)-4-(3,4-difluorophenyl)piperidin-3-yl)-2-fluorobenzamide D-malate,
4-(1-methyl-1H-pyrazole-yl)-N-((3S,4S)-4-(3,4-difluorophenyl)piperidin-3-yl)-2-fluorobenzamide (±)-malate,
4-(1-methyl-1H-pyrazole-yl)-N-((3S,4S)-4-(3,4-difluorophenyl)piperidin-3-yl)-2-fluorobenzamide L-tartrate,
4-(1-methyl-1H-pyrazole-yl)-N-((3S,4S)-4-(3,4-difluorophenyl)piperidin-3-yl)-2-fluorobenzamide D-tartrate,
4-(1-Methyl-1H-pyrazole-yl)-N-((3S,4S)-4-(3,4-difluorophenyl)piperidin-3-yl)-2-fluorobenzamide methanesulfonate,
4-(1-methyl-1H-pyrazole-yl)-N-((3S,4S)-4-(3,4-difluorophenyl)piperidin-3-yl)-2-fluorobenzamide p-toluene sulfonate,
4-(1-methyl-1H-pyrazole-yl)-N-((3S,4S)-4-(3,4-difluorophenyl)piperidin-3-yl)-2-fluorobenzamide citrate, or
optical isomers thereof; or pharmaceutically acceptable solvate thereof.

2. The polyfluoro-substituted aromatic heterocyclic derivative according to claim 1, characterised in that, the pharmaceutically acceptable salt is a salt formed with the following acids: citric acid, fumaric acid, acetic acid, oxalic acid, tartaric acid, malic acid, maleic acid, lactic acid, camphorsulfonic acid, p-toluenesulfonic acid, methanesulfonic acid, trifluoromethanesulfonic acid, benzenesulfonic acid, succinic acid, lemon acid, haloid acid sulfuric acid, phosphoric acid, nitric acid, carbonic acid, glutamic acid, or aspartic acid.

3. A pharmaceutical composition, characterised in that, the pharmaceutical composition includes at least one active ingredient and one or more pharmaceutically acceptable carriers or excipients, wherein the active ingredient is the polyfluoro-substituted aromatic heterocyclic derivative according to claim 1.

4. The polyfluoro-substituted aromatic heterocyclic derivative according to claim 1, characterised in that, the polyfluoro-substituted aromatic heterocyclic derivative includes:
4-(1-methyl-1H-pyrazole-yl)-N-((3 S,4S)-4-(3,4-difluorophenyl)piperidin-3-yl)-2-fluorobenzamide L-malate, or other optical isomers thereof; or pharmaceutically acceptable solvate thereof.

* * * * *